United States Patent
Lowery et al.

(10) Patent No.: US 6,949,064 B2
(45) Date of Patent: Sep. 27, 2005

(54) BRACHYTHERAPY SEED DEPLOYMENT SYSTEM

(75) Inventors: Guy Russell Lowery, San Juan Capistrano, CA (US); Eric E. Bowman, Flower Mound, TX (US)

(73) Assignee: Bard Brachytherapy, Inc., Carol Stream, IL (US)

(*) Notice: Subject to any disclaimer, the term of this patent is extended or adjusted under 35 U.S.C. 154(b) by 0 days.

(21) Appl. No.: 10/217,339

(22) Filed: Aug. 9, 2002

(65) Prior Publication Data

US 2003/0109769 A1 Jun. 12, 2003

Related U.S. Application Data

(63) Continuation-in-part of application No. 09/694,107, filed on Oct. 20, 2000, now Pat. No. 6,530,875.

(51) Int. Cl.[7] ............................ A61M 36/00; A61N 5/00
(52) U.S. Cl. .......................................................... 600/7
(58) Field of Search ....................... 600/1–8; 724/1.11; 606/130, 194, 198, 1; 604/19, 53, 103, 104, 106, 107, 202, 93, 96; 623/1.42, 1.21; 426/6; 376/158, 195, 201

(56) References Cited

U.S. PATENT DOCUMENTS

| | | | |
|---|---|---|---|
| 4,402,308 A | 9/1983 | Scott | |
| 4,697,575 A | 10/1987 | Horowitz | |
| 4,706,652 A | 11/1987 | Horowitz | |
| 4,754,745 A | 7/1988 | Horowitz | |
| 4,763,642 A | 8/1988 | Horowitz | |
| 4,784,116 A | 11/1988 | Russell, Jr. et al. | |
| 4,815,449 A | 3/1989 | Horowitz | |
| 4,819,618 A | 4/1989 | Liprie | |
| 5,199,939 A | 4/1993 | Dake et al. | |
| 5,282,781 A | 2/1994 | Liprie | |
| 5,342,283 A | 8/1994 | Good | |
| 5,460,592 A | 10/1995 | Langton et al. | |
| 5,713,828 A | 2/1998 | Coniglione | |
| 5,928,130 A | 7/1999 | Schmidt | |
| 5,938,583 A | 8/1999 | Grimm | |
| 6,010,446 A | 1/2000 | Grimm | |

(Continued)

FOREIGN PATENT DOCUMENTS

| | | |
|---|---|---|
| WO | WO 97/19706 | 6/1997 |
| WO | WO 97/19724 | 6/1997 |
| WO | WO 00/64538 | 11/2000 |
| WO | WO 02/36199 | 5/2002 |

OTHER PUBLICATIONS

Onco Seed (Iodine–125–Seeds)Rapid Strand Rigid Absorbable Permanent Implant Device No. 7000, Medi–Physics, Inc., Oct. 1999.

Primary Examiner—Max F. Hindenburg
Assistant Examiner—Brian Szmal
(74) Attorney, Agent, or Firm—Stroock & Stroock & Lavan LLP

(57) ABSTRACT

Disclosed is a brachytherapy seed deployment system for use in any of a variety of medical procedures such as radiation treatment of the prostate gland. The system includes at least two seeds secured together by a filament, which may be rigid or flexible. Also provided are methods of assembling the seeds and filaments, and methods of treating cancerous tissue using the seeds and filaments.

54 Claims, 51 Drawing Sheets

U.S. PATENT DOCUMENTS

| | | | |
|---|---|---|---|
| 6,080,009 A | 6/2000 | Yanagihara et al. | |
| 6,099,457 A | 8/2000 | Good | |
| 6,210,315 B1 | 4/2001 | Andrews et al. | |
| 6,221,003 B1 | 4/2001 | Sierocuk et al. | |
| 6,245,052 B1 | 6/2001 | Orth et al. | |
| 6,248,057 B1 | 6/2001 | Mavity et al. | |
| 6,264,599 B1 | 7/2001 | Slater et al. | |
| 6,264,600 B1 * | 7/2001 | Grimm | 600/7 |
| 6,270,472 B1 | 8/2001 | Antaki et al. | |
| 6,273,851 B1 | 8/2001 | Slater et al. | |
| 6,287,249 B1 | 9/2001 | Tam et al. | |
| 6,450,937 B1 | 9/2002 | Mercereau et al. | |
| 6,450,939 B1 | 9/2002 | Grimm | |
| 6,503,185 B1 * | 1/2003 | Waksman et al. | 600/3 |
| 6,749,553 B2 * | 6/2004 | Brauckman et al. | 600/3 |
| 2001/0008951 A1 | 7/2001 | Sierocuk | |

* cited by examiner

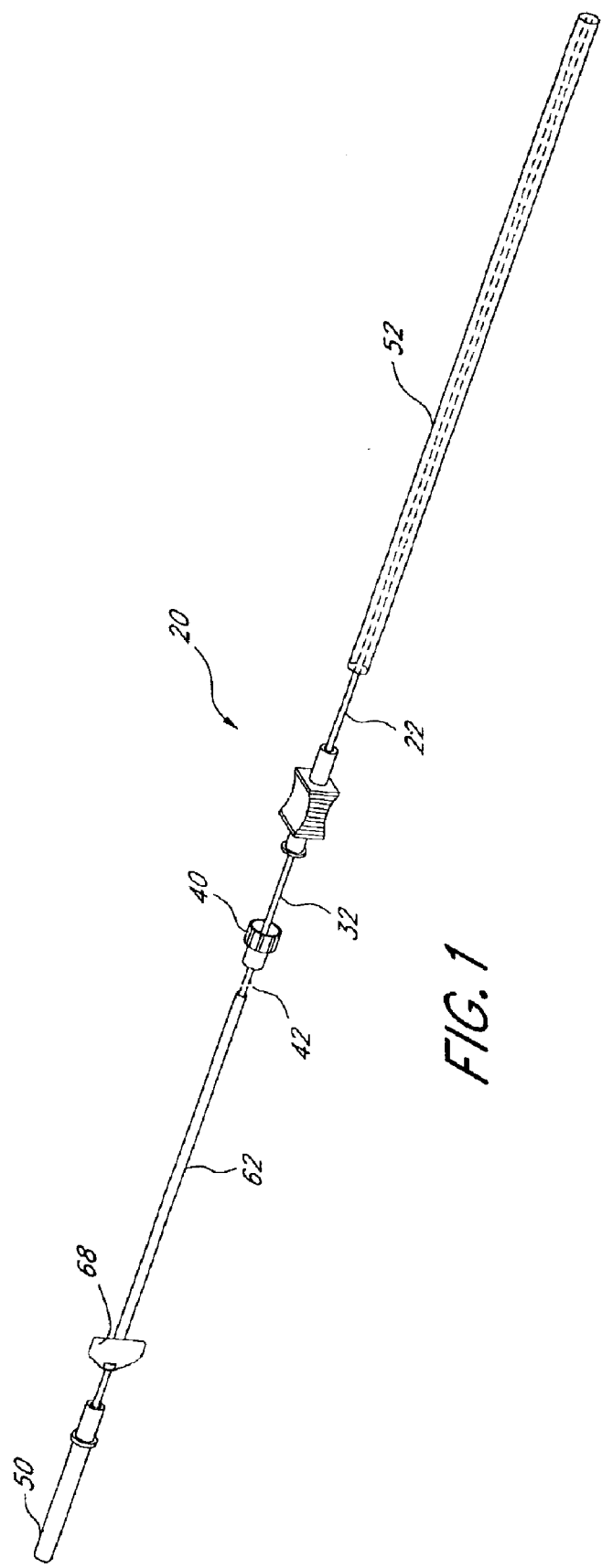

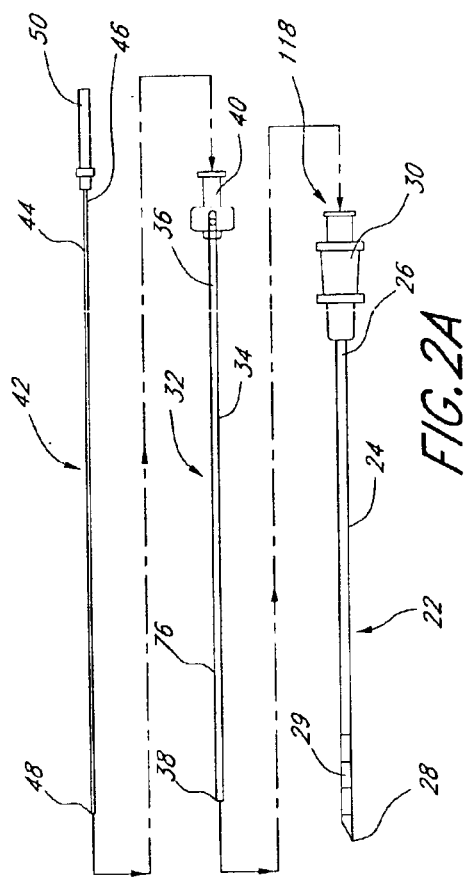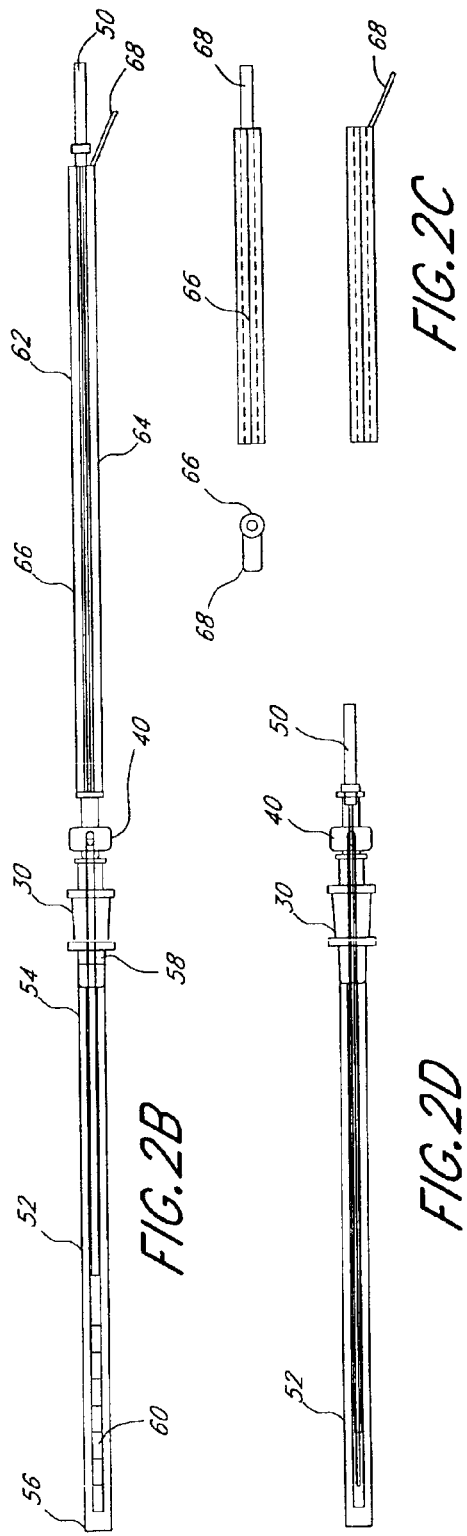

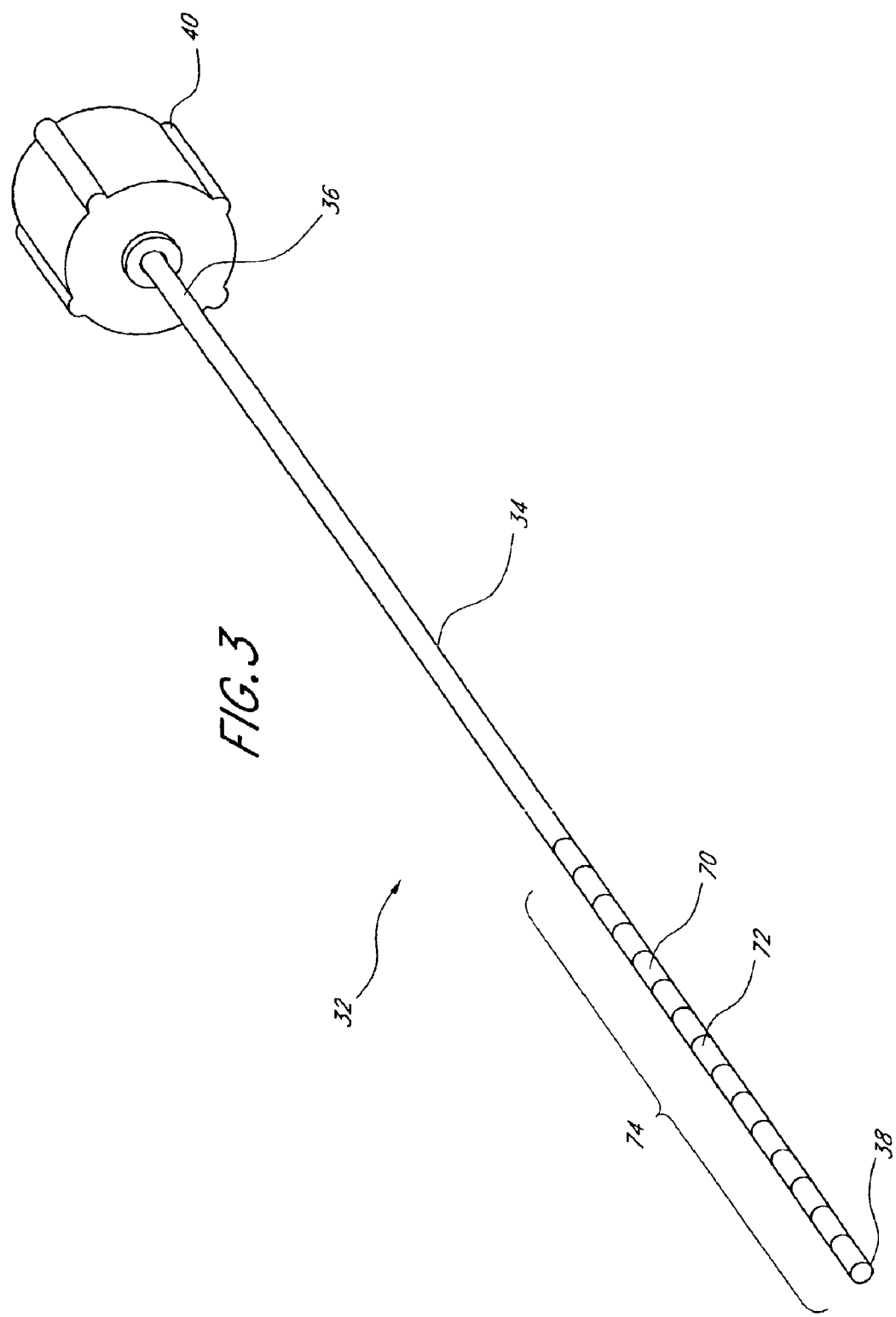

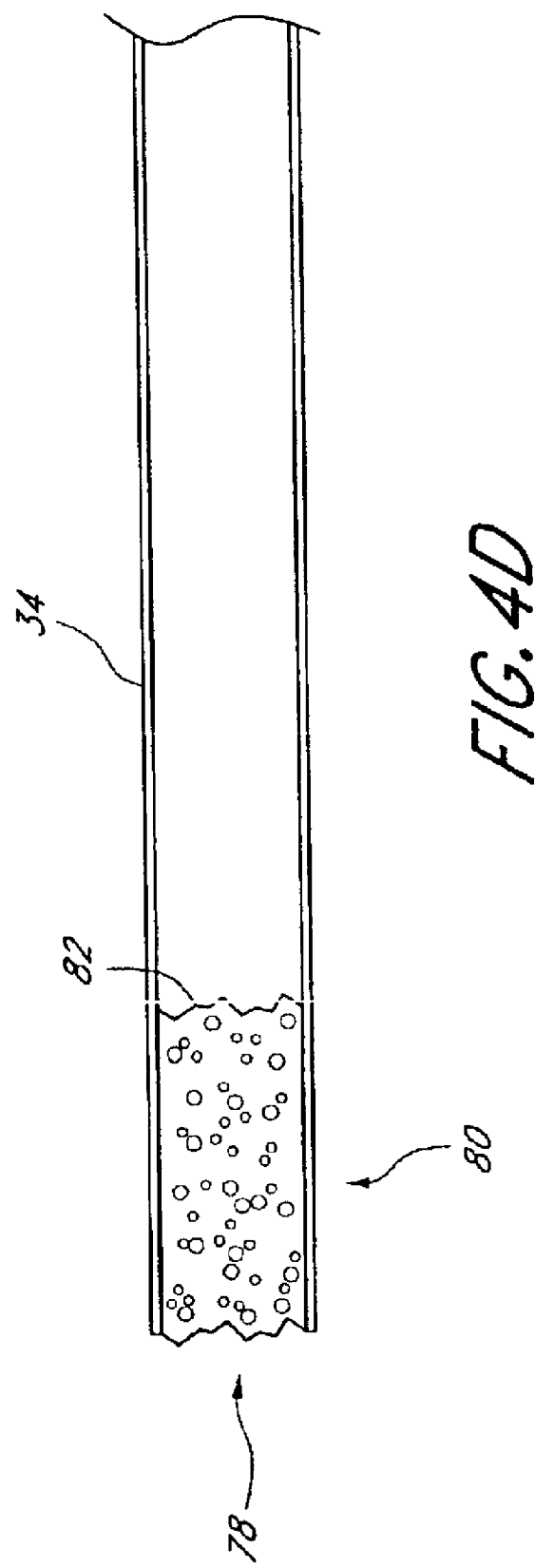

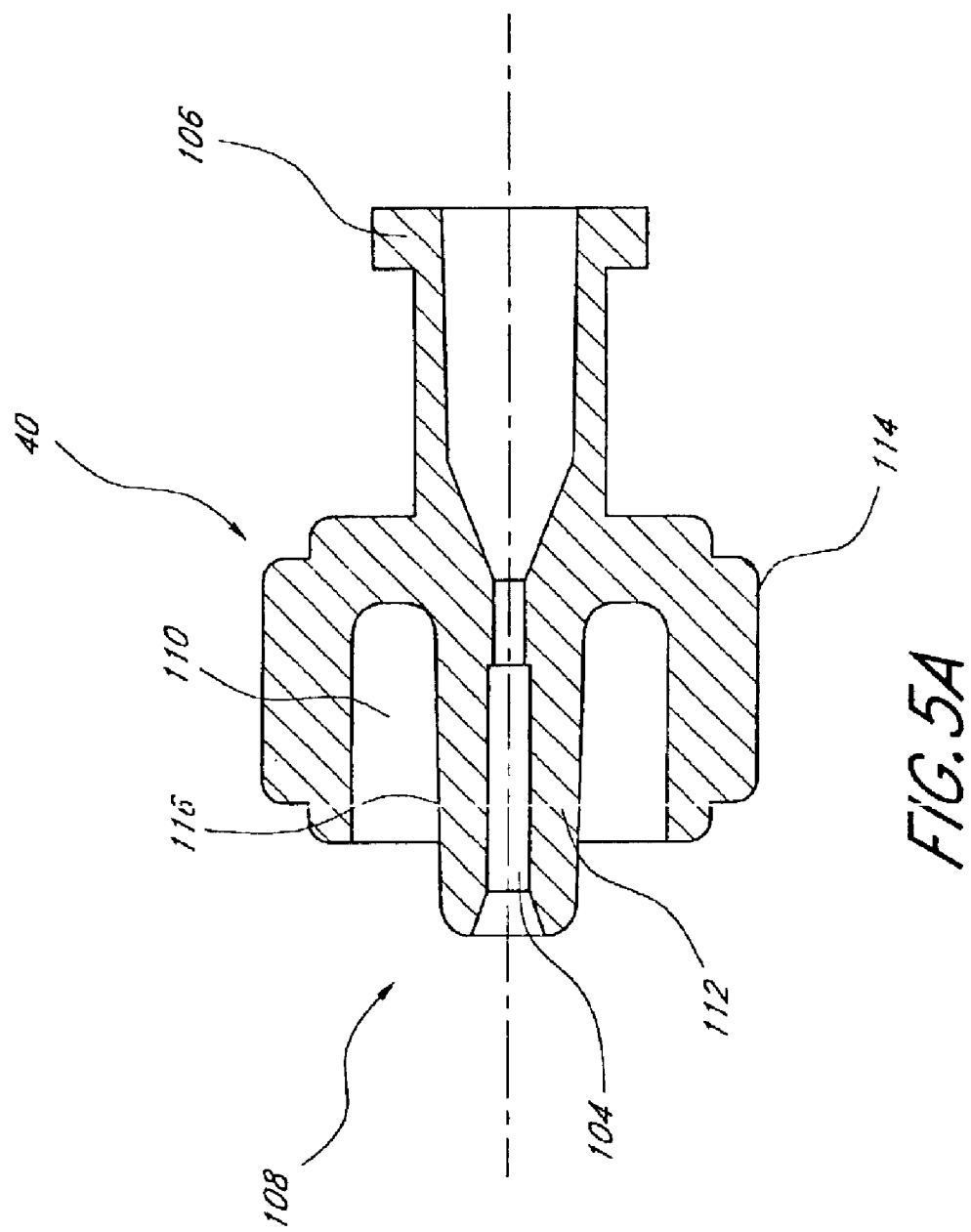

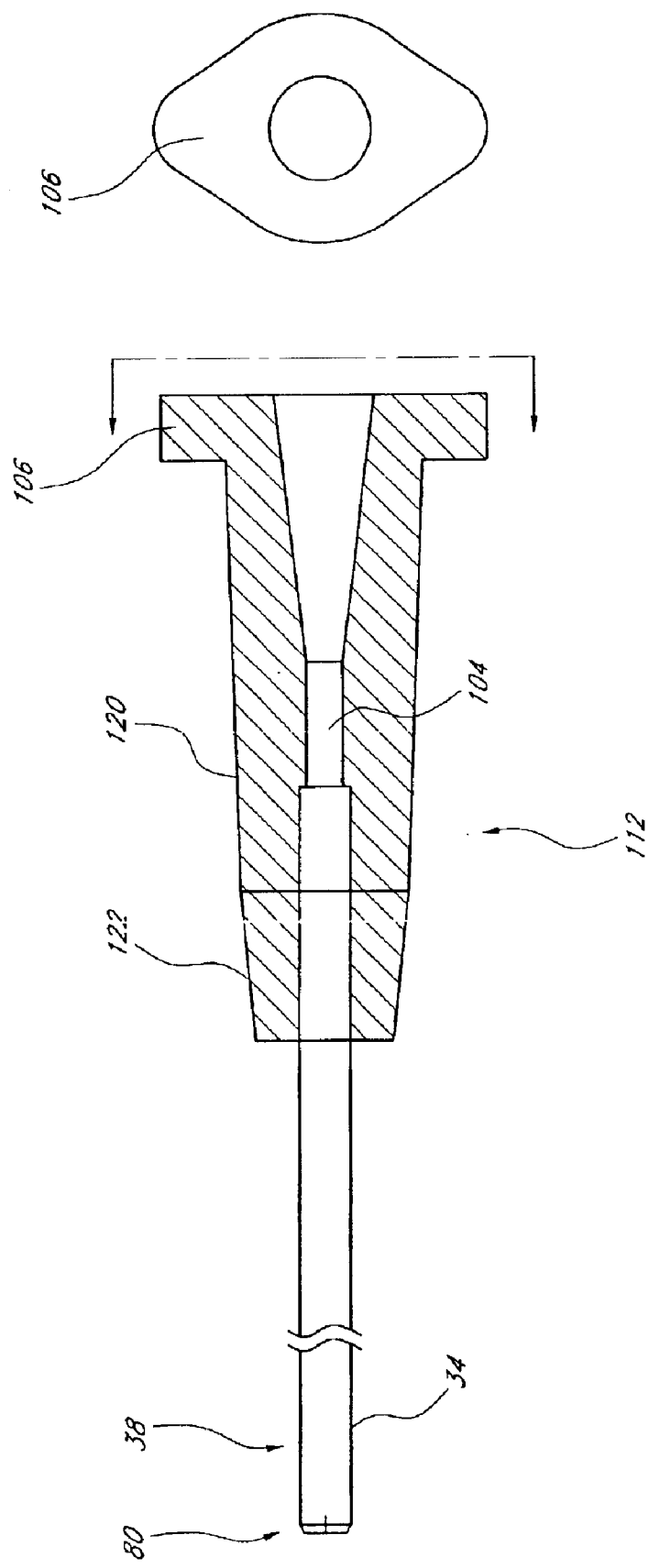

VariSeed: Needle Loading Report (Page 1)

VariSeed 6.7 (Build 1155) Seed Plan Pro 478-1 08/10/2000 10:31:52am

| Demo Studies, RRID #Demo | Study: Pre Operative Plan<br>Variation: Default<br>#Scars: 9<br>Template: B & K Standard | Isotope: I-125 (6711) 1999 c<br># Seeds: 92<br>Target Dose: 145.000<br>Anisotropic Correction: 0.930 | U/mCi: 1.270<br>U/Seed: 0.414<br>mCi/Seed: 0.326 |
|---|---|---|---|

| Needle Number | Retraction (cm) | Hole Location | Number Seeds |
|---|---|---|---|
| 1 | 0.00 | c4.0 | 5 |
| 2 | 0.00 | d4.0 | 5 |
| 3 | 0.50 | C3.5 | 4 |
| 4 | 0.50 | E3.5 | 4 |
| 5 | 0.00 | b3.0 | 5 |
| 6 | 0.00 | c3.0 | 2 |
| 7 | 0.00 | d3.0 | 2 |
| 8 | 0.00 | e3.0 | 5 |
| 9 | 0.50 | B2.5 | 3 |
| 10 | 0.50 | F2.5 | 3 |
| 11 | 1.00 | a2.0 | 2 |
| 12 | 0.00 | b2.0 | 5 |
| 13 | 0.00 | c2.0 | 5 |
| 14 | 0.00 | d2.0 | 5 |
| 15 | 0.00 | e2.0 | 5 |
| 16 | 1.00 | f2.0 | 2 |
| 17 | 0.50 | B1.5 | 3 |
| 18 | 0.50 | F1.5 | 3 |
| 19 | 1.00 | a1.0 | 2 |
| 20 | 0.00 | b1.0 | 5 |
| 21 | 0.00 | c1.0 | 5 |
| 22 | 0.00 | d1.0 | 5 |
| 23 | 0.00 | e1.0 | 5 |
| 24 | 1.00 | f1.0 | 2 |

● =Special loading

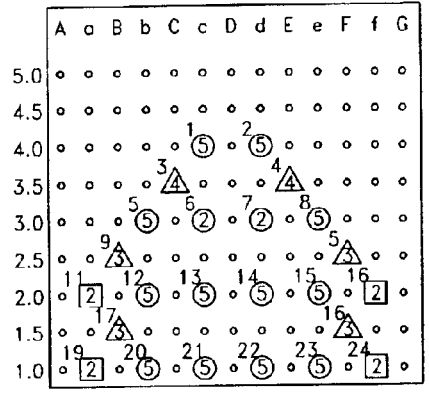

| Retraction Legend | | | | | |
|---|---|---|---|---|---|
| Plane 0 | Plane 1 | Plane 2 | Plane 3 | Plane 4 | special |
| 0.00cm | 0.50cm | 1.00cm | 1.50cm | 2.00cm | other |
| ○ | △ | □ | ◇ | ▽ | ⬡ |

| Number of Needles | Seeds per Needle |
|---|---|
| 6 | 2 |
| 4 | 3 |
| 2 | 4 |
| 12 | 5 |

| Plan Summary | |
|---|---|
| Total Activity [U] | 38.09 |
| Total Activity [mCi] | 29.99 |
| Total Needles | 24 |
| Total Seeds | 92 |
| Extra Seeds | |
| Total Seeds to Order | |

FIG. 7A

Study Created by _____

Study Approved by _____

VariSeed: Needle Loading Report (Page 1)
VariSeed 6.7 (Build 1155) Seed Plan Pro 478-1 08/10/2000 10:31:52am

| Demo Studies, RRID #Demo | Study: Pre Operative Plan  Variation: Default  #Scans: 9  Template: B & K Standard | | |
|---|---|---|---|
| Needle Number | Retraction (cm) | Hole Location | Number Seeds |
| 1 | 0.00 | c4.0 | 5 |
| 2 | 0.00 | d4.0 | 5 |
| 3 | 0.50 | C3.5 | 4 |
| 4 | 0.50 | E3.5 | 4 |
| 5 | 0.00 | b3.0 | 5 |
| ● 6 | 0.00 | c3.0 | 2 |
| ● 7 | 0.00 | d3.0 | 2 |
| 8 | 0.00 | e3.0 | 5 |
| 9 | 0.50 | B2.5 | 3 |
| 10 | 0.50 | F2.5 | 3 |
| 11 | 1.00 | a2.0 | 2 |
| 12 | 0.00 | b2.0 | 5 |
| 13 | 0.00 | c2.0 | 5 |
| 14 | 0.00 | d2.0 | 5 |
| 15 | 0.00 | e2.0 | 5 |
| 16 | 1.00 | f2.0 | 2 |
| 17 | 0.50 | B1.5 | 3 |
| 18 | 0.50 | F1.5 | 3 |
| 19 | 1.00 | a1.0 | 2 |
| 20 | 0.00 | b1.0 | 5 |
| 21 | 0.00 | c1.0 | 5 |
| 22 | 0.00 | d1.0 | 5 |
| 23 | 0.00 | e1.0 | 5 |
| 24 | 1.00 | f1.0 | 2 |
| ● =Special loading | | | |

FIG.7B₁

| FIG.7B₁ | FIG.7B₂ |
|---|---|

FIG.7B

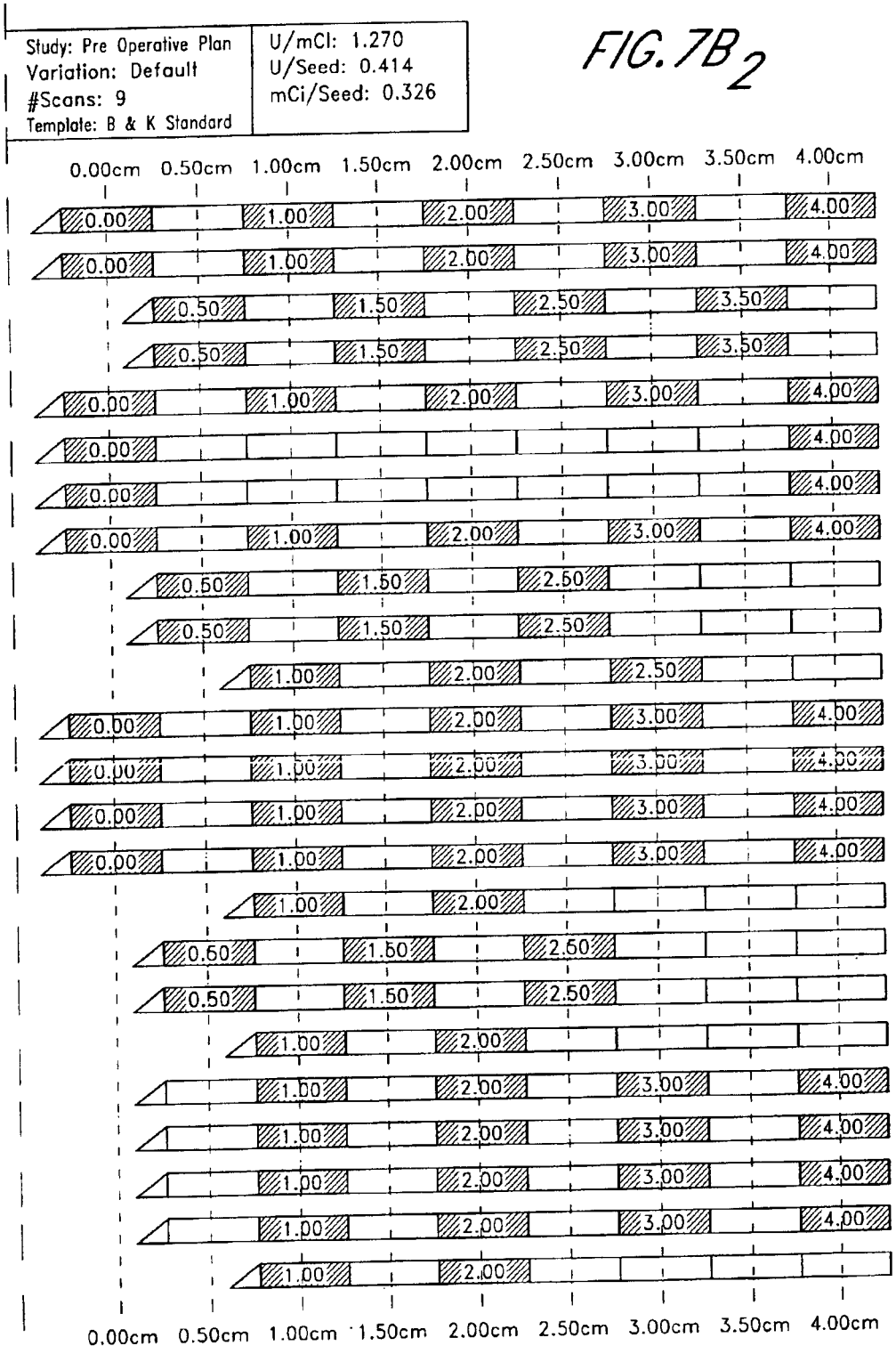
FIG. 7B₂

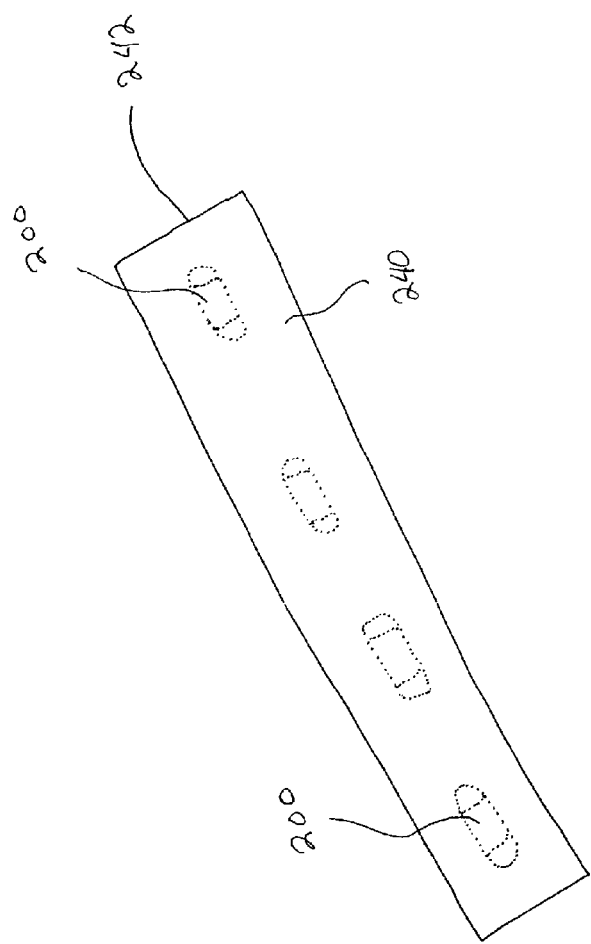

BRACHYTHERAPY SEED DEPLOYMENT SYSTEM

RELATED APPLICATION

This application is a continuation-in-part of U.S. patent application Ser. No. 09/694,107 filed Oct. 20, 2000 now U.S. Pat. No. 6,530,875, the disclosure of which is incorporated in its entirety herein by reference.

BACKGROUND OF THE INVENTION

This invention relates to the field of brachytherapy and the manufacture and handling of small radioactive seeds. Brachytherapy involves the implantation of small radioactive seeds, or pellets into tumors to eradicate cancerous cells, and is an alternative to external radiation therapy such as electron beam irradiation.

Brachytherapy has been used in the treatment of numerous types of cancer, including cervical, breast, lung, head and neck, and prostate. As an example of the procedure the treatment of prostate cancer will be used. This is in no way intended to limit the scope of this application, as the use of the invention disclosed herein has general application in the handling of the radioactive pellets, or seeds, as will be obvious to those skilled in the art.

The treatment of prostate cancer using radioactive seed implantation has been known for some time. Currently either Palladium-103 or Iodine-125 seeds are used, with apparent activities ranging from about 0.25 mcuries to 1.2 mcuries, depending on the prostate size and aggressiveness of the cancer. Recent advances in ultrasound imaging and other technological advancements have enabled this procedure to become a very viable alternative to other treatments such as external beam irradiation and radical prostatectomy. The procedure involves ultrasound mapping of the prostate gland and size of tumor using a transrectal ultrasound probe. A radiation oncologist will then decide on the number and positioning of the radioactive seeds needed to deliver a sufficient amount of radiation to kill the cancerous cells. The requisite number of radioactive seeds are typically loaded into 18 gauge brachytherapy needles. Needles may contain anywhere from one to seven seeds, usually separated by bio-absorbable spacers of catgut or other suitable suture material. To prevent the seeds and/or the spacers from falling out of the needle accidentally, the distal end of the needle, the tip, is plugged with a small amount of bone-wax. Bone-wax is a medical grade beeswax material. The seeds are prevented from falling out of the proximal or hub end of the needle by a blunt obturator, which is ultimately used to force the seeds from the 18 gauge needle once in position in the prostate. The needles are inserted into the prostate transperineally.

In a typical procedure the needles loaded with seeds are inserted into the prostate gland under the guidance of the ultrasound rectal probe. A metal grid, abutting the peritoneum, having X-Y coordinates is matched to a grid overlaid on the real-time ultrasound picture, so that the requisite number of seeds can be placed at each location in accordance with the mapping planes used by the radiation oncologist to optimize dose delivery. Once the tip of the needle is visualized in the correct location on the ultrasound screen, the needle is withdrawn over the obturator whilst maintaining the position of the obturator, such that a pattern of seeds and spacers is laid down as required. Typically about 85 seeds are placed during the procedure, but the number can be as high as about 140 or as low as about 40. Thus a typical procedure uses about 30 needles per patient.

Currently the seeds and the spacers are loaded into the needles by the radiation oncologist or radiation physicist by hand. This is a laborious task, and can take up to an hour to complete. This can tie-up Operating Room time, and at a minimum is wasting radiation oncologist or physicist time. Furthermore, during this time the person doing the loading is exposed to undesirable levels of radiation, and the loading task is extremely fatiguing. Some mechanical assist devices exist, but they are either unreliable, and can jam or, even worse, break or crush a seed allowing radioactive material to escape. In addition, verification of seed loading per needle is generally not readily accomplished. A system marketed by Northwest Radiation Therapy Products organizes the seeds, spacers, and needles on a stand. This lessens operator movement, but the process is still time consuming.

An alternate approach for delivering the seeds to the patient is typified by instruments called the Mick Applicator and the Quick Seeder Applicator sold by Mick Radio-Nuclear Instruments, Inc. In this system the empty needles are first inserted into the patient at the predetermined locations. Then using the Mick Applicator one seed at a time is delivered from a pre-loaded cartridge, indexing back a pre-determined distance after delivering each individual seed. In the case of the Quick Seeder Applicator, a cartridge pre-loaded with seeds and spacers is attached to the needle. This device transfers a column of seeds and spacers by indexing back a pre-determined distance to accomplish the delivery. Again the cartridges are loaded either by hand or by using a device that consists of a chamber in which the seeds and spacers are lined up before being pushed into the cartridge. This is time consuming because seeds and spacers still have to be hand loaded into the transfer chamber, thus offering little benefit over straight hand loading. The invention described herein overcomes the deficiencies in the prior art and provides an improved means for loading needles. No supplier provides pre-loaded needles for brachytherapy.

Another approach for delivering the seeds to the patient is typified by the RAPID Strand™ Rigid Absorbable Permanent Implant Device sold by Nycomed Amersham. This device consists of ten Iodine-125 seeds spaced at a fixed distance within a polyglactin 910 absorbable suture. The suture material containing the seeds is stiffened and then sterilized. RAPID Strand™ is implanted in the patient using standard implantation techniques and disposable needles. Disadvantageously, RAPID Strand™ frequently jams the implantation needle, requiring the implanting physician to discard the needle and seeds. Further, because RAPID Strand™ uses a bioabsorbable suture, once the body absorbs the suture, the seeds may migrate and not accomplish their intended purpose.

U.S. Pat. No. 5,928,130 by Schmidt describes a tool for implanting radioactive seeds that includes a needle, spacers and seeds loaded into a transparent or translucent sleeve, and an obturator to facilitate the displacement of spacers and seeds and deposit them into tissue.

Notwithstanding the various efforts in the prior art, there remains a need for a preloaded brachytherapy seed system as described in detail below.

Proper seed placement and seed retention at the implantation site strongly influence the success or failure of a brachytherapy procedure. As described above, seed implantation devices generally contain a plurality of seeds that may be separated by spacers. Prior implantation devices and methods do not reliably maintain proper seed spacing during and after implantation. Therefore, a device and/or method of reliably maintaining proper seed spacing during and after implantation would be of great benefit to brachytherapy patients.

Loose seeds, especially those that are extra-capsular (located outside the capsule of the prostate), tend to migrate within the patient. Because extra-capsular tissue is less dense than tissue within the capsule of the prostate, prior brachytherapy seed implantation devices and methods can not effectively maintain the location of seeds in the extra-capsular material. These seeds readily migrate and fail to provide radiation where needed. Migrating radioactive seeds not only fail to provide needed radiation therapy at the treatment site, but may cause damage to other radiation-sensitive areas of the body. Therefore, a device and/or method of preventing migration of radioactive seeds would be of great benefit to brachytherapy patients.

SUMMARY OF THE INVENTION

A preferred embodiment of the present brachytherapy seed deployment system comprises at least two seeds and a filament joining the at least two seeds. The seeds may be attached to the filament with, for example, adhesive or cylindrical collars. The coilars may be heat shrunk around the seeds. More than one filament may be provided. To maintain proper spacing between adjacent seeds, spacers may be positioned between the seeds. A distal end of the filament may include an anchor, such as a knot in the filament, a hook or a T bar. A distal seed may also include an anchor, such as a barb, instead of or in addition to the anchor on the filament. The filament may comprise a material that is rigid outside the human body and flexible inside the human body. For example, the filament may comprise a material that is rigid at temperatures below normal human body temperature and flexible at normal human body temperature. Alternatively, the filament may comprise a material including a matrix that is rigid outside the body and flexible within the body.

Another preferred embodiment of the present brachytherapy seed deployment system comprises at least two seeds, a filament joining the at least two seeds, a sleeve including a central lumen for containing the seeds and filament, and a needle including a central lumen for containing the sleeve. The system may further comprise an obturator insertable through a proximal end of the sleeve for ejecting the seeds and filament from the sleeve. The sleeve may further comprise a hub, and the needle may also further comprise a hub.

Another preferred embodiment of the present brachytherapy seed deployment system comprises a method of assembling a brachytherapy seed deployment system. The method comprises the steps of providing a fixture including a longitudinal slot, securing a filament within the slot, pulling the filament taut, sliding at least one cylindrical collar onto the filament, inserting a seed into the at least one collar, locating the seed and collar at a desired point along a length of the filament, and securing the seed and collar to the filament. The method may further comprise the step of securing an anchor to a distal end of the filament. The method may further comprise the step of providing a second filament. The first and second filaments may be located on opposite sides of the seed. The seed and collar may be secured to the filament by heat shrinking. The method may further comprise the step of inserting at least one spacer between adjacent seeds. The method may further comprise the step of knotting and cutting an end of the filament. The method may further comprise the step of placing the seed, collar and filament into a sleeve.

Another preferred embodiment of the present brachytherapy seed deployment system comprises a method of implanting brachytherapy seeds. The method comprises the steps of providing a needle, the needle containing a sleeve, the sleeve containing at least two seeds joined to one another by a filament, penetrating a cancerous region with the needle, and ejecting the seeds from the sleeve and implanting the seeds in the cancerous region. The seeds may be ejected from the sleeve by an obturator inserted through a proximal end of the sleeve. A distal end of the filament may include an attached anchor, such as a knot in the filament, a hook or a T bar. The optional anchor preferably engages tissue in the cancerous region. Preferably, as the needle and sleeve are withdrawn from the cancerous region, the anchored distal end of the filament creates tension in the filament, maintaining a desired spacing of the seeds. The distal seed may include a notch, such that a rigid wire is engageable with the notch to hold the distal seed in place in the cancerous region as the sleeve and needle are withdrawn.

Another preferred embodiment of the present brachytherapy seed deployment system comprises at least two seeds, and a laminate encapsulating the at least two seeds. The laminate may comprise at least two sheets of a biocompatible polymeric material. The system may further comprise at least one spacer between adjacent seeds.

Another preferred embodiment of the present brachytherapy seed deployment system comprises a method of securing at least two brachytherapy seeds to a filament. The method comprises the steps of providing a filament, securing a first seed to the filament, and securing a second seed to the filament such that the two seeds are tethered to one another by the filament. The seeds may be secured to the filament via an adhesive, or the seeds may be secured to the filament via a heat-shrunk collar. The method may further comprise the step of placing a spacer between the seeds. The spacer may be secured to the filament.

Further features and advantages of the present invention will become apparent to those of skill in the art in view of the detailed description of preferred embodiments which follows, when considered together with the attached drawings and claims.

BRIEF DESCRIPTION OF THE DRAWINGS

The novel features, advantages, and aspects of the present invention will be more readily understood upon reading the following detailed description taken in connection with the accompanying drawings in which:

FIG. 1 is a partially exploded perspective view of components of the invention;

FIG. 2A is a schematic exploded view of components of the invention;

FIG. 2B is a side elevational view of an assembled, loaded deployment device in accordance with the present invention;

FIG. 2C are schematic views of an obturator lock in accordance with the present invention;

FIG. 2D is a side elevational view as in FIG. 2B, without brachytherapy seeds and with the obturator fully distally advanced;

FIG. 3 is a front perspective view of a sleeve assembly pre-loaded with seeds and spacers;

FIGS. 4A, 4B, 4C and 4D are views of seed and spacer retaining elements;

FIG. 5A is a cross-sectional view of a sleeve hub;

FIG. 5B is a cross-sectional view of an alternate sleeve hub;

FIGS. 7A and 7B are a needle loading report;

FIG. 45 is a schematic view of another preferred device and method of implanting the present brachytherapy seed deployment system.

DETAILED DESCRIPTION OF PREFERRED EMBODIMENTS

Figure 4A:
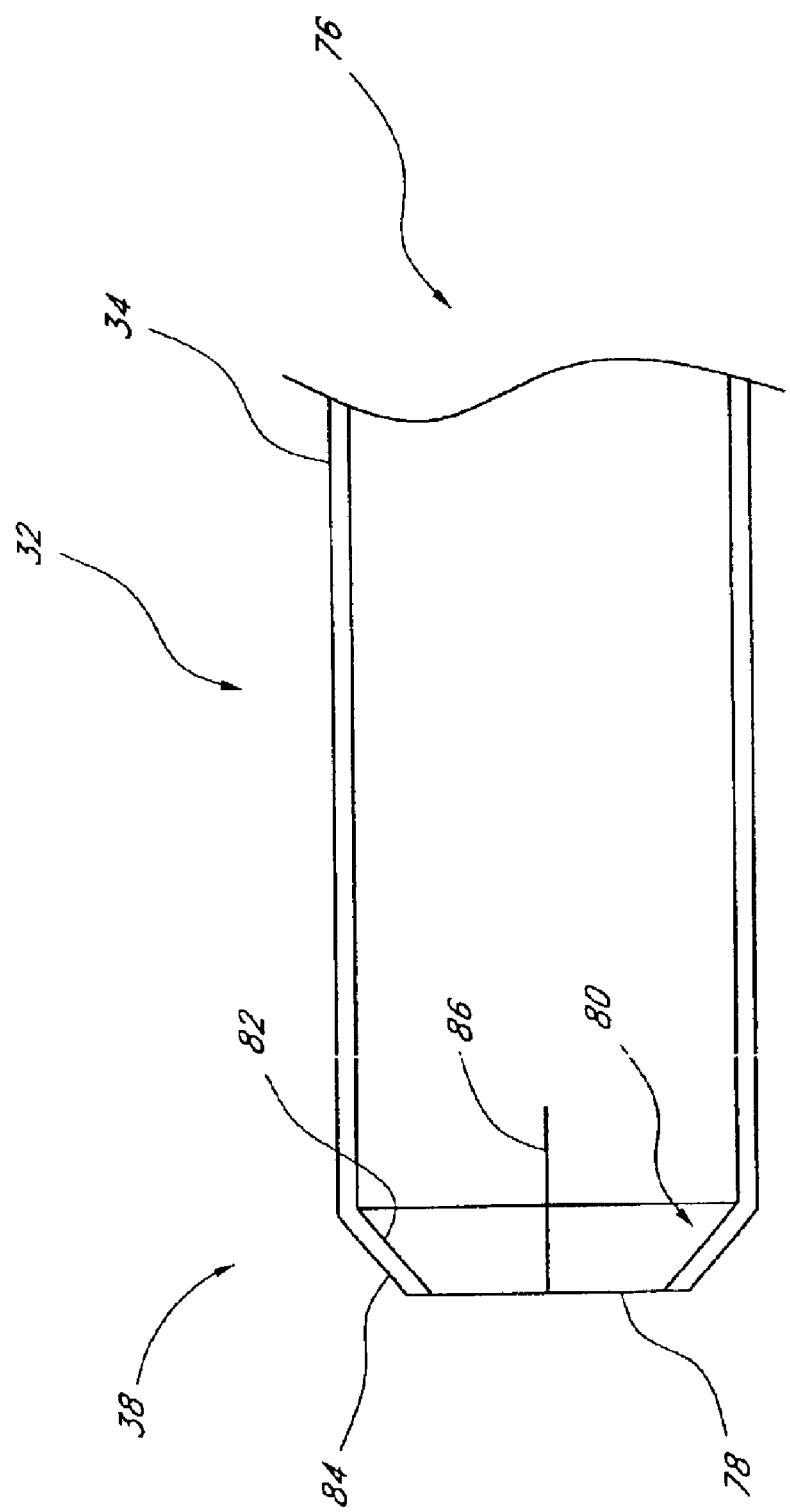

Referring to FIGS. 1 through 3, there is illustrated a brachytherapy seed deployment device 20 in accordance with one aspect of the present invention. The deployment device 20 is adapted to controllably deploy a plurality of radioactive seeds and spacers along a linear path in a target tissue site. Radioactive seeds and spacers may be individually deployed, with tactile feedback to the operator as each seed and spacer leaves the device. The risk of inadvertent deployment or loss of radioactive seeds or spacers is minimized or reduced by the distal tip design as will be discussed below.

The deployment device 20 comprises an elongate needle 22 for penetrating tissue to reach the target site as is known in the art. Needle 22 comprises an elongate tubular body 24 extending between a proximal end 26 and a sharpened distal tip 28 for puncturing tissue. See FIG. 2A. Proximal end 26 is provided with a Hub 30 as is understood in the art. In general, needle 22 has an axial length which is sufficient to reach the target tissue, from a predetermined access point. Thus, depending upon the target and access point, various needle lengths may be utilized. Axial lengths within the range from about 6 inches to about 12 inches and, in one embodiment, about 7.9 inches, are utilized in a system intended to treat the prostate gland.

Needles of various diameters may also be utilized, with an optimum diameter for any particular application selected to be sufficient to carry an appropriate seed while minimizing the cross-section of the puncture. In a system intended for treating the prostate gland, needles within the range from about 26 gauge to about 12 gauge, and, in one embodiment, 18 gauge, will normally be used. Needles made from any of a variety of materials including stainless steel, nitinol, or others may be utilized as will be understood in the art.

Tubular sleeve 32 is dimensioned to be axially slidably positioned within the needle 22. Sleeve 32 comprises an elongate tubular body 34, extending between a proximal end 36 and a distal end 38. Proximal end 36 is provided with a Hub 40. The distal end 38 of sleeve 32 is preferably provided with one or more brachytherapy seed retention structures, which will be disclosed in greater detail below.

Sleeve 32 is adapted to slidably receive one or more radioactive seeds for deployment at a tissue site. Generally, from one to about seven seeds, usually separated by bioabsorbable spacers of cat gut or other suitable material will be preloaded into the sleeve depending upon the particular clinical needs of the patient. The preloading process preferably occurs at the point of manufacture or at a loading station which is remote from the clinical site.

Tubular body 34 is preferably manufactured from a material which permits visual observation of the contents, so that the physician or other clinical staff may observe the number and location of seeds and spacers within the sleeve 32. Materials having sufficient structural integrity and transparency for this purpose can be readily determined through routine experimentation by those of skill in the art in view of the objectives recited herein. In one embodiment, intended for use with an 18 gauge needle, tubular body 34 comprises a polyimide extrusion having an outside diameter of about 0.039 inches, an inside diameter of about 0.036 inches and a wall thickness of about 0.0015 inches. The specific dimensions of the sleeve 32 will be determined to cooperate with the Needle 22 as will be apparent to those of skill in the art in view of the disclosure herein.

An obturator 42 is adapted to be axially slidably received within the sleeve 32. Obturator 42 comprises an elongate body 44 having a proximal end 46 and a distal end 48. A Hub or control 50 is provided at the proximal end 46. The body 44 may comprise either a solid rod or a tubular element. Solid rods or tubes of stainless steel or other medically acceptable metals may be utilized. Alternatively, extruded rod or tubing of a polymeric material may also be utilized.

In one embodiment, the body 44 comprises ABS plastic. The outside diameter of the body 44 is adapted to be slidably received within the sleeve 32. Thus, in a system adapted for use with an 18 gauge needle, and a sleeve 32 having an inside diameter of about 0.036 inches, the outside diameter of body 44 of Obturator 42 is about 0.032 inches.

The role of the obturator 42 is to distally advance the seeds 70 and spacers 72 from the distal end 38 of the sleeve 32. As a consequence, distal end 48 of obturator 42 is preferably blunt, and provided with as large a cross-sectional area as will be slidably accommodated within the sleeve 32. Slidability may be optimized by providing the distal end 48 with a slight chamfer or break to reduce snagging. The axial length of the obturator 42 is preferably sufficient that the distal end 48 will reach the distal end 38 of the sleeve 32 at or about the time the Hub 50 engages Hub 40. In this manner, the entire contents of the sleeve 32 may be deployed into the patient.

Referring to FIG. 2B, the foregoing elements are illustrated in a loaded and locked orientation, such as for shipping and handling. The sleeve 32 carries a deployable load 60 such as a plurality of radioactive seeds 70 and spacers 72. Sleeve 32 is positioned within Needle 22, and obturator 42 is advanced distally through the central lumen 76 of sleeve 32 to about the point of contact with the proximal end of the deployable load 60.

The loaded needle and sleeve assembly is coaxially positioned within an outer needle shield 52. Needle shield 52 preferably extends between a proximal end 54 and a distal end 56. The axial length of the needle shield 52 is preferably longer than the axial length of the Needle 22, to minimize the risk of needle sticks during handling. The proximal end 54 of needle shield 52 is preferably frictionally engaged with the Hub 30, such as at a distal tapered engagement surface 58. Needle shield 52 may be removed at the clinical site, to expose the distal tip 28 of the Needle 22 for insertion at the treatment site.

In one embodiment in which needle 22 extends approximately 7.9 inches distally of the hub 30, needle shield 52 has an axial length of about 8.25 inches. The inside diameter of the needle shield 52 is sufficient to slidably receive needle 22 axially therethrough. In one embodiment intended for use with an 18 gauge needle, the needle shield 52 has an inside diameter of about 0.16 inches and an outside diameter of about 0.20 inches. Needle shield 52 may be manufactured by any of a variety of techniques well known in the art, such as extrusion of any of a variety of polymers well known in the medical device arts.

The deployment device 20 is further illustrated with an obturator lock 62. See FIG. 2B. In the loaded configuration, the proximal end 46 of the obturator 42 is positioned proximally of the hub 40 of sleeve 32 by a distance which corresponds to the axial length of the deployable load 60. Distal advancement of the obturator hub 50 will deploy the deployable load 60 out of the distal end 38 of the sleeve and distal tip 28 of the needle 22. Premature advancement of the hub 50, such as during handling or positioning of the needle 22, may accidentally deploy a portion or all of the deployable load 60 prior to the time that the needle 22 is appropriately positioned at the treatment site. In many radiation treatments, particularly in the prostate gland, a large number of needles 22 will be loaded with unique patterns or numbers of radioactive seeds. As a consequence, inadvertent loss of radioactive seeds from the sleeve 32 can significantly complicate and delay the procedure while the unique pattern of seeds and spacers for that needle is reconstructed. In addition, the possibility of accidental deployment of radioactive seeds in the operating room is disadvantageous to the clinical staff.

The present invention thus provides a lock for resisting distal advancement of the obturator 42 until the desired deployment time. Lock 62 thus axially fixes the position of the obrurator 42 with respect to the hub 30, until the lock is released. This lock may be accomplished using any of a variety of structures, such as Toohey-Borst type hubs, clamps, cams or other friction generating structures at about the hub 30. Alternatively, as illustrated in FIG. 2B, the obturator lock 62 comprises an elongate axial support, such as a tubular body 64, which is dimensioned to extend coaxially around the obturator 42, but not around the hub 30 or hub 50. In this manner, hub 50 cannot be advanced distally towards hub 30 until the obturator lock 62 has been removed. Obturator lock 62 in the illustrated embodiment comprises a tubular body 64 having an axially extending longitudinal slit 66 to allow the obturator lock 62 to be advanced laterally onto and removed from the obturator 42. A pull tab 68 may be provided on the tubular body 64, preferably centered approximately 180° apart from the longitudinal slit 66. The pull tab 68 may be pulled away from the obturator 42, thereby causing the tubular body 64 to be peeled away from the obturator 42. This low profile, low cost locking structure enables the positioning of the brachytherapy seed deployment device 20 at the treatment site, and then rapid removal of the obturator lock 62 by pulling pull tab 68 when the time is appropriate to deploy the deployable load 60.

Although the present invention is described primarily herein in the context of the radiation delivery device, it will be understood by those of skill in the art that the deployable load 60 may comprise any of a variety of devices, structures, or materials that may desirably be implanted within the body. For example, any of a wide variety of medications may be included within the sleeve 32. Drugs in solid or liquid form, time release structures, such as microporous materials or gels, or prosthetic devices may alternatively be deployed from the system disclosed herein.

Referring to FIG. 2D, the deployment system of FIG. 2B is illustrated, with the obturator lock 62 removed, and the obturator hub 50 advanced to its distal limit of travel in contact with the hub 40.

The obturator lock 62 may be manufactured in any of a variety of ways, which are known in the art. For example, obturator lock 62 may be extruded in tubular form, with the longitudinal slit 66 and tab 68 formed as a post-extrusion step. Materials such as various densities of polyethylene, polyethylene terephthalate, nylon, PEBAX, or others well known in the catheter and medical device arts may be utilized. In one embodiment, the obturator lock 62 comprises an extruded polypropylene tube having an inside diameter of about 0.06 inches, an outside diameter of about 0.09 inches, and an axial length of about 3.3 inches.

Preferably, the needle 22 is provided with markings along its axial length to allow visual observation of the depth of penetration at the treatment site. In addition, a distal zone 29 is preferably provided with a textured surface or radiopaque coating to enhance visualization as will be understood in the art.

Referring to FIG. 3, the tubular body 34 is illustrated with a load of seeds 70 and spacers 72. The seeds 70 and spacers 72 together define a deployable load length 74. The length 74 will vary depending upon the clinical needs of the patient. In general, load lengths within the range of from about 0.30 inches to about 3.31 inches are utilized in most applications where the device is utilized to deliver radioactive seeds to the prostate gland.

Referring to FIG. 4A, there is disclosed an enlarged distal end 38 of sleeve 32 including a seed retention structure to prevent inadvertent loss of seeds from the sleeve 32. Central lumen 76 within sleeve 32 is in communication with a distal opening 78, for deploying radioactive seeds and spacers or other material. At least one retention structure 80 is provided, for resisting accidental distal loss of the radioactive seeds 70 or spacers 72. In the illustrated embodiment, the retention structure 80 comprises one or more interference surfaces 82. Interference surfaces 82 are movably positioned at least part way across the path of the load to retain the load within the central lumen 76. The interference surface 82 is movable so that it can be advanced from a first position in which it obstructs the load to a second position in which the load may be distally deployed through the distal opening 78. Preferably, the interference surface 82 is biased in the direction of the first position.

In this manner, a seed may be forcibly advanced through the distal opening 78 by pushing the interference surface 82 out of the way. Once the seed has been deployed from the distal opening 78, the interference surface 82 returns to its first position, thereby providing tactile feedback to the clinician that the seed has been deployed and resisting accidental deployment of subsequent radioactive seeds or spacers.

The interference surface 82 may be provided on any of a variety of structures, such as radially inwardly extending tabs, flanges, tapered surfaces, inserts or other interference elements, as will be apparent to those of skill in the art in view of the disclosure herein. The interference surface 82 may be integrally formed with the sleeve 32, or may be manufactured separately and attached to the tubular body 34 during the manufacture process.

In the illustrated embodiment, the interference surface 82 is provided on the radially inwardly facing surface of an inclined flange 84. The illustrate flange 84 is in the form of an annular frusto-conical tip on the tubular body 34, inclining radially inwardly in the distal direction. Preferably, one or more axially extending slots 86 extend from the distal limit of the inclined flange 84, in a proximal direction, to facilitate the enlargement of the distal opening 78 when the clinician puts sufficient distal pressure on the obturator hub 50 to deploy a seed or spacer.

The interference surface 82, whether carried by inclined flange 84 or other structure, can extend circumferentially either entirely around or only part way around the distal opening 78. For example, in the embodiment illustrated in FIG. 4A, the inclined flange 84 extends substantially the entire circumference of the distal opening 78. Alternatively, inclined flange 84 may extend no more than about 180°, no more than about 90°, or even no more than about 10° or 15° of the circumference of distal opening 78. The foregoing circumferential lengths of inclined flange 84 may represent a single continuous flange, or the sum of a plurality of distally inclined tabs. For example, by removing portions of the flange, a plurality of spaced apart tabs may be provided such as two or four or six or more tabs, spaced apart around the circumference of distal opening 78. The number and spacing of these tabs can be selected to achieve a desired minimum deployment force and tactile feedback as will be apparent to those of skill in the art in view of the disclosure therein.

The illustrated inclined flange 84 can be manufactured in any of a variety of ways, depending in part upon the material of tubular body 34. For example, molding, machining, or attachment of a separately formed tip such as with adhesives, thermal bonding or other technique may be used. In one embodiment, the flange 84 is formed in a polyimide tubular body 34 by advancing the tube into a frusto-conical bore with a corresponding mandrel positioned within central lumen 76, under the application of heat.

Figure 4B:
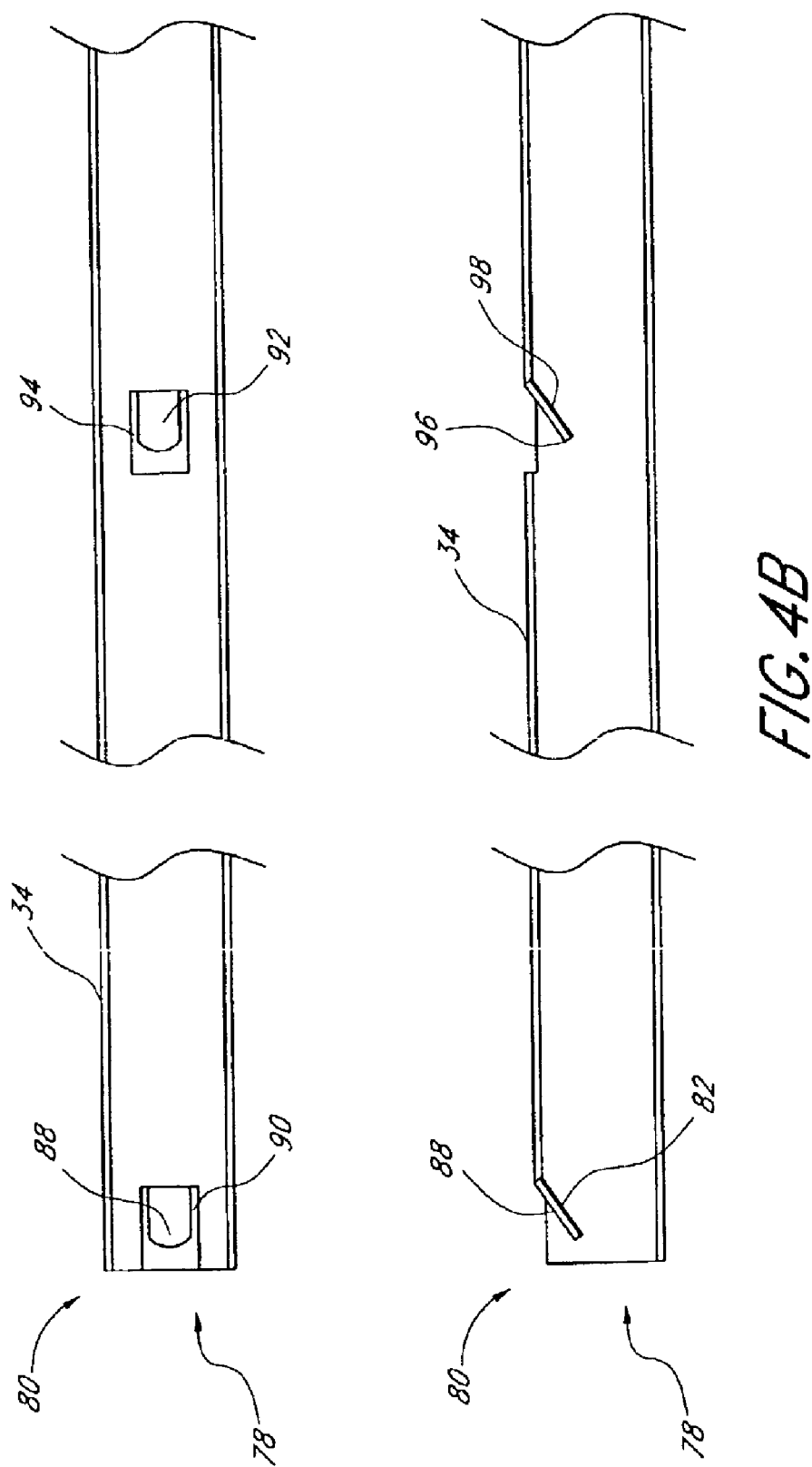

An alternate retention structure 80 is illustrated in FIG. 4B. An inclined tab 88 is created by forming a slot 90 in a generally U-shaped configuration, or by forming two parallel slots 90 at the distal end of the tubular body 34. The resulting tab 88 may then be bent radially inwardly to provide an interference surface 82 in the path of the brachytherapy seed. One or two or more inclined tabs 88 may be provided in a common plane transverse to the longitudinal axis of the tube 34, depending upon the desired performance characteristics of the device.

A similar structure may be provided at the proximal end of the deployable load 60, if desired, to prevent proximal loss or travel of seeds 70 or spacers 72. The proximal stop 92 may be formed by a slot 94 in the wall of the tubular body 34, such as in a U- or V-shape. The resulting proximal stop 92 may be bent radially inwardly to provide a ramp 98 and a stop surface 96. As will be apparent to those of skill in the art, ramp 98 allows distal advancement of seeds through the central lumen 78 but proximal travel of seeds will be prevented by stop surface 96.

The provision of a proximal stop 92 is optional, and may be desirable in embodiments in which shipping of loaded sleeves is accomplished without an obturator 42 positioned within the tubular body 34 proximally of the deployable load 60.

Figure 4C:
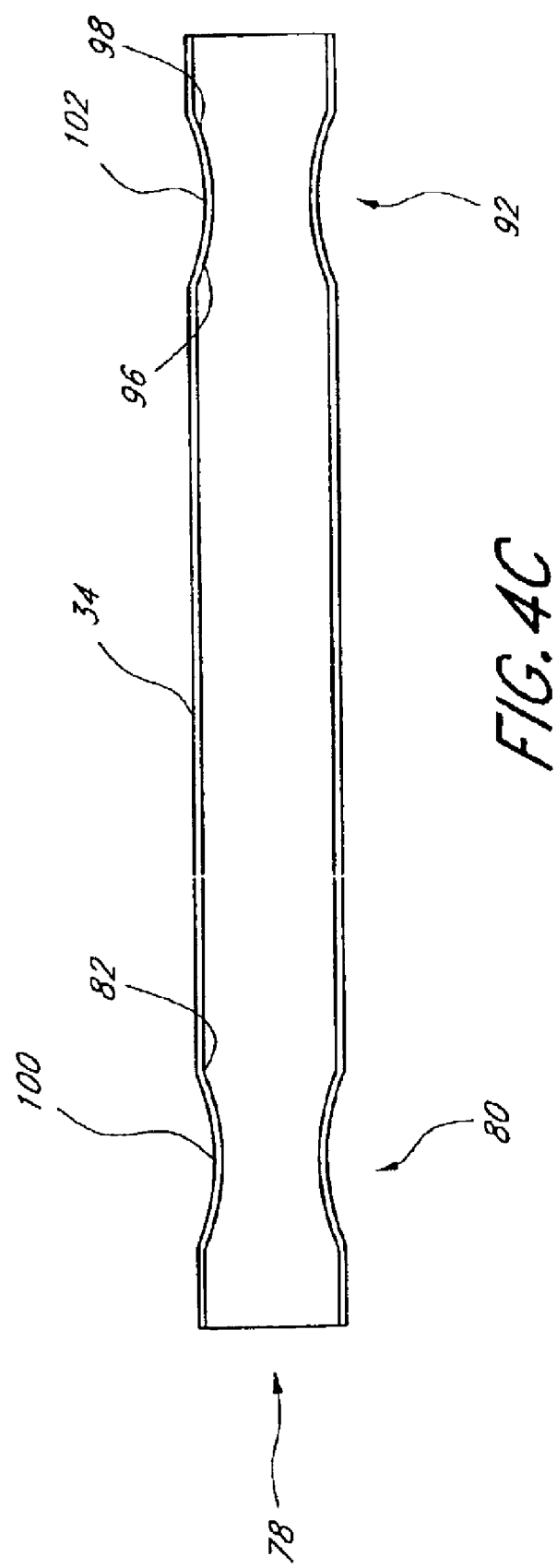

Referring to FIG. 4C, there is illustrated an alternate retention structure 80 and optional proximal stop 92. Retention structure 80 is formed by a crimp or dent 100 in the wall 34 of tubular body 32. The crimp 100 provides an interference surface 82, which interferes with the distal travel of a brachytherapy seed 70 or spacer 72. Upon application of sufficient distal force on the brachytherapy seed 70, the interference surface 82 is pushed out of the path of travel such that the seed 70 is deployed through the distal opening 78. Crimp 100 may be in the form of an annular indentation, or one or more discrete indentations or dents around the circumference of the tubular body 34. For example, two opposing crimps may be provided or three crimps provided with 120° spacing, or four crimps at 90° spacing around the circumference of the tubular body 34. The precise location, depth, and number of crimps 100 may be determined through routine experimentation, depending upon the desired performance of the device.

Similarly, the optimal proximal step 92 is provided by one or more crimps or dents 102. The resulting structure provides a ramp 98 to permit distal travel of radioactive seeds 70 under distal pressure by an obturator or other loading device. The stop surface 96 inhibits proximal travel of the seeds or spacers.

The crimp 100 or 102 may be provided in any of a variety of manners depending upon the construction materials and wall thickness of the tubular body 34. For example, certain materials may retain a crimp provided by controlled mechanical compression of the tubular body 34. The compression may be accomplished with or without the application of heat, depending on the material and wall thickness. In one embodiment in which the tubular body 34 comprises a polyimide extrusion, the crimp 100 and, optionally, crimp 102 is provided by compressing the wall 34 at an elevated temperature within the range of from about 600° F. to about 800° F.

An alternate retention technique is schematically illustrated in FIG. 4D. In this embodiment, the distal opening 78 is obstructed by a removable plug such as a wax or gel. Suitable materials for the plug include medical grade bonewax, available from medical goods suppliers. Care should be taken to ensure consistent needle to needle plug size, so that the seeds may be precisely placed at the treatment site.

Referring to FIG. 5A, there is illustrated a cross-sectional view through a sleeve hub 40, for connecting to the proximal end 36 of sleeve 32. In general, sleeve hub 40 comprises a proximal connector 106 such as a standard luer connector or a simple annular flange. The distal end 108 of sleeve hub 40 is provided with a lumen or bore 104 for receiving the proximal end 36 of sleeve 32. Sleeve 32 is preferably advanced into lumen 104 during the manufacturing process and secured in any of a variety of ways such as through the use of adhesives, solvent bonding, thermal bonding, or other techniques known in the medical device manufacturing arts.

A proximally extending annular recess 110 defines a distal projection or nose 112, which may serve as the male component of a luer connector. For this purpose, the wall of annular recess 110 may be provided with radially inwardly directed threads as are well understood in the art. In this manner, the hub 40 may be advanced distally toward and connected to the hub 30 by a partial rotation of hub 40 with respect to hub 30. A gripping surface 114 may be provided on the hub 40, including friction enhancing surface structures such as a plurality of axially extending ribs as is understood in the art. Preferably, the hub 40 is in the form of a male luer connector which may be securely engaged with a complementary female luer connector on hub 30 of the needle 22. In particular, the projection 112 is provided with a tapered surface 116, which fits within a complimentary tapered surface 118 surrounding a cavity in the proximal end of hub 30.

Brachytherapy needles 22 are currently marketed by more than one manufacturer, and complete uniformity in the design of hub 30 has not been achieved. The taper angle on interior surface 118 on the needle hub 30 is not uniform for all manufacturers. For example, some needles 22 are available having a taper on surface 118 of about 6 degrees, while other commonly available commercial needles 22 have a taper angle on surface 118 of about 2 degrees. If the taper angle on surface 118 does not correspond closely to the taper angle on surface 116, a secure fit between the needle 22 and sleeve 32 will not be achieved.

Accordingly, referring to FIG. 5B, there is provided in accordance with another aspect of the present invention a universal hub 40 for attachment to the proximal end 36 of tubular body 34. The projection 112 is provided with a first taper zone 120 having a first taper angle, and a second, distal taper zone 122 having a second, greater taper angle. The projection 112 on hub 40 can thus accommodate needle hubs 30 of differing internal tapers on surface 118. In one embodiment, the tapered surface 120 extends at an angle of approximately 2 degrees with respect to the longitudinal axis of tubular body 34, and tapered surface 122 resides at an angle of approximately 6 degrees with respect to the longitudinal axis of tubular body 34. Alternative tapers may readily be selected, depending upon the construction of the corresponding needle hubs which are desirably accommodated. In addition, three or more distinct taper surfaces may be provided on projection 112, if desired to accommodate a larger number of corresponding needle hubs.

Figure 6:
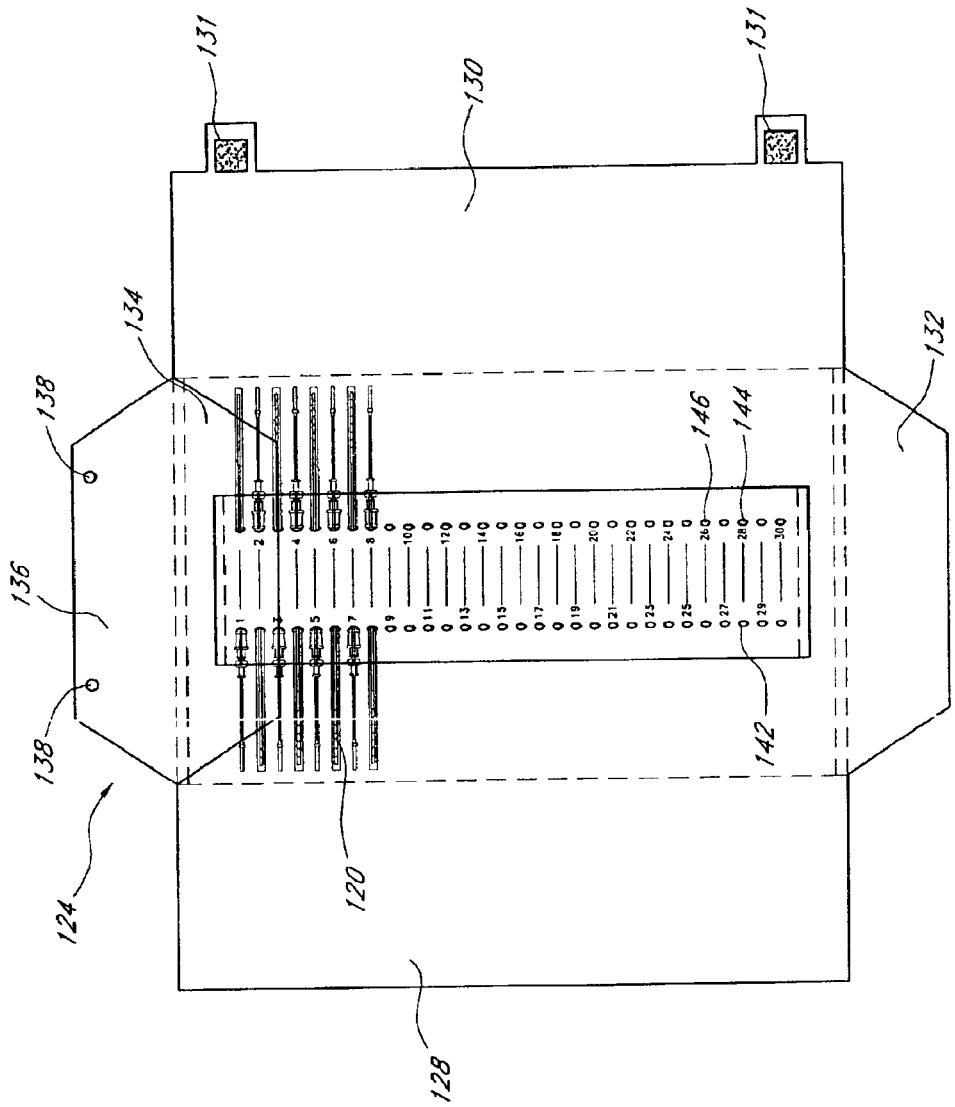
FIG. 6 is a schematic view of needles, pre-loaded sleeves, and obturators organized on a needle drape.

Referring to FIG. 6, there is illustrated a schematic plan view of a drape 124 in accordance with the present invention, adapted to carry a plurality of brachytherapy seed deployment devices 20. The drape 124 comprises a back portion 126, a left flap 128 and a right flap 130 for folding over the brachytherapy seed deployment devices 20. Alternatively, a single flap may be utilized to cover the entire front surface of the drape 124. The right flap 130 in the illustrated embodiment is provided with at least one removable attachment structure such as an adhesive patch 131. Adhesive patch 131 may be removably attached to the back surface of left flap 128 to releasably close the drape 124.

The illustrated drape 124 is additionally provided with a bottom flap 132 and a top flap 134. A support 136 is preferably provided with one or more attachment structures such as apertures 138, for attaching the drape 124 to a support structure as will be described.

The drape 124 is preferably additionally provided with a needle carrier 140. In the illustrated embodiment, needle carrier 140 is secured to the back 126, such that it will be covered by the closed right and left flaps 130 and 128. Needle carrier 140 is provided with a plurality of pairs of opposing apertures such as 142 and 144 adapted to receive a brachytherapy seed deployment device 20 therethrough. Although 30 opposing pairs of apertures are illustrated in FIG. 6, the capacity of the needle carrier 140 may be varied as desired. Preferably, each opposing pair of apertures 142 and 144 is provided with an identifying indicium 146 such as a letter or number to allow identification of each unique deployment device 20.

The drape 124 may be manufactured in any of a variety of ways, such as by cutting a desired profile on a polymeric sheet comprising any of a variety of medical grade, sterilizable materials. Suitable materials include polypropylene. In one embodiment, the back portion 126 has a vertical dimension of about 18 inches and a horizontal dimension of about 14.5 inches. The width in the horizontal direction of each of the left flap 128 and right flap 130 from the fold to the outer edge is approximately 7.75 inches. The needle carrier 140 comprises polypropylene, and is heat sealed at the top and bottom edges to the back 126. The back portion 126 or other portion of the drape 124 may optionally be additionally provided with a radiation attenuation layer such as a thin lead sheet to contribute to the radiation attenuation function of the needle pig 152 as will be discussed.

FIGS. 7A and 7B illustrate pages 1 and 2 of a needle loading report, which will accompany the loaded drape 124. On page 1 of the needle loading report illustrated at FIG. 7A, the spatial orientation of each needle at the treatment site is identified, as well as the number of radioactive seeds per needle. Page 2 of the needle loading report illustrated at FIG. 7B discloses the precise seed and spacer arrangement for each needle contained in the drape 124. Additional patient information is also included. In accordance with the present invention, each of the needles is preloaded at the point of manufacture for a unique patient's needs, and delivered to the treatment site. The clinical staff receive the loaded drape 124 and corresponding needle report, which enables them to both identify the precise desired location of each needle as well as audit the contents of each needle compared to the desired needle loading report, due to the transparent wall of the tubular sleeve 32.

Figure 8:
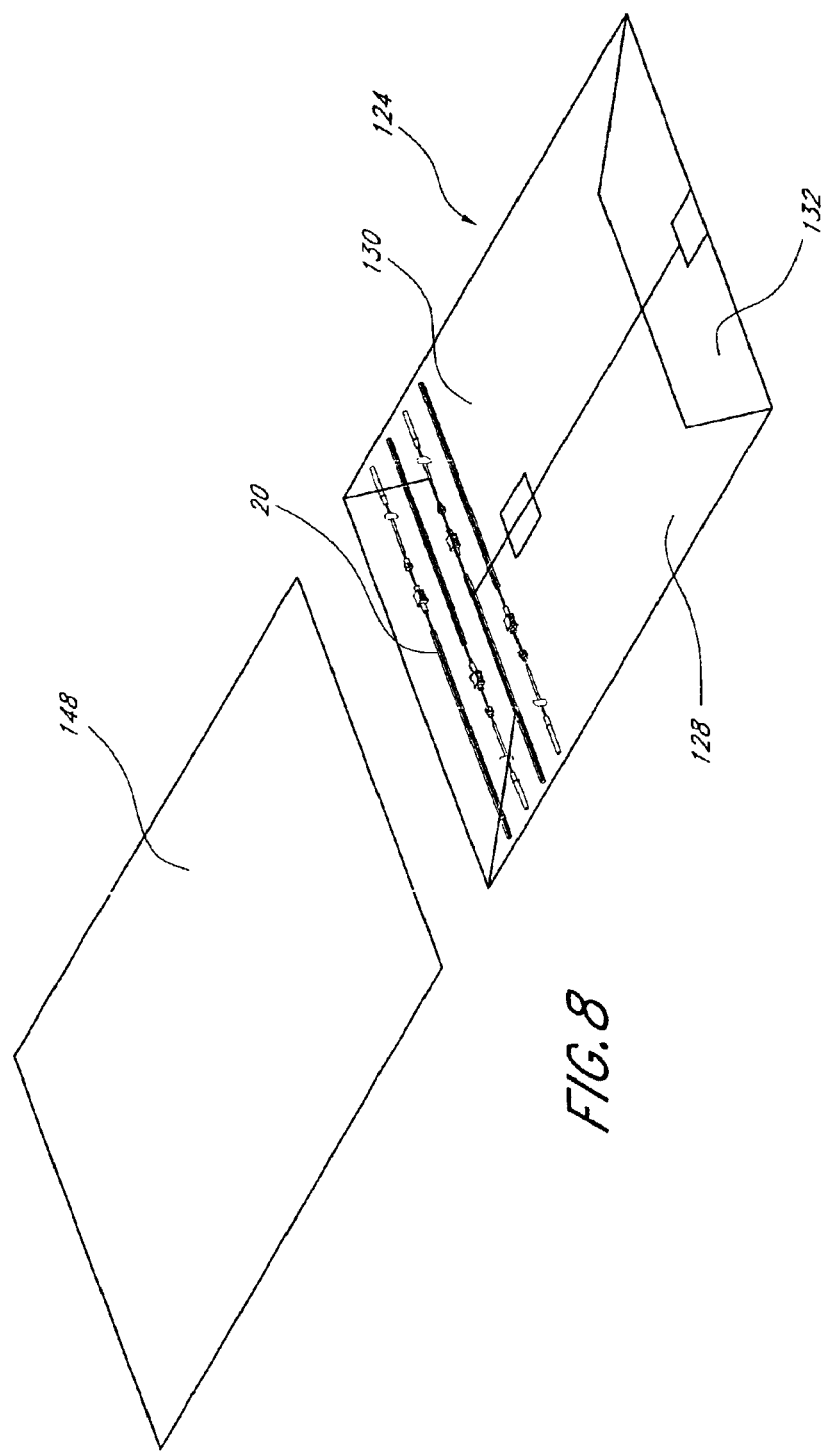
FIG. 8 is an exploded perspective view of a folded needle drape, and an outer pouch.

FIG. 8 illustrates a needle drape 124 including four brachytherapy seed deployment devices 20, in which the left flap 128, right flap 130, and bottom flap 132 are folded closed. For shipping, the entire folded needle drape is positioned within a sterile pouch 148.

Figure 9:
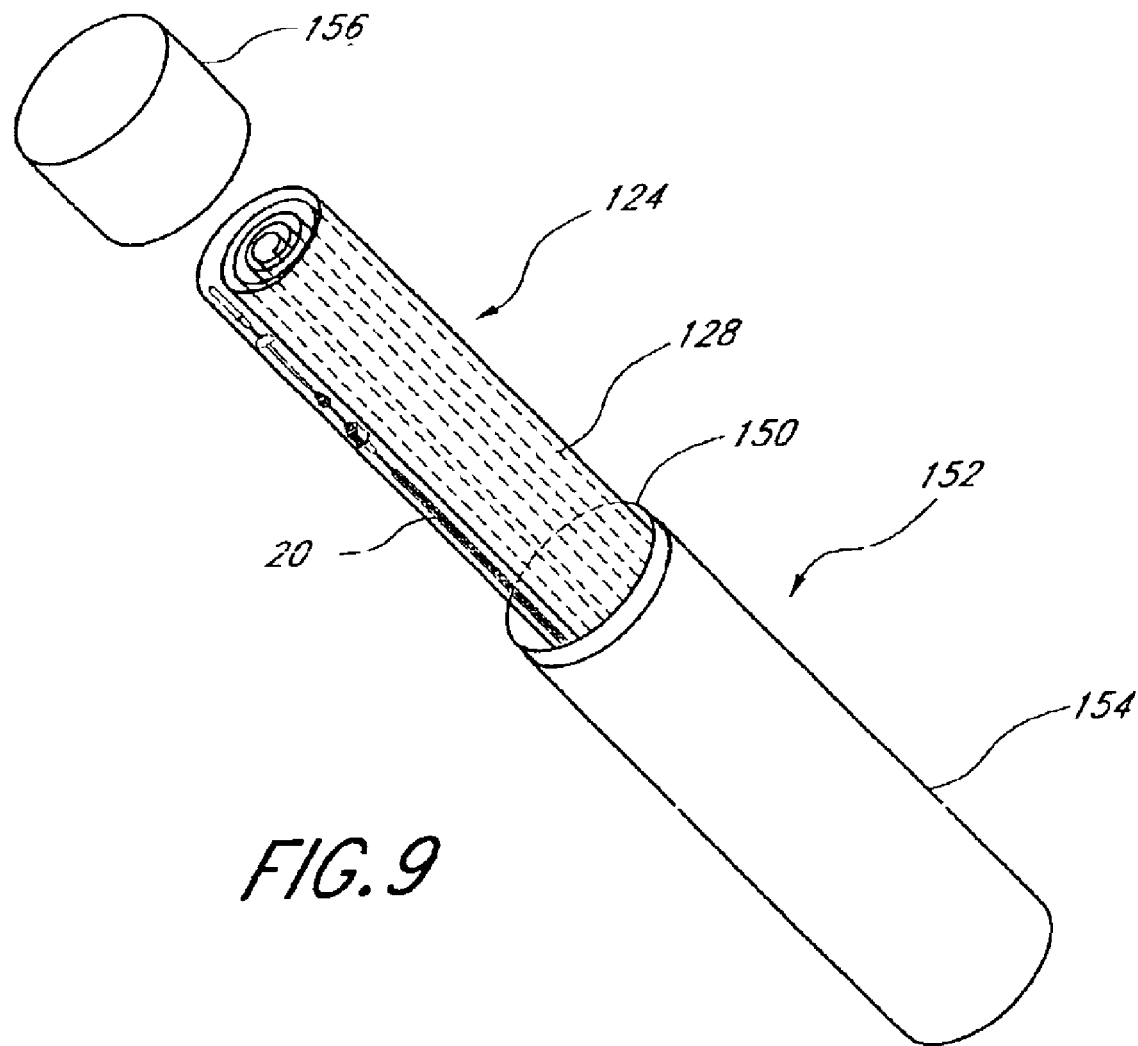
FIG. 9 is a partially exploded perspective view of a needle drape, pouch, needle canister lid and needle canister base.

Referring to FIG. 9, the pouch 148 containing the needle drape 124 is rolled following the loading process and positioned within a chamber 150 in a needle pig 152. The needle pig 152 comprises a needle canister base 154 having the chamber 150 therein, together with a corresponding needle canister lid 156. Preferably, the needle canister base 154 and lid 156 are made from lead, or other material which helps attenuate radiation from the brachytherapy seeds.

Figure 10:
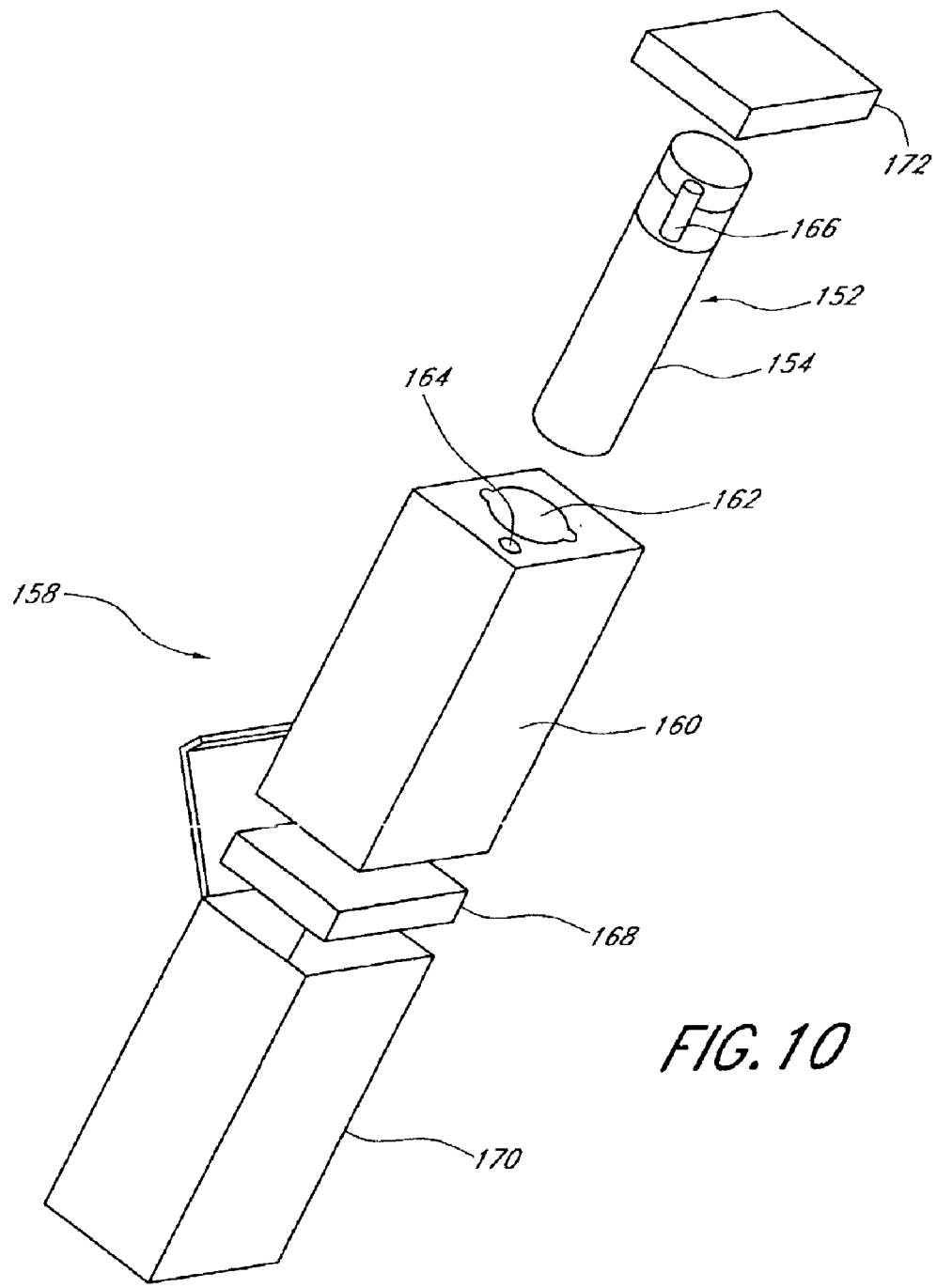
FIG. 10 is an exploded perspective view of a shipping assembly.

Referring to FIG. 10, a shipping assembly 158 is illustrated for shipment of the needle pig 152 to the clinical site. In the illustrated embodiment, a foam or other support 160 is provided with a needle pig cavity 162 for removably received the needle pig 152. A calibration pig cavity 164 is also provided, for receiving a calibration seed pig 166 which will be described below. The support 160, optionally with an additional foam base 168 is positioned within a shipping box 170. A foam lid 172 or other cushioning or closure element is positioned on top of the calibration seed pig 166 and needle pig 152, and placed within the box 170. The various components of the shipping assembly 158 preferably sufficiently attenuate radiation from the brachytherapy seeds that the loaded shipping assembly 158 may be transported under ordinary shipping conditions such as via Federal Express or other commercial carrier.

Figure 11:
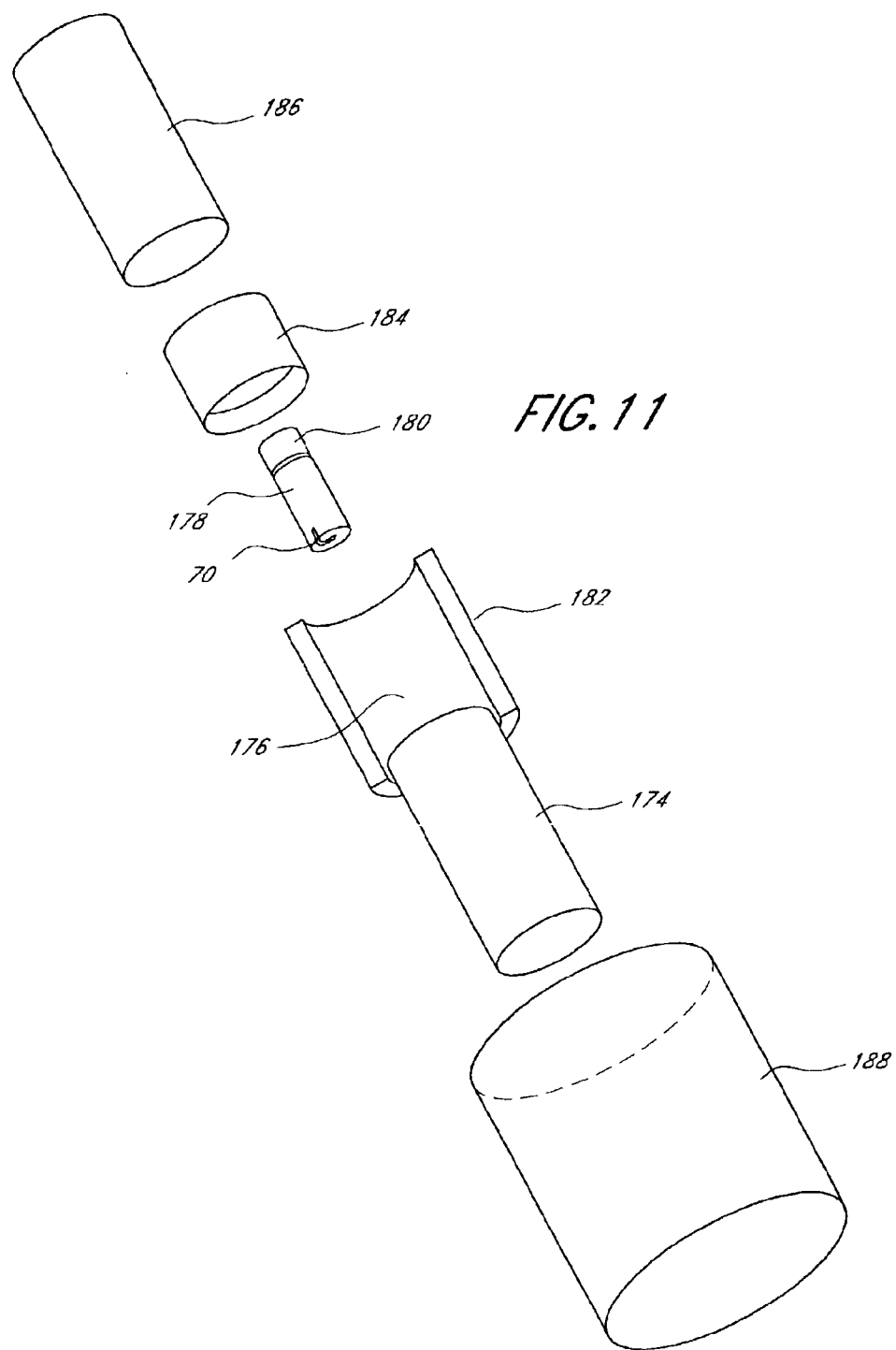
FIG. 11 is an exploded perspective view of a calibration seed pig.

Referring to FIG. 11, there is illustrated an exploded view of an exemplary calibration seed pig 166. Due to the known characteristics of radioactive decay, the activity of the brachytherapy seeds 70 is constantly declining until the radiation has dropped below a therapeutically useful range, and ultimately becomes fully dissipated. As a consequence, the activity must be assayed or calibrated at the time of the clinical procedure, to enable delivery of the desired radioactive dose. This is accomplished in the context of the present brachytherapy system by providing a calibration seed pig 166 which includes brachytherapy seeds 70 of the same activity as the seeds 70 which have been preloaded into each of the brachytherapy seed deployment devices 20. The provision of extra calibration seeds in the separate calibration seed pig 166 enables the clinical staff to calibrate the activity of the seeds without needing to disassemble any of the preloaded deployment devices or break the sterile seal on the needle pig 152.

The calibration seed pig 166 includes a pig base 174, constructed from a suitable radiation attenuating material such as lead. The pig base 174 is provided with a cavity 176 for receiving a glass vial 178. Glass vial 178 includes a plurality of seeds 70 having the same activity as the corresponding seeds in the associated deployment devices. A lid 180 is provided for the glass vial 178. The glass vial 178 is positioned within the cavity 176. The cavity 176 may be lined by an annular foam insert 182, to provide additional cushioning for the glass vial 178. The pig base 174 is closed by a corresponding pig lid 184. Preferably, a label 186 is provided on the pig base 174, and may be held thereto by an outer layer of shrink wrap 188.

Any of a variety of alternate constructions for the calibration seed pig may be devised, in view of the disclosure herein, to achieve the advantages of the present invention. In general, the distinct calibration seed pig enables the calibration of the brachytherapy seed deployment system without needing to open the sterile drape which includes the deployment device.

Figure 12:
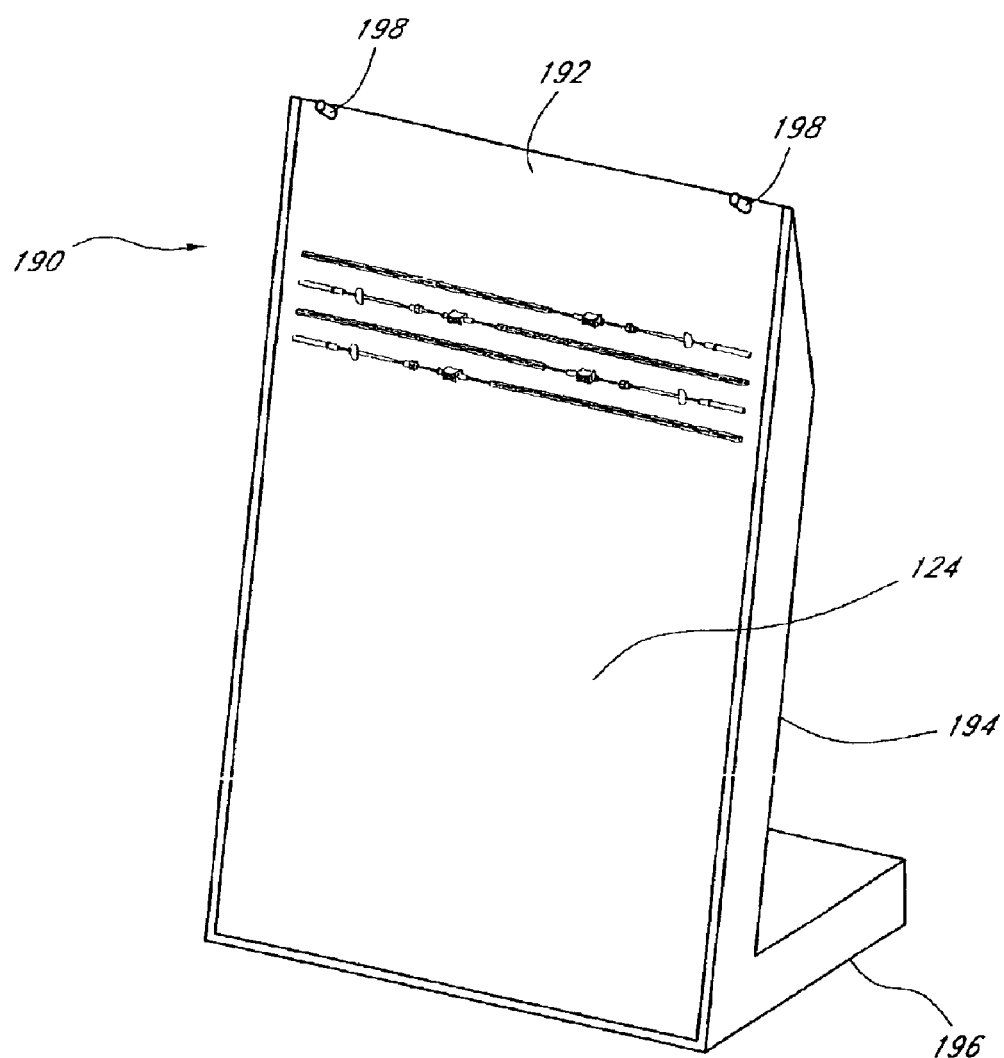
FIG. 12 is a front elevational perspective view of a closed needle drape attached to a needle stand.
Figure 13:
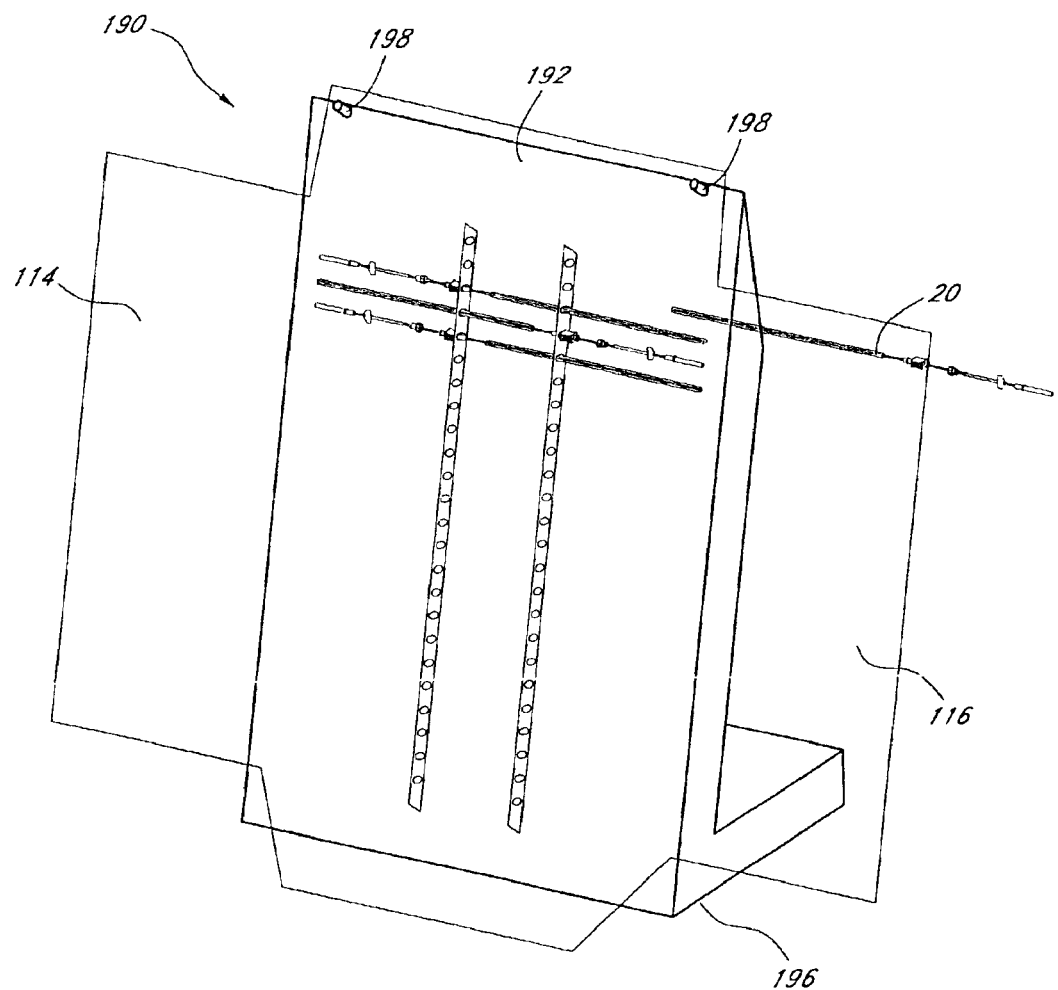
FIG. 13 is a view of a needle drape attached to a needle stand as in FIG. 11, with the needle drape open.

Referring to FIGS. 12 and 13, there is illustrated a drape stand 190 in accordance with another aspect of the brachytherapy seed delivery system of the present invention. The drape stand 190 comprises a support surface 192 for supporting a drape 124. Preferably, the support surface 192 lies in a plane which is inclined with respect to the horizontal, such as within the range of from about 45° to about 90°. Alternatively, the support surface 192 can be parallel to horizontal, although this orientation will require a greater countertop surface area.

The support surface 192 may be supported by or attached to a frame 194, and a base 196. Preferably, the base 196 is designed to fit on an existing surgical table, and has dimensions of approximately 9 inches by about 14 inches. The support surface 192 is preferably additionally provided with one or two or more attachment structures 198, such as post or clips for retaining a drape 124 thereon. In the illustrated embodiment, first and second posts 198 are adapted to receive first and second apertures 138 (see FIG. 6) to retain the drape 124 thereon.

As illustrated in FIG. 13, the right and left flaps 130 and 128 of the drape 124 may be opened, while the drape 124 is secured to the support surface 192, to facilitate sequential removal of each brachytherapy seed deployment device 20 as it may be needed during the procedure.

The drape stand 190 may be manufactured either as a one-time use disposable device, or as a reusable device. Preferably, the drape stand 190 is reusable, and may be manufactured from any other variety of materials such as stainless steel, or plastics which are well known in the medical device arts.

In addition to other advantages discussed previously herein, two types of customized dosing profiles are facilitated by the present invention. In the first, seed to seed activity may be varied within a single sleeve 32, to achieve higher resolution dosing patterns compared to the standard uniform seed activity devices currently in use. For example, at least a first seed within a sleeve 32 may be provided with a first activity, and at least a second seed in the same sleeve may be provided with a second, different activity. By "different", the inventors contemplate a measurable, intended different activity, and not merely manufacturing tolerance differences. Two or more seeds may be provided at the first activity, and two or more seeds may be provided at the second activity. Additional combinations may also be provided, based upon patient needs. In addition, more than two different activities may be provided in a single sleeve 32. For example, at least a first seed may be provided at a first activity, at least a second seed at a second activity, and at least a third seed at a third activity within a single sleeve 32.

In this manner, the activity and resulting delivered dose can be controllably varied along the axial direction of the needle. One or more needles prepared in this manner will have a first zone which exhibits at least a first activity, and a second zone which exhibits at least a second, different activity.

A second form of dose customization that can be readily accomplished in accordance with the present invention results from needle to needle variations in activity. A first sleeve 32 may be provided with one or more seeds having a first activity, and a second sleeve 32 may be provided with one or more seeds having a second, different activity. Combinations of the two forms of dose customization can also be used to optimize conformity between the three dimensional delivered dose profile and the desired treatment site.

Once the three dimensional shape of the desired target tissue has been established for a particular patient, and tissue to be avoided (e.g., urethra, rectum) has been mapped, the sleeves are loaded with seeds and spacers in a pattern to most closely conform to the target tissue in both the axial dimension and the transverse (to the axis of the needles) dimension. The deployment devices are assembled and loaded into the drape and prepared for shipment to the clinical site. At the site, the drape is preferably placed on a drape stand and each needle is removed and advanced into the target tissue at its unique, predetermined site to produce the predetermined three dimensional dosing profile. Preprocedure calibration can be enabled by either providing calibration seeds at each activity level, or providing calibration seeds at a single level or two levels from which calibration values for the other levels can be extrapolated.

FIGS. 14–21 illustrate preferred embodiments of the present brachytherapy seed deployment system. Each embodiment includes a plurality of spaced seeds 200 that are secured to a filament 202. Alternatively, the filament 202 may include only one attached seed 200, such that the filament 202 serves as a tether for the seed 200, as explained below.

A knot 214 may be tied at a distal end of the filament 202, or at a proximal end of the filament 202, or at both ends, or at neither end. The knot 214 or knots 214 help to maintain the position of the seeds 200 and filament 202 with respect to the sleeve 32, once the seeds 200 and filament 202 are placed within the sleeve 32. The filament 202 preferably comprises a bio-compatible, non-absorbable material such as a monofilament 7-0 suture. If desired, the filament 202 may comprise an elastic material. Preferred monofilament materials include polypropylene, silk, PGA, and polyglactin 910. Alternatively, the filament 202 may comprise an absorbable material. Preferably, however, the body would not absorb the absorbable filament 202 until after the effective life of the seeds 200 had expired. The absorbable filament 202 would thus maintain proper seed spacing throughout the useful life of the seeds 200. Those of skill in the art will appreciate that a variety of other suitable filament materials could be used instead.

The seeds 200 may be evenly or unevenly spaced along the filament 202 as needed to treat the cancerous tissue. For example, the system may be assembled in several standard configurations such as three seeds 200 at 1 centimeter intervals, four seeds 200 at 1 centimeter intervals, etc. Alternatively, the system may be custom assembled in configurations determined by a patient treatment plan submitted by the treating physician.

The filament 202 helps to maintain the proper spacing between adjacent implanted seeds 200. Because each seed 200 is securely fastened to the filament 202, no seed 200 can migrate away from the next adjacent seed 200 farther than the length of filament 202 between those two seeds 200. The filament 202 thus reduces the likelihood that an implanted seed 200 will migrate to an area of the body remote from the treatment site. Physicians performing brachytherapy with the present seed deployment system thus have greater flexibility as to seed deployment patterns.

Figure 43:
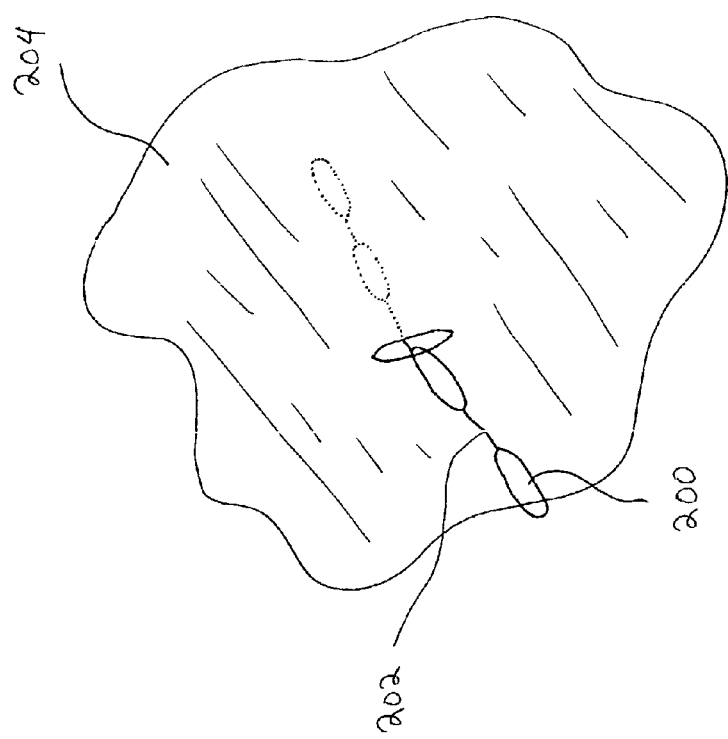
FIG. 43 is a schematic view of extra-capsular seeds.

In certain treatment situations, extra-capsular seeds 200 are advantageous. These seeds 200, shown in solid lines in FIG. 43, are located external to the prostate capsule 204. When such seeds 200 would benefit the patient, a physician may deploy a string of seeds 200 such that one or more of the seeds 200 are extra-capsular. The extra-capsular seeds 200 are unlikely to migrate to undesired areas of the body, even though they are located in less dense tissue, because they are tethered to intra-capsular seeds 200. If the filament 202 is elastic, the extra-capsular seeds 200 are able to migrate within a well-defined range depending upon the elasticity of the filament 202.

Figure 14:
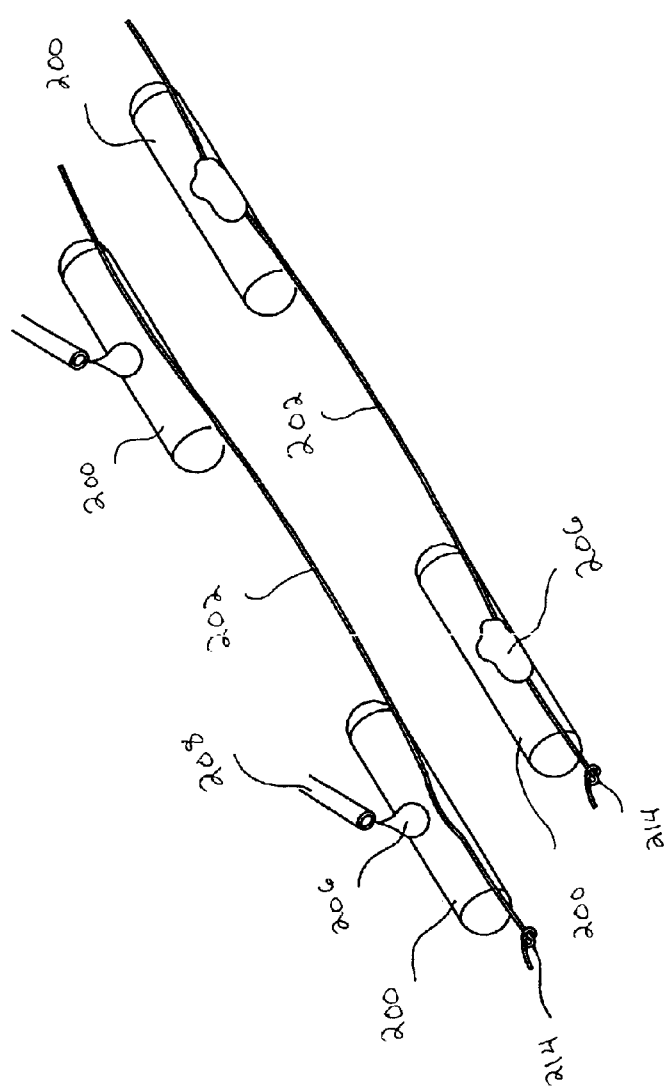
FIG. 14 is a perspective view of a preferred embodiment of the present brachytherapy seed deployment system, illustrating a method of securing the seeds to a filament.

In the embodiment of the present brachytherapy seed deployment system illustrated in FIG. 14, each seed 200 is independently secured to a single filament 202 using a biocompatible glue or adhesive 206. Preferably, a small amount of glue 206 is applied at an outer midpoint of the seed 200 using a micro-applicator 208. The glue 206 may, however, be applied in any other area of the seed 200. Preferred glues include cyanoacrylate and urethane UV cure. Those of skill in the art will appreciate that other adhesives could be used instead.

To maintain the desired spacing between adjacent seeds 200 before, during and after implantation, the assembled seed deployment system may include a benign spacer 210 between adjacent seeds 200. The spacers 210 are preferably constructed of a biocompatible material, and may be absorbable or non-absorbable. The spacers 210 may also serve as anchors. For example, a physician may implant a string of seeds 200 including one or more spacers 210 at a distal end. By implanting only the spacer 210 or spacers 210 within the prostate capsule 204, the seeds 200 would be free to migrate within the range of the filament 202 that tethers them to the anchored spacer 210 or spacers 210. If desired, the filament 202 may include only one attached seed 200.

Figure 15:
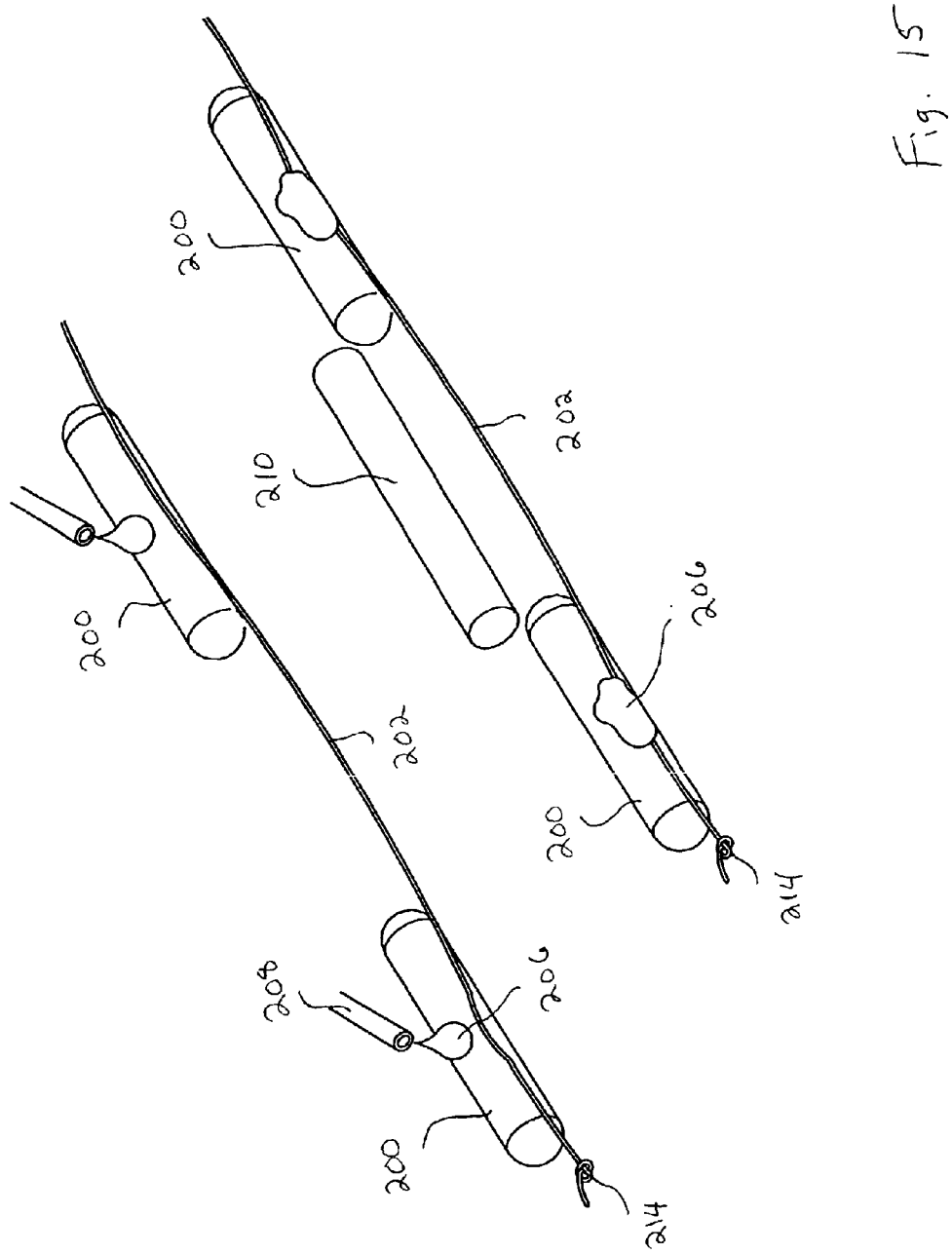
FIG. 15 is a perspective view of the brachytherapy seed deployment system of FIG. 14 including spacers.

In the embodiment of FIG. 15, each seed 200 is independently secured to a single filament 202 using a biocompatible glue 206, and a spacer 210 is provided between adjacent seeds 200. In the illustrated embodiments, the spacers 210 are not secured to the filaments 202. However, those of skill in the art will appreciate that the spacers 210 could be secured to the filaments 202 using any of the same attachment methods disclosed herein, or any other methods known to those skilled in the art.

Figure 16:
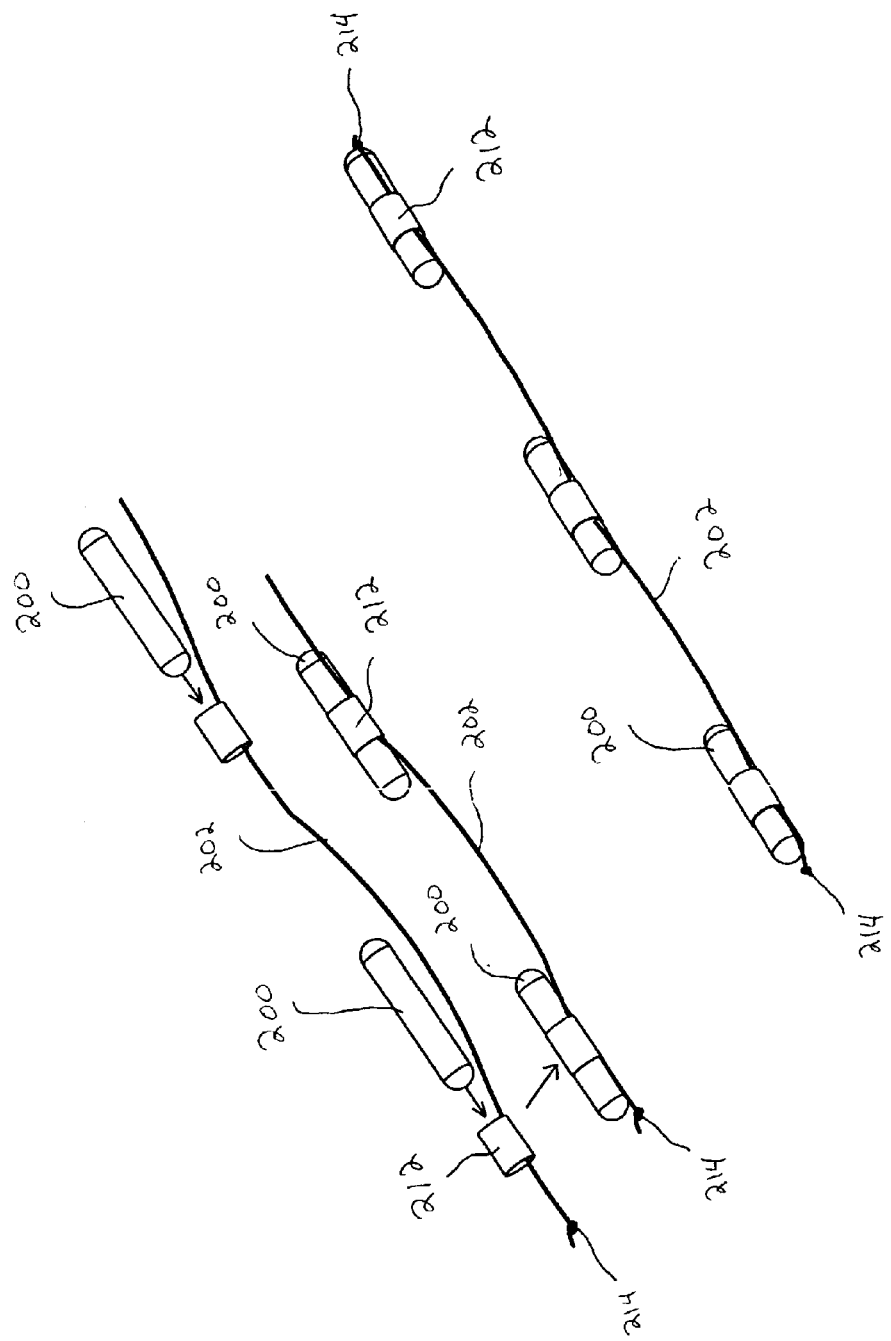
FIG. 16 is a perspective view of another preferred embodiment of the present brachytherapy seed deployment system, illustrating another method of securing the seeds to a filament.
Figure 17:
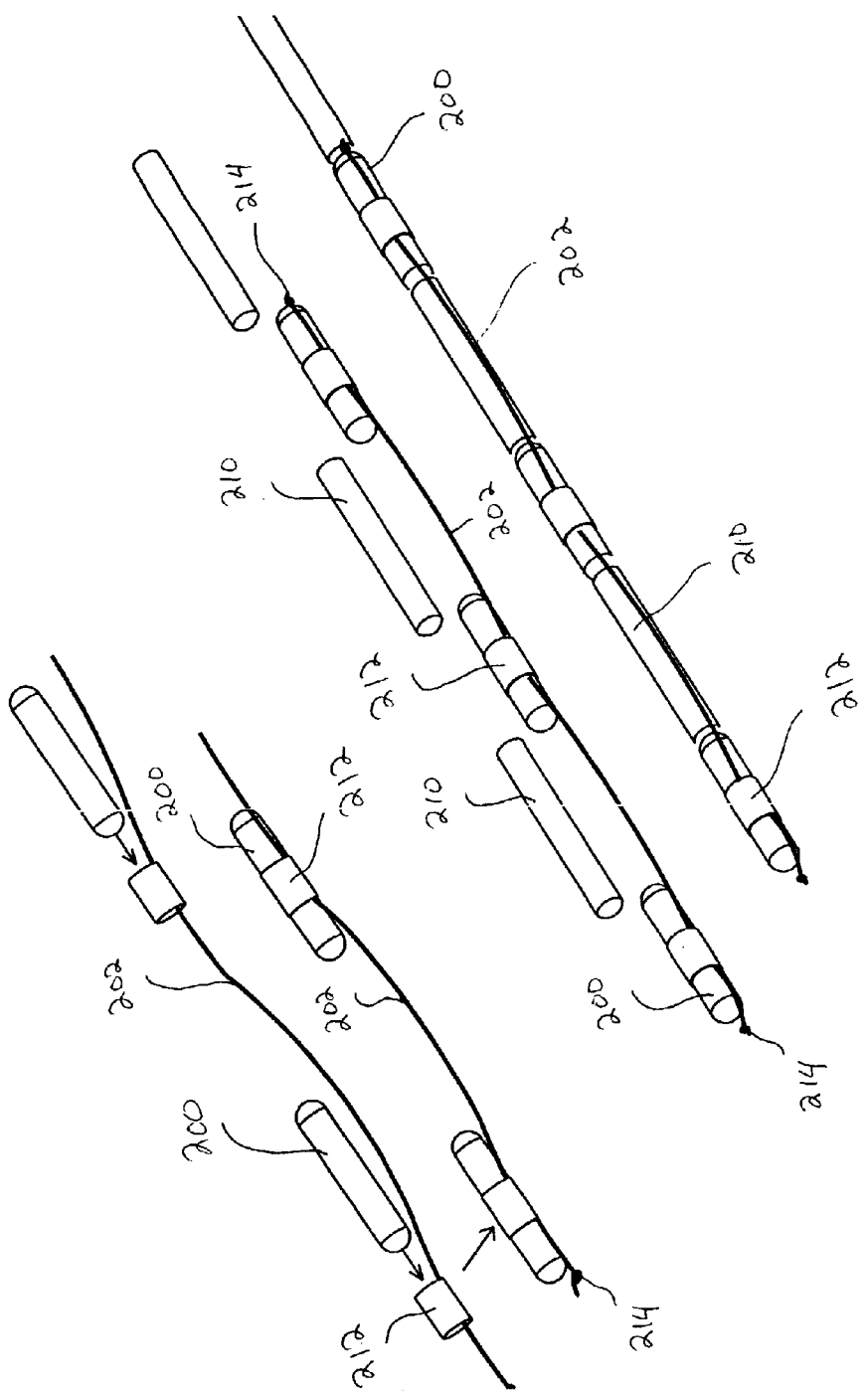
FIG. 17 is a perspective view of the brachytherapy seed deployment system of FIG. 16 including spacers.

In the embodiment illustrated in FIG. 16, each seed 200 is independently secured to a single filament 202 using a biocompatible collar 212, and in the embodiment illustrated in FIG. 17 a spacer 210 is provided between adjacent seeds 200. The collar 212 fits snugly around the circumference of the seed 200 and traps the filament 202 between an outer wall of the seed 200 and an inner wall of the collar 212. The collar 212 may be glued, heat shrunk or otherwise attached to the seed 200 to prevent the seed 200 from detaching from the filament 202. In one embodiment, the collar 212 secures the seed 200 to the filament 202 in a loose enough fashion that the seed 200 and collar 212 may be slid along the filament. A physician implanting the seeds 200 may thus alter a spacing between seeds 200, as described in detail below.

The collar 212 is preferably substantially shorter than the seed 200 as measured in a longitudinal direction. A preferred collar length is 1–2 mm. The collar 212 is preferably located at or near a midpoint of the seed 200. The collar 212 is preferably constructed of a material that will not attenuate the radioactive properties of the seed 200. If the collar 212 is to be heat shrunk, then preferably the collar 212 is constructed of a material that shrinks upon the application of heat. Preferred collar materials are polyimide, polyesters, polyethylenes, polyamides, ptfe's, polypropylene and ploysulfones. Those of skill in the art will appreciate that other collar materials could be used instead. In the event that the material used for the collar 212 does not diminish the effectiveness of the seeds 200, the collar 212 may be the same length as or longer than the seed 200 and hold the entire seed 200 adjacent the filament 202, as will be understood by those of skill in the art.

In addition to the adhesive 206 and collar 212, the seeds 200 and/or spacers 210 could be secured to the filaments 202 using other methods known to those of skill in the art.

Figure 18:
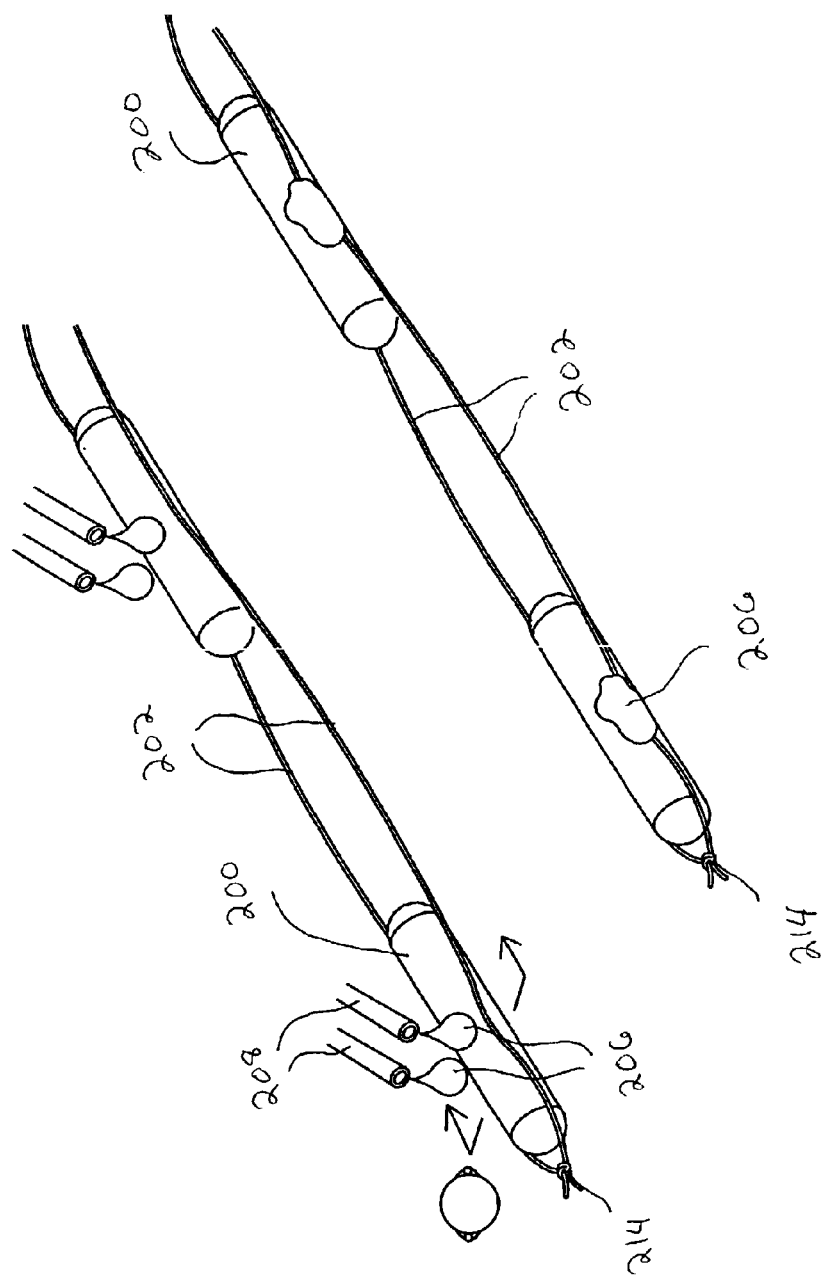
FIG. 18 is a perspective view of another preferred embodiment of the present brachytherapy seed deployment system, illustrating another method of securing the seeds to at least two filaments.
Figure 19:
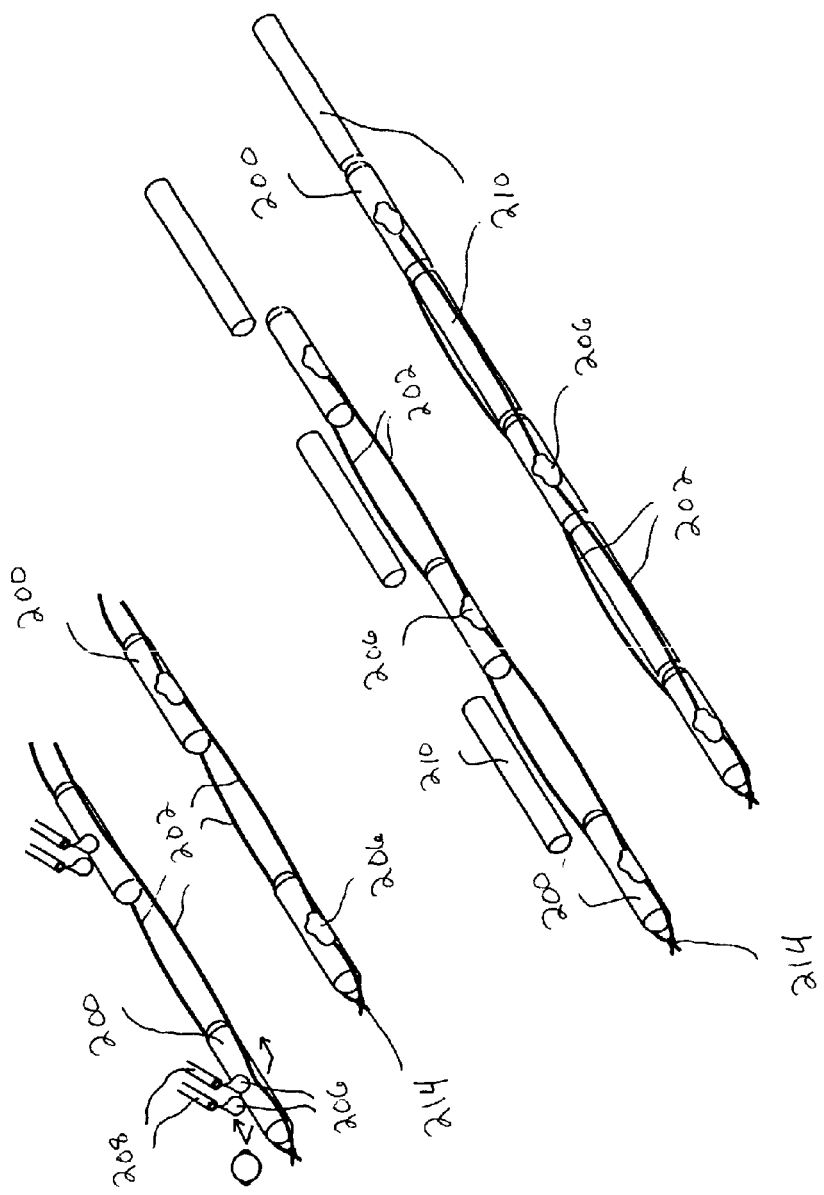
FIG. 19 is a perspective view of the brachytherapy seed deployment system of FIG. 18 including spacers.

In the embodiment illustrated in FIG. 18, each seed 200 is independently secured to two strands of filament 202 using a biocompatible glue 206, and in the embodiment illustrated in FIG. 19 a spacer 210 is provided between adjacent seeds 200. In the embodiment illustrated in FIG. 20, each seed 200 is independently secured to two strands of filament 202 using a biocompatible collar 212, and in the embodiment illustrated in FIG. 21 a spacer 210 is provided between adjacent seeds 200. Preferably, the two filament strands 202 are located at positions on the seeds 200 that are diametrically opposed to one another. Ends of the filaments 202 may be tied together in a knot 214 at distal and/or proximal ends of the assembly, or the ends may remain loose. Those of skill in the art will appreciate that more strands could be provided.

In the above described embodiments, the seeds 200 are attached to the filaments 202 in a linear fashion. Those of skill in the art will appreciate that the seeds 200 could be attached to the filaments 202 in a variety of other arrangements. For example, several seeds 200 may be secured via filaments 202 to a central seed 200 in a radial, or hub and spoke, pattern. During implantation, one or more of the radially attached seeds 200 may be intra-capsular, leaving the remaining seeds 200 to migrate in the vicinity of the cancerous tissue due to their tethering to the intra-capsular seeds 200.

Figure 40:
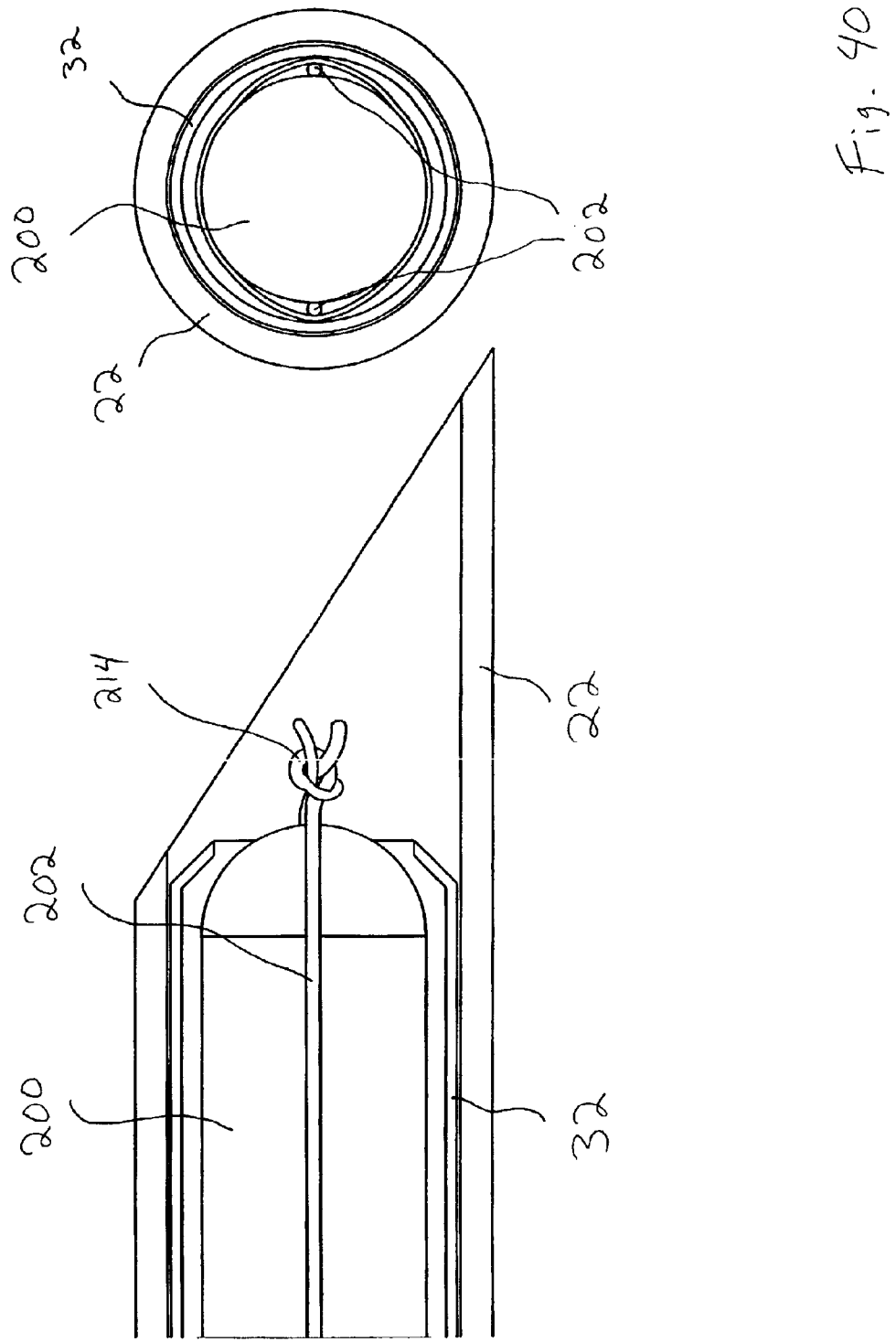
FIG. 40 is a detail side elevation view of a distal end of the present brachytherapy seed deployment system loaded into a sleeve and needle, and a cross-sectional end view of the present brachytherapy seed deployment system loaded into a sleeve and needle.

The embodiments depicted in FIGS. 14–21 are preferably implanted using the device 20 described above. Before implantation, the seeds 200 (and spacers 210 if provided) are loaded into a sleeve 32. FIGS. 31–38 illustrate the embodiments of FIGS. 14–21, respectively, inserted into sleeves 32. The sleeve 32 is then preferably inserted into a needle 22, as illustrated in FIG. 40. Preferably, there is sufficient clearance between the seed/filament assembly and the inside wall of the sleeve 32 so that the assembly does not get jammed in the sleeve 32 during implantation.

Figure 39:
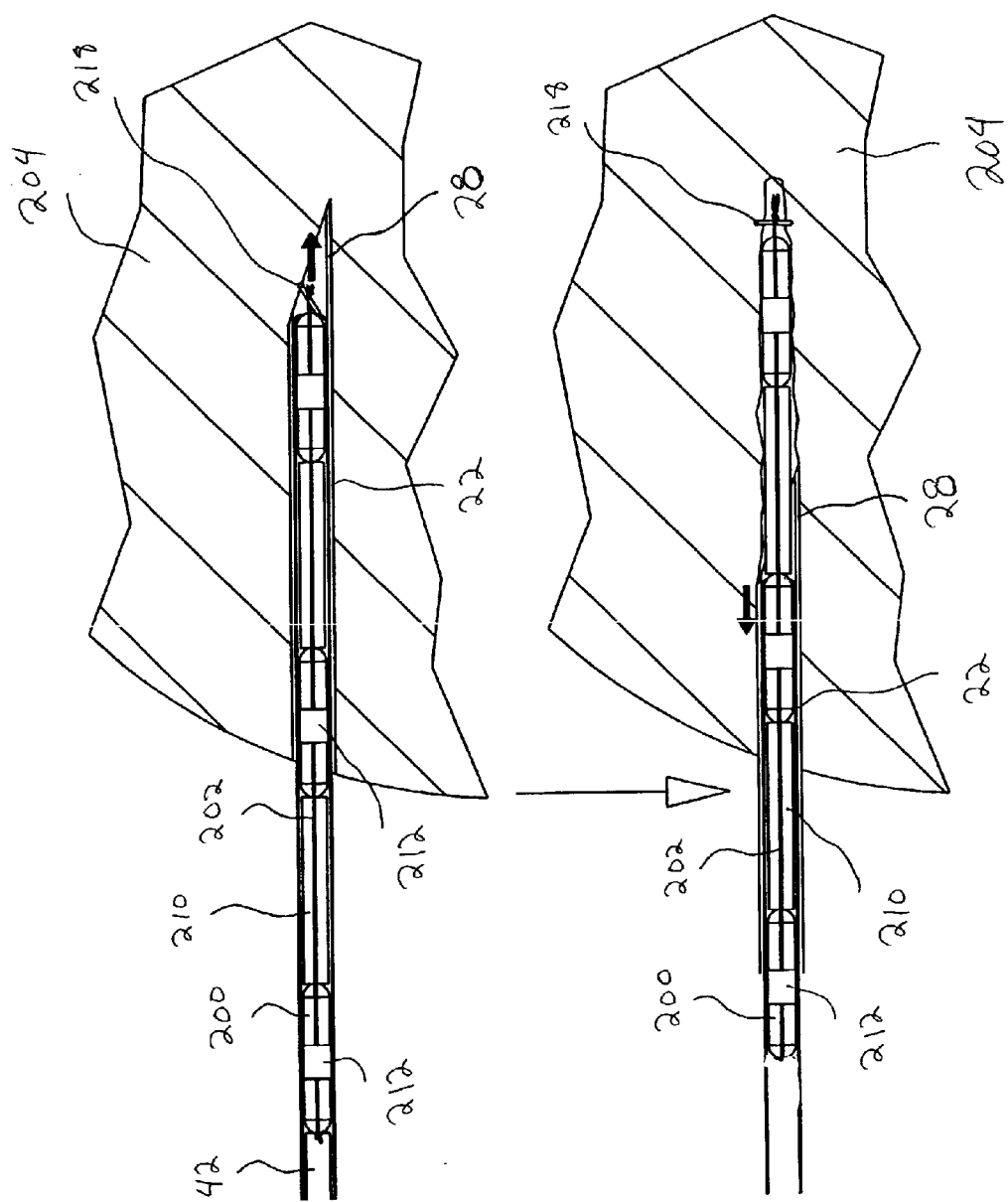
FIG. 39 is a side elevation view of a preferred method of implanting the brachytherapy seed deployment system of FIGS. 17, 21, 26 and 27.

During implantation, the physician expels the seeds 200 from of the sleeve using the obturator 42, as shown in FIG. 39. Spacing between adjacent seeds 200 is advantageously maintained in embodiments including spacers 210. In embodiments without spacers 210, preferably the most distal seed 200 is securely anchored into the surrounding tissue 204 so that tension in the filament 202 causes the seeds 200 to be properly spaced as the physician withdraws the sleeve 32 and needle 22. The embodiments illustrated in FIGS. 22–27 and 42 provide preferred structures for anchoring the most distal seed 200 in the surrounding tissue 204. Any of these structures may be used with any of the embodiments depicted in FIGS. 14–21.

Figure 22:
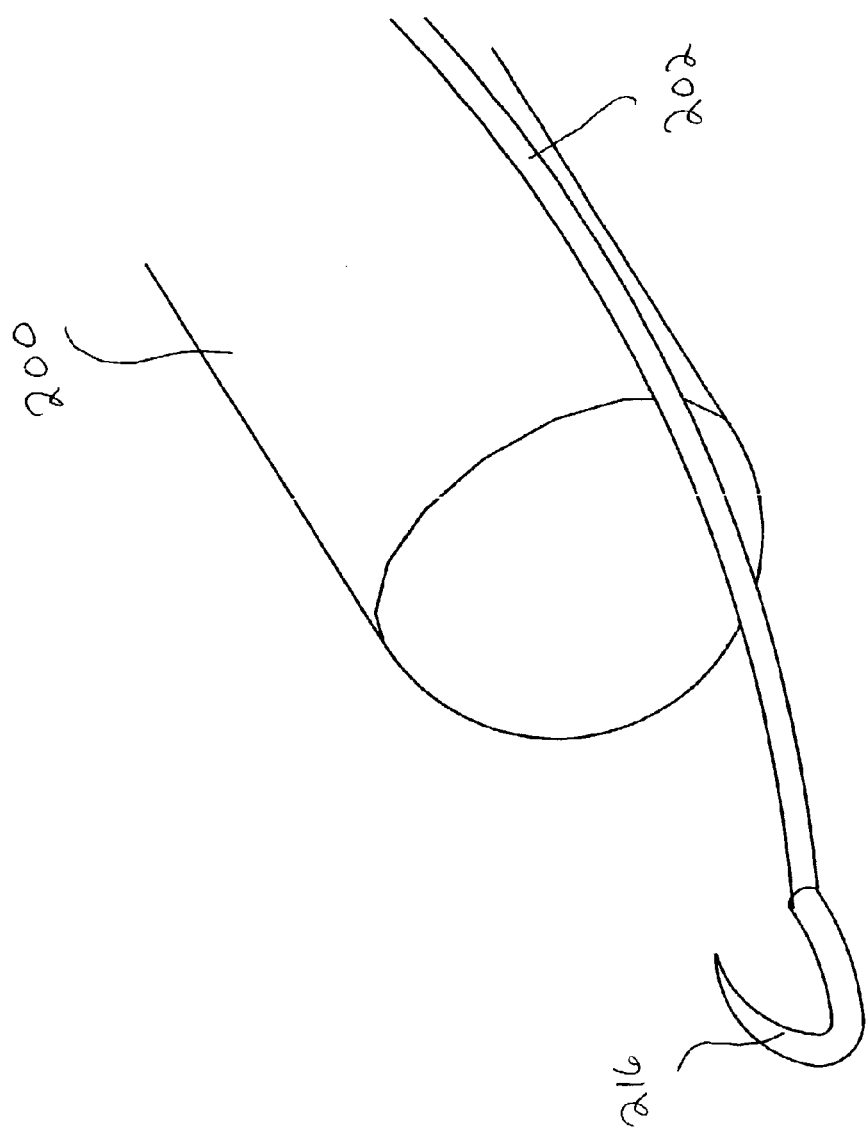
FIG. 22 is a perspective view of another preferred embodiment of the present brachytherapy seed deployment system, illustrating a method of securing the filament.
Figure 23:
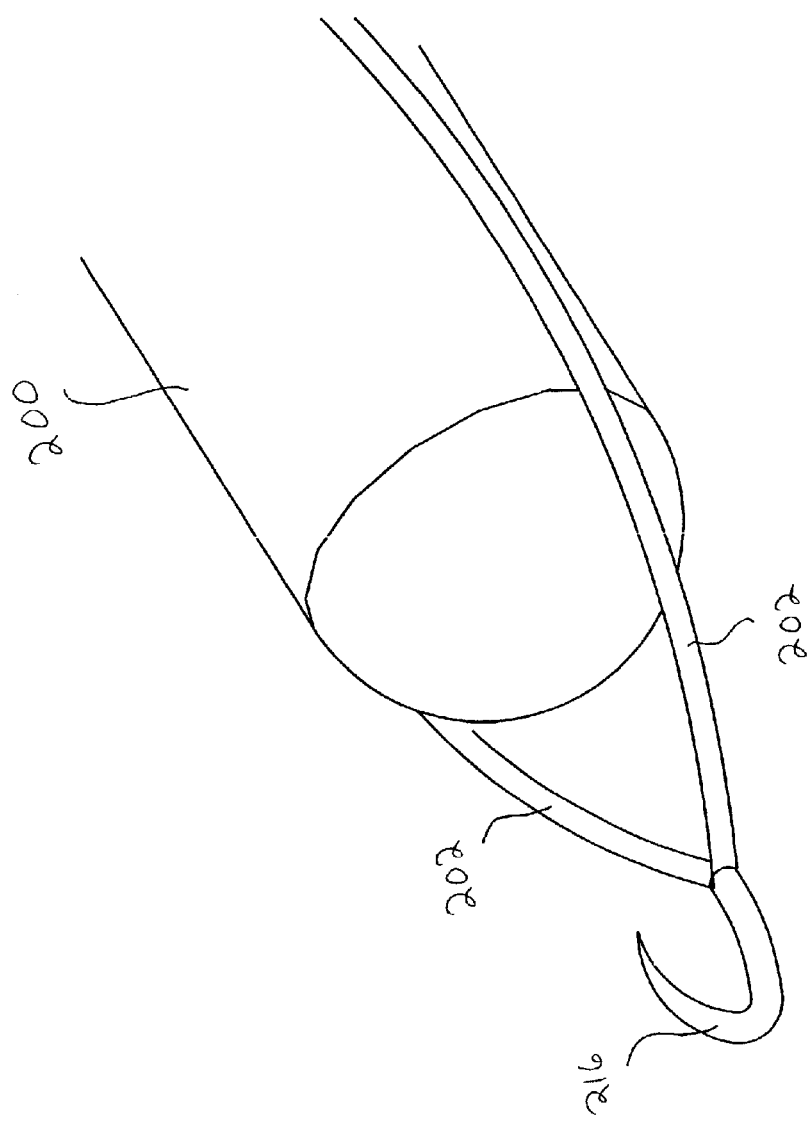
FIG. 23 is a perspective view of another preferred embodiment of the present brachytherapy seed deployment system, illustrating another method of securing the at least two filaments.
Figure 24:
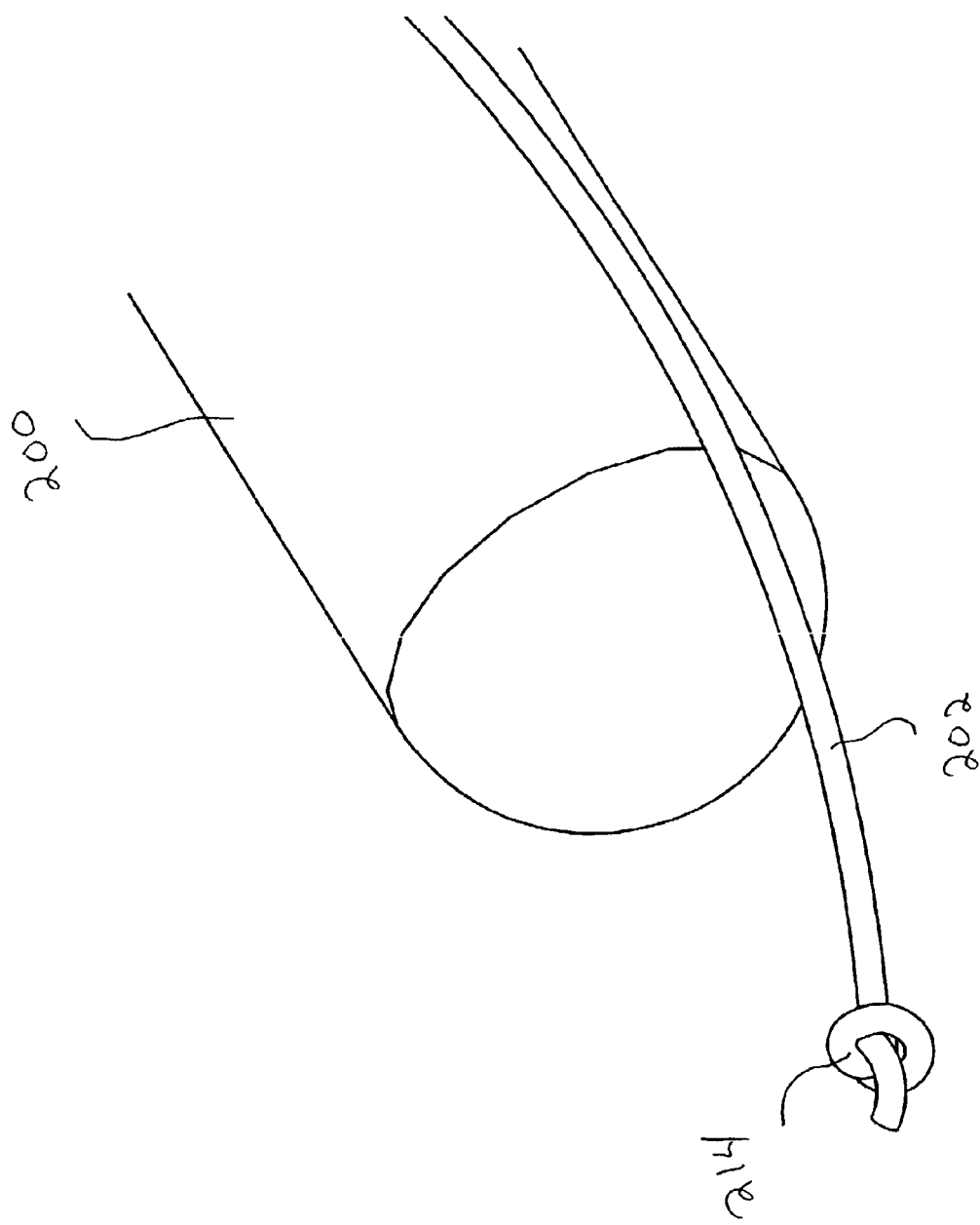
FIG. 24 is a perspective view of another preferred embodiment of the present brachytherapy seed deployment system, illustrating another method of securing the filament.
Figure 25:
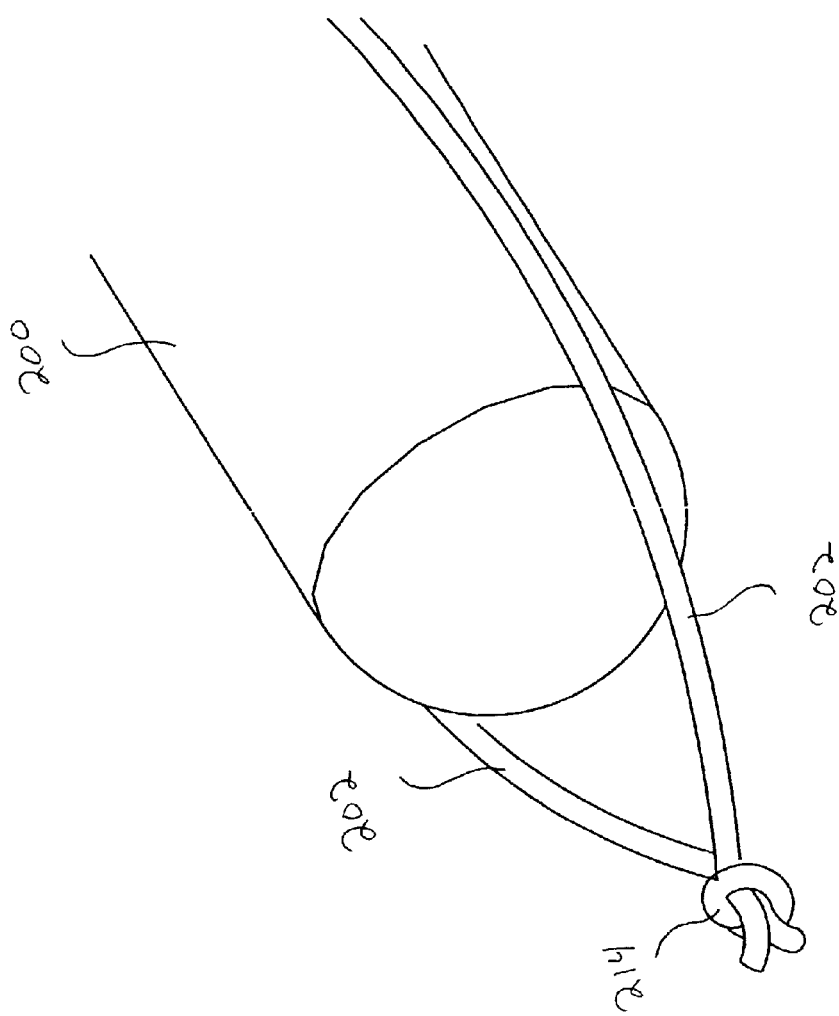
FIG. 25 is a perspective view of another preferred embodiment of the present brachytherapy seed deployment system, illustrating another method of securing the at least two filaments.
Figure 26:
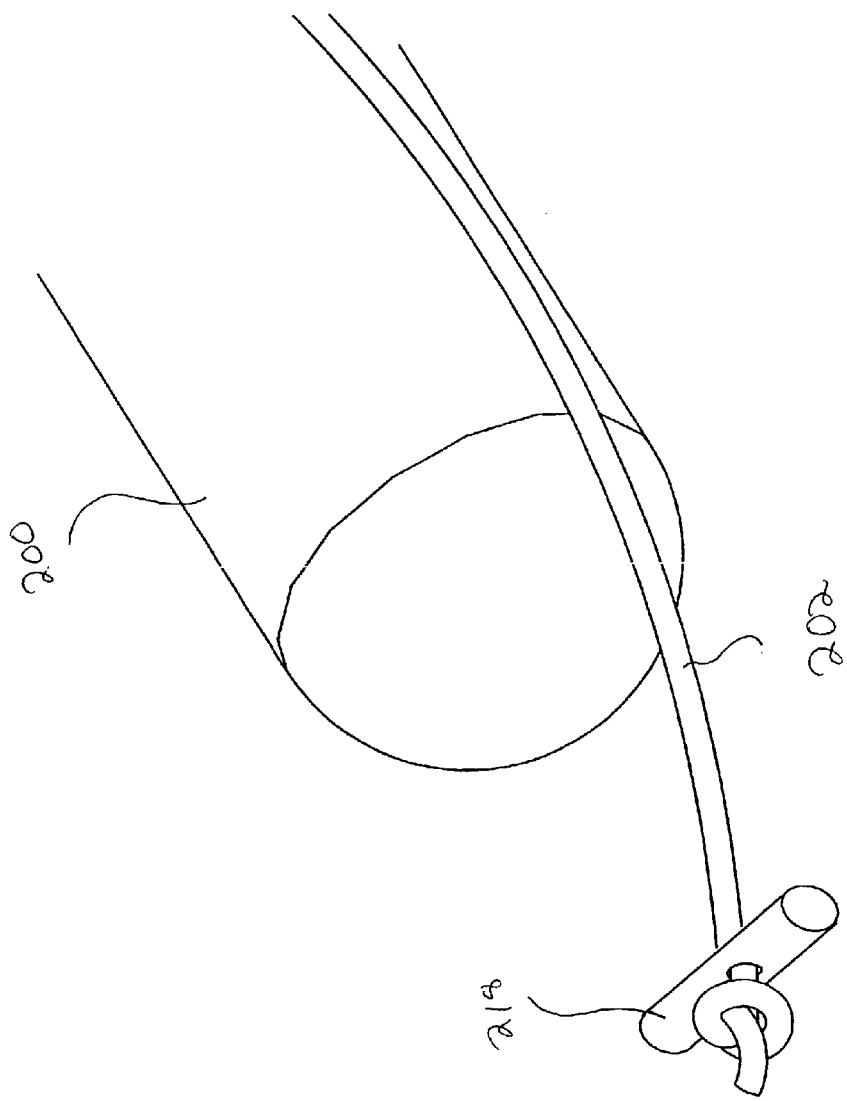
FIG. 26 is a perspective view of another preferred embodiment of the present brachytherapy seed deployment system, illustrating another method of securing the filament.
Figure 27:
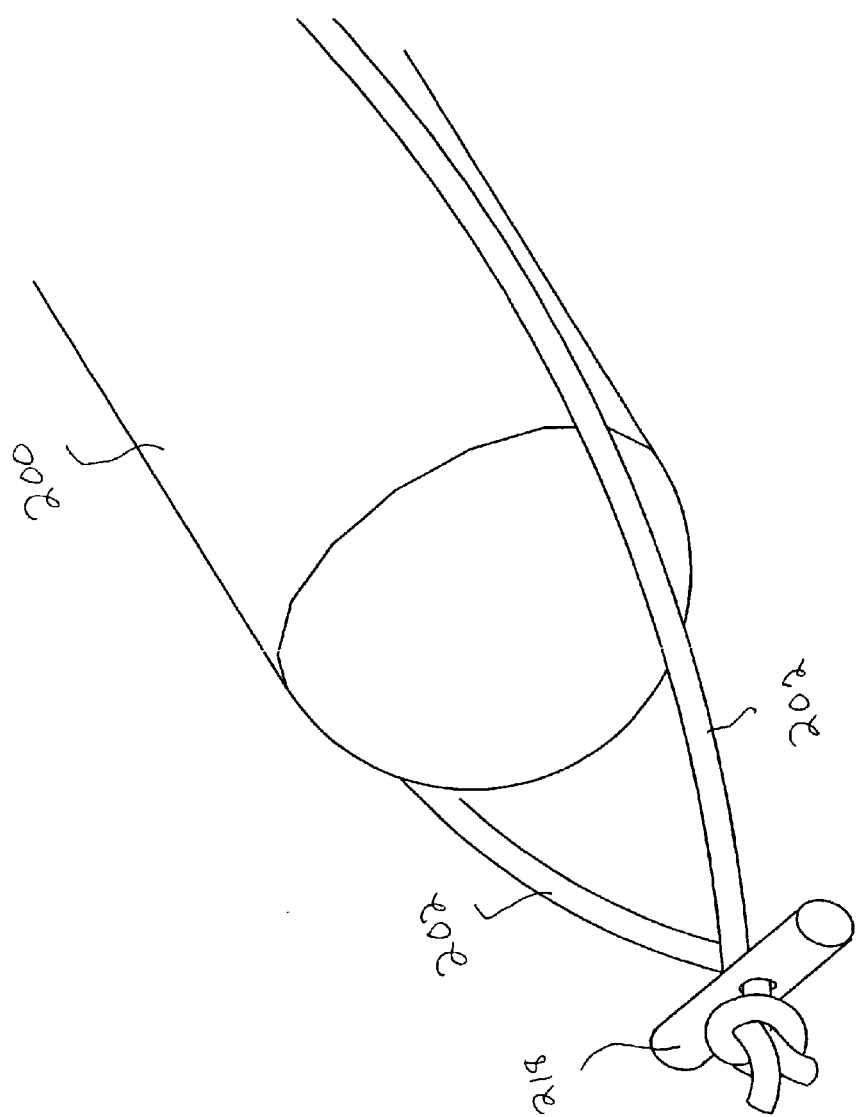
FIG. 27 is a perspective view of another preferred embodiment of the present brachytherapy seed deployment system, illustrating another method of securing the at least two filaments.

In the embodiments of FIGS. 22 and 23, the anchoring structure comprises a hook 216. In the embodiments of FIGS. 24 and 25 a knot 214 in the filament 202 or filaments 202 comprises the anchoring structure, and in the embodiments of FIGS. 26 and 27 a "T" bar 218 comprises the anchoring structure. The anchors 214, 216, 218 may be secured to the filament 202 or filaments 202 using tying, bonding, swaging or other mechanical means. Using the embodiments of FIGS. 26 and 27 as an example, a typical implantation procedure is illustrated in FIG. 39. Although the system depicted in this figure includes spacers 210, the spacers 210 are unnecessary to maintain the spacing between adjacent seeds 200.

The physician penetrates the prostate capsule tissue 204 with the needle 22 as shown in the upper figure. Holding the obturator 42 steady as he or she withdraws the sleeve 32, the physician then expels the seeds 200 until the most distal seed 200 protrudes from the distal end 28 of the needle 22. The T bar 218 engages and becomes anchored in the tissue 204. As the physician withdraws the needle 22 and sleeve 32, the anchored T bar 218 creates tension in the filament 202 that properly spaces the seeds 200.

Figure 42:
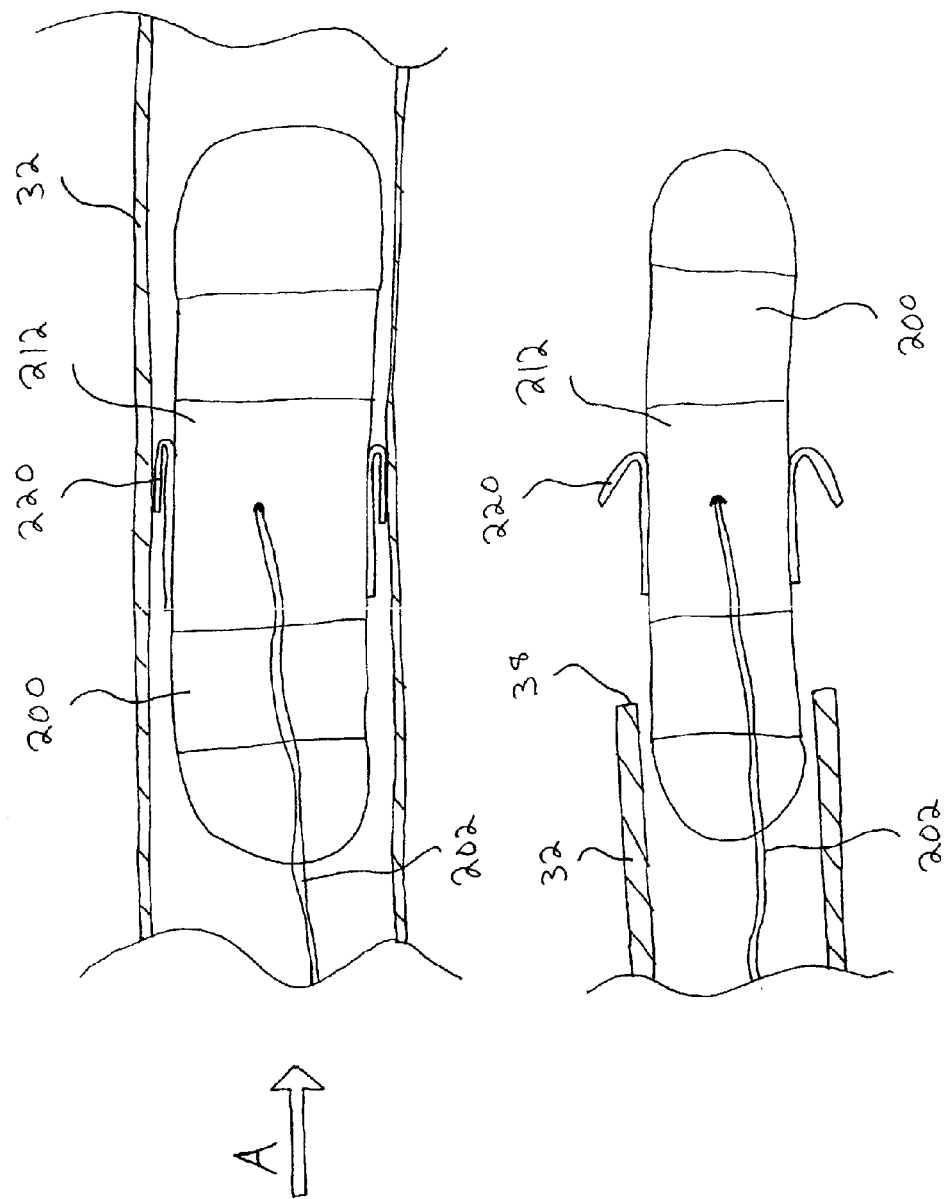
FIG. 42 is a schematic side view of another preferred seed for use in the present brachytherapy seed deployment system.

FIG. 42 illustrates another preferred configuration for a most distal seed 200. The seed 200 includes at least one barb 220 secured to an outer surface. The seed 200 may include two or more barbs 220, as shown. The barbs 220 may be attached to a collar 212 wrapped about the seed 200, as shown, or may be glued directly to the seed 200. The seed 200 is inserted into the sleeve 32 in the direction of the arrow A, such that the inner wall of the sleeve 32 compresses the barbs 220 against the seed 200. During implantation, when the seed 200 exits the distal end 38 of the sleeve 32, the barbs 220 extend outward and engage the prostate capsule 204 and anchor the seed 200 in the surrounding tissue. Similar to the anchors 214, 216, 218 described above, the barbs 220 create tension in the filament 202 or filaments 202 as the physician withdraws the sleeve 32. The tension causes the seeds 200 to maintain the desired spacing.

Figure 41:
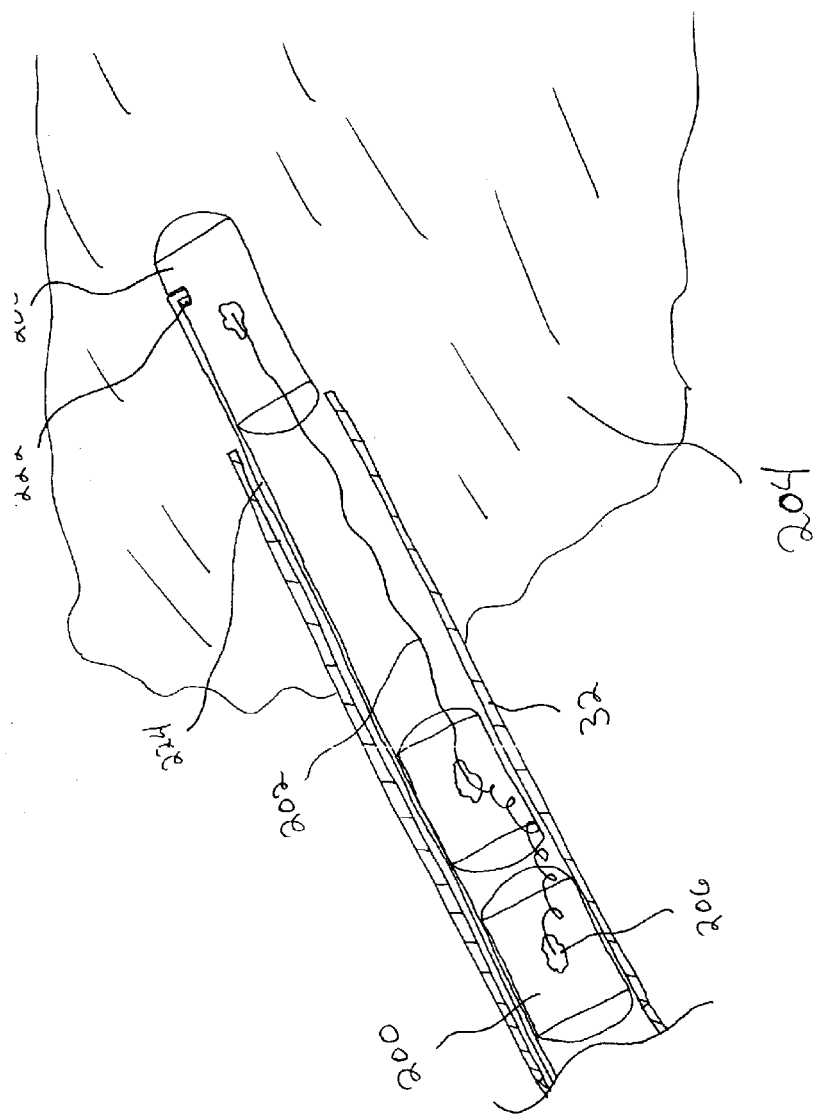
FIG. 41 is a schematic partial cross-sectional side view of another preferred device and method of implanting the present brachytherapy seed deployment system.

FIG. 41 illustrates another preferred embodiment of the present brachytherapy seed deployment system. In this embodiment, the most distal seed 200 includes a notch 222 in an outer surface. A rigid wire 224 inserted longitudinally through the sleeve 32 is removably engageable with the notch 222. As the physician withdraws the sleeve 32, he or she applies a pushing force to the wire 224 to maintain the position of the most distal seed 200 within the prostate capsule 204. This pushing force creates tension in the filament 202 or filaments 202 that causes the seeds 200 to maintain the desired spacing as the physician withdraws the sleeve 32. Once the sleeve is removed and the seeds 200 are properly spaced, the wire 224 may be disengaged from the distal seed 200 and withdrawn.

Figure 20:
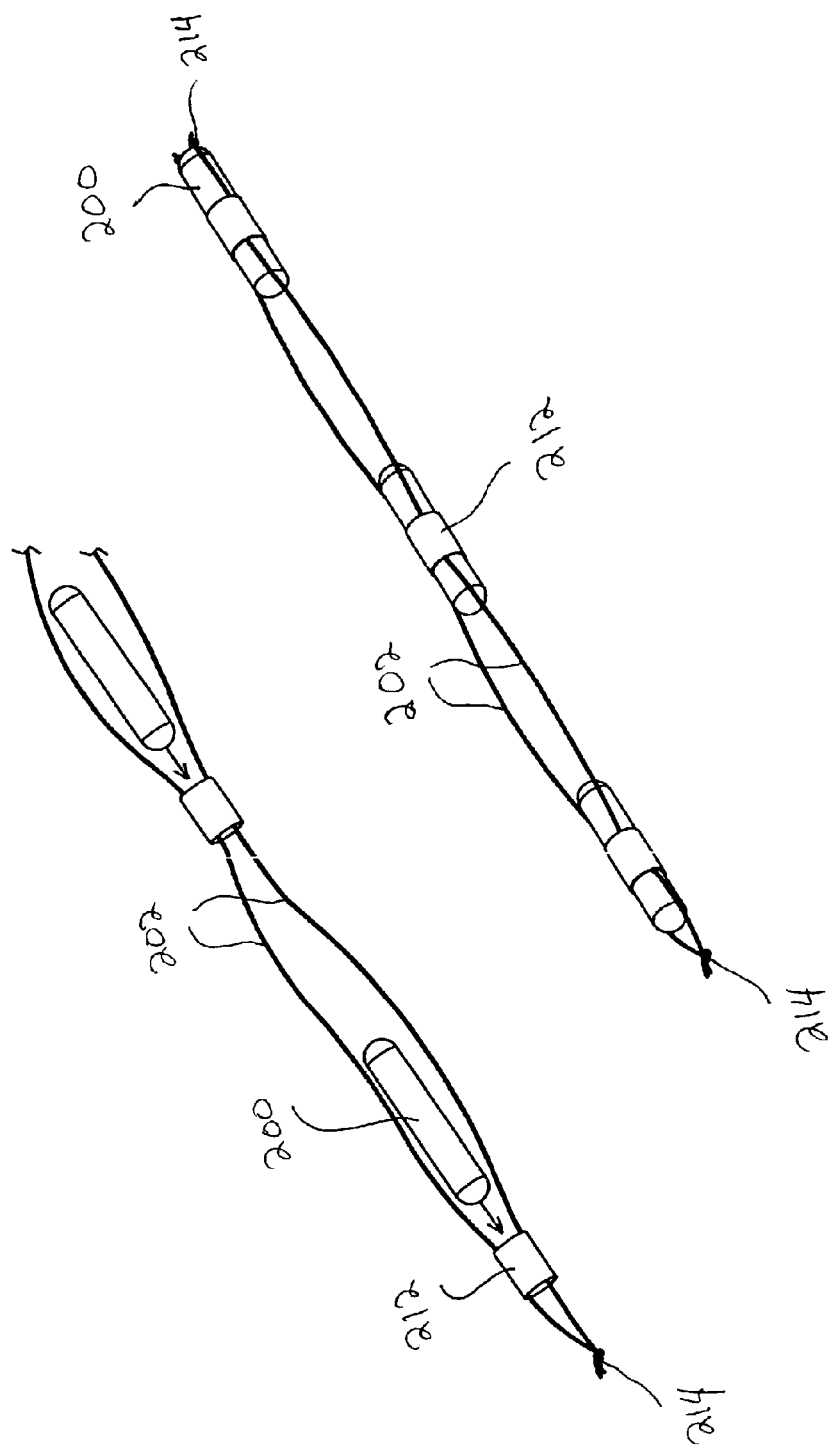
FIG. 20 is a perspective view of another preferred embodiment of the present brachytherapy seed deployment system, illustrating another method of securing the seeds to at least two filaments.
Figure 21:
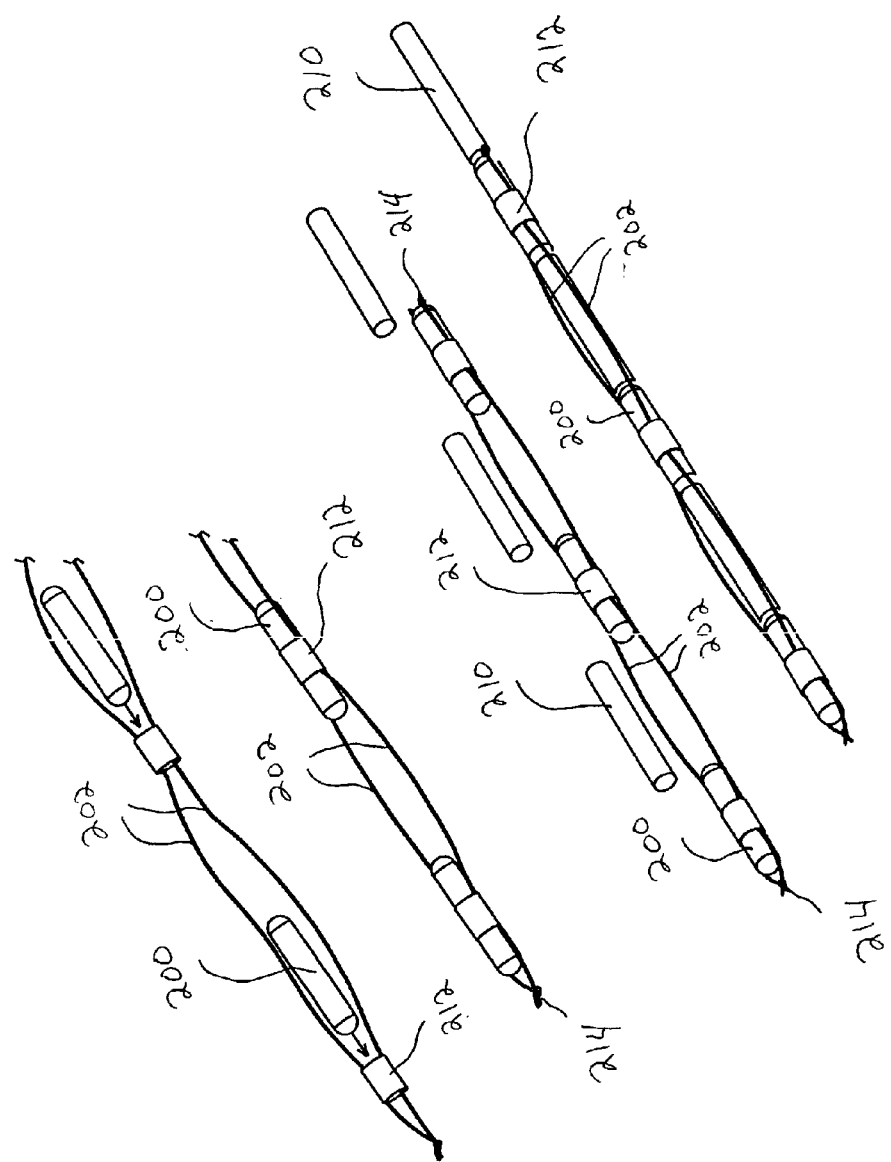
FIG. 21 is a perspective view of the brachytherapy seed deployment system of FIG. 20 including spacers.
Figure 28:
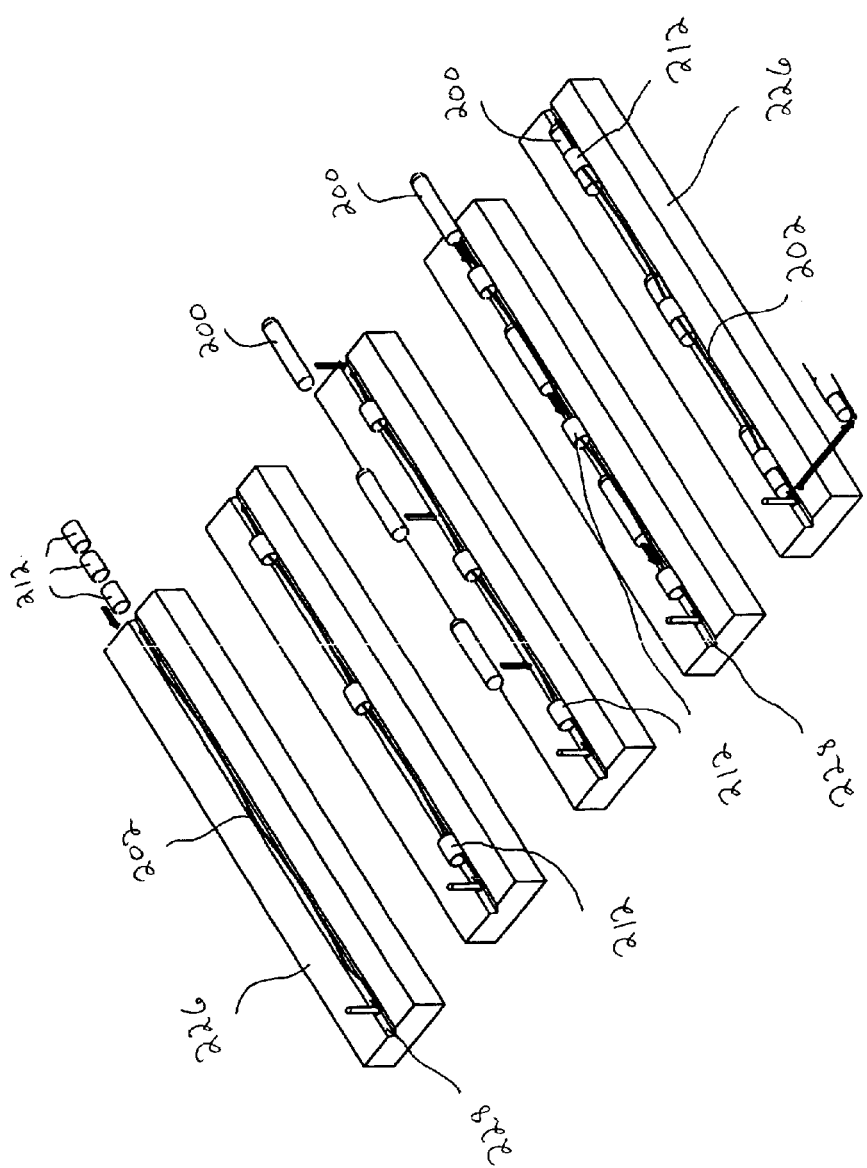
FIG. 28 is a perspective view of a preferred method of assembling the brachytherapy seed deployment system of FIG. 16.
Figure 29:
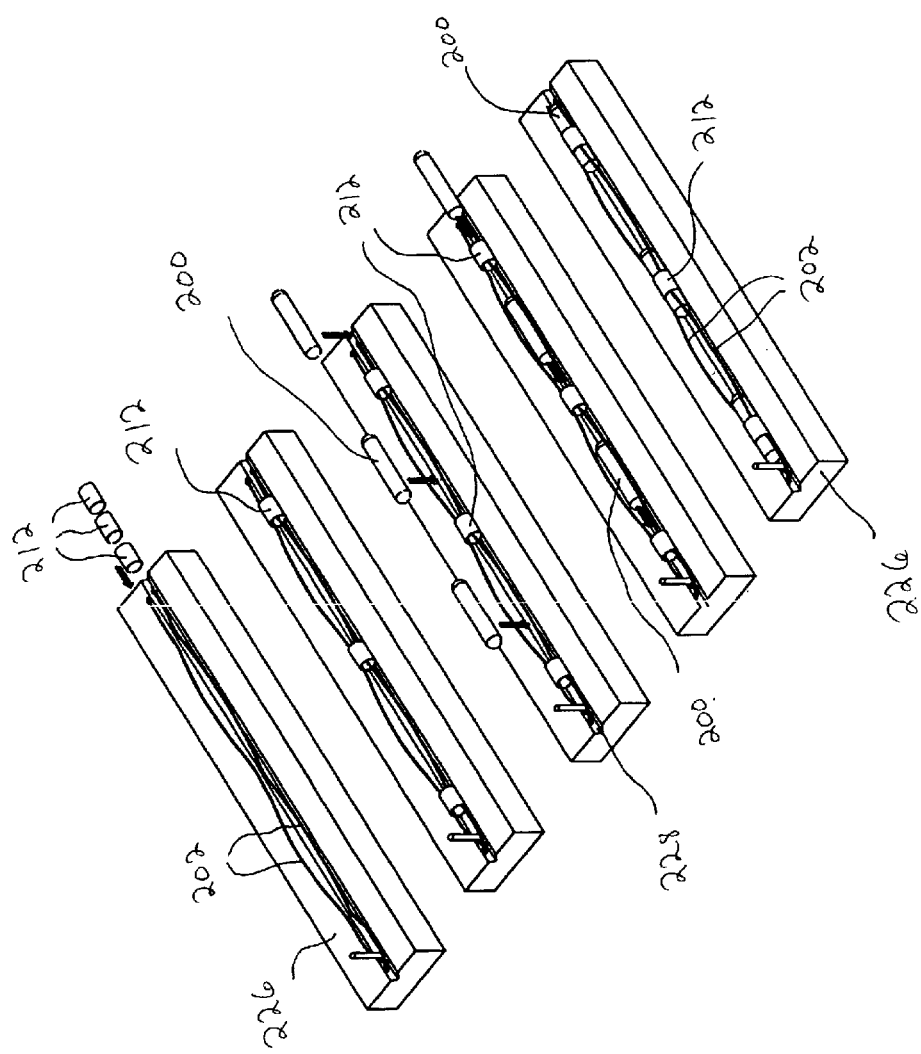
FIG. 29 is a perspective view of a preferred method of assembling the brachytherapy seed deployment system of FIG. 20.

FIG. 28 illustrates a preferred method of assembling the embodiment of FIG. 16, and FIG. 29 illustrates a preferred method of assembling the embodiment of FIG. 20. A fixture 226 comprising a longitudinal slot 228 preferably supports the components during the assembly process. The type of filament 202 to be used is preferably selected first. If desired, an anchor 214, 216, 218 such as those described above is secured to a distal end of the filament 202 or filaments 202. The distal end is then secured within the fixture slot 228 and the filament 202 or filaments 202 are pulled taut.

The desired number of collars 212 are slid down the filament 202 or filaments 202 to their approximate final attachment points. The seeds 200 are then slid into the collars 212. If a single filament 202 is used, then the filament 202 may be located on any side of the seed 200. If dual filaments 202 are used, then preferably the filaments 202 are located on opposite sides of the seed 200.

The seeds 200 and collars 212 are slid along the filament 202 or filaments 202 to their exact final locations and are secured in place using one of the methods described above or another equivalent method. If desired, spacers 210 may then be added between the seeds 200. Any remaining filament 202 at the ends of the assembly is cut and may be knotted if desired. If the ends are knotted, preferably the knots 214 are located an appropriate distance from the end seeds 200 so as to enable the assembly to slide easily into a sleeve 32.

Although not pictured, the embodiments including glue 206 rather than collars 212 are assembled in substantially the same fashion just described. However, the step of threading the collars 212 onto the filament 202 or filaments 202 is eliminated.

Figure 30:
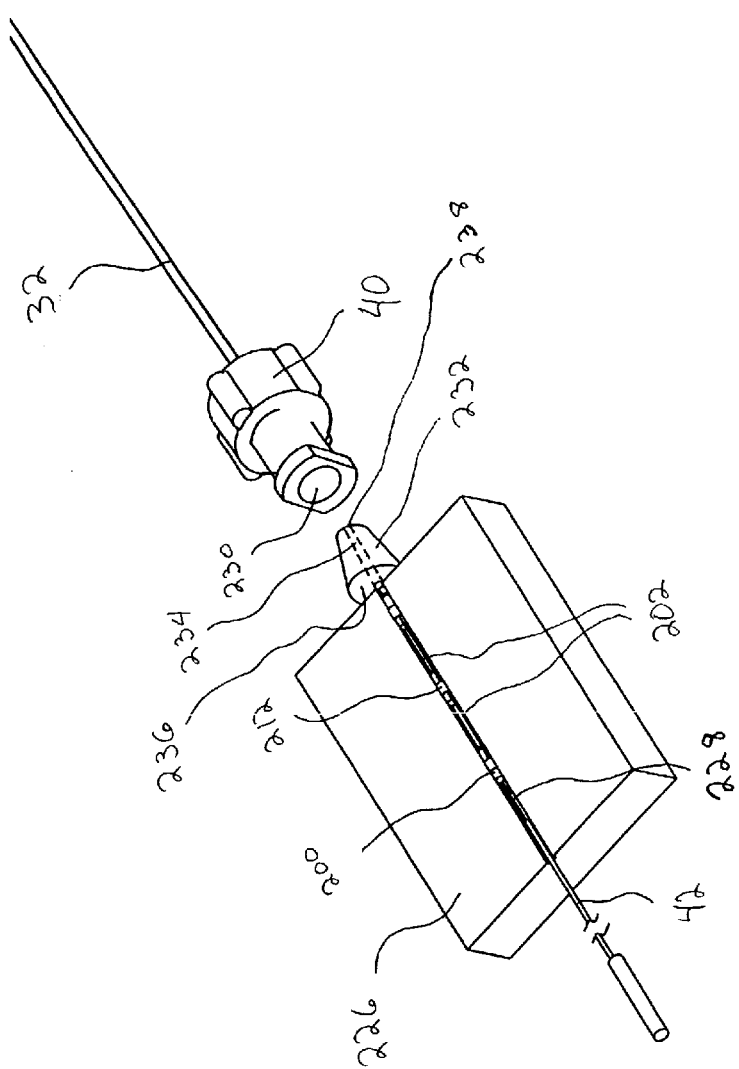
FIG. 30 is a perspective view of a preferred method of inserting the present brachytherapy seed deployment system into a sleeve.
Figure 31:
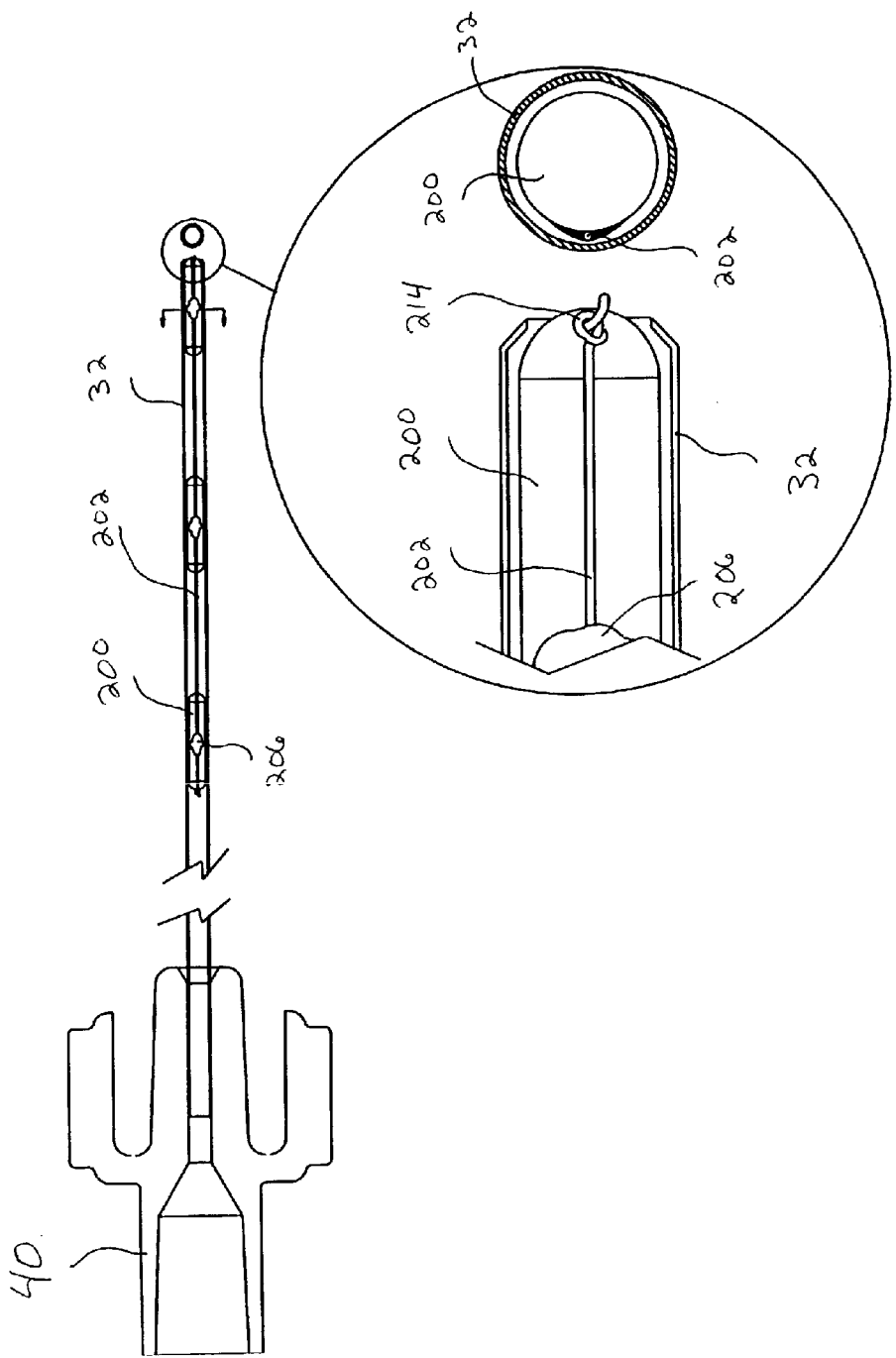
FIG. 31 is a side elevation view and cross-sectional end view of the brachytherapy seed deployment system of FIG. 14 loaded into a sleeve, including a detail view of a distal end of the sleeve, and a detail view of the end view.
Figure 32:
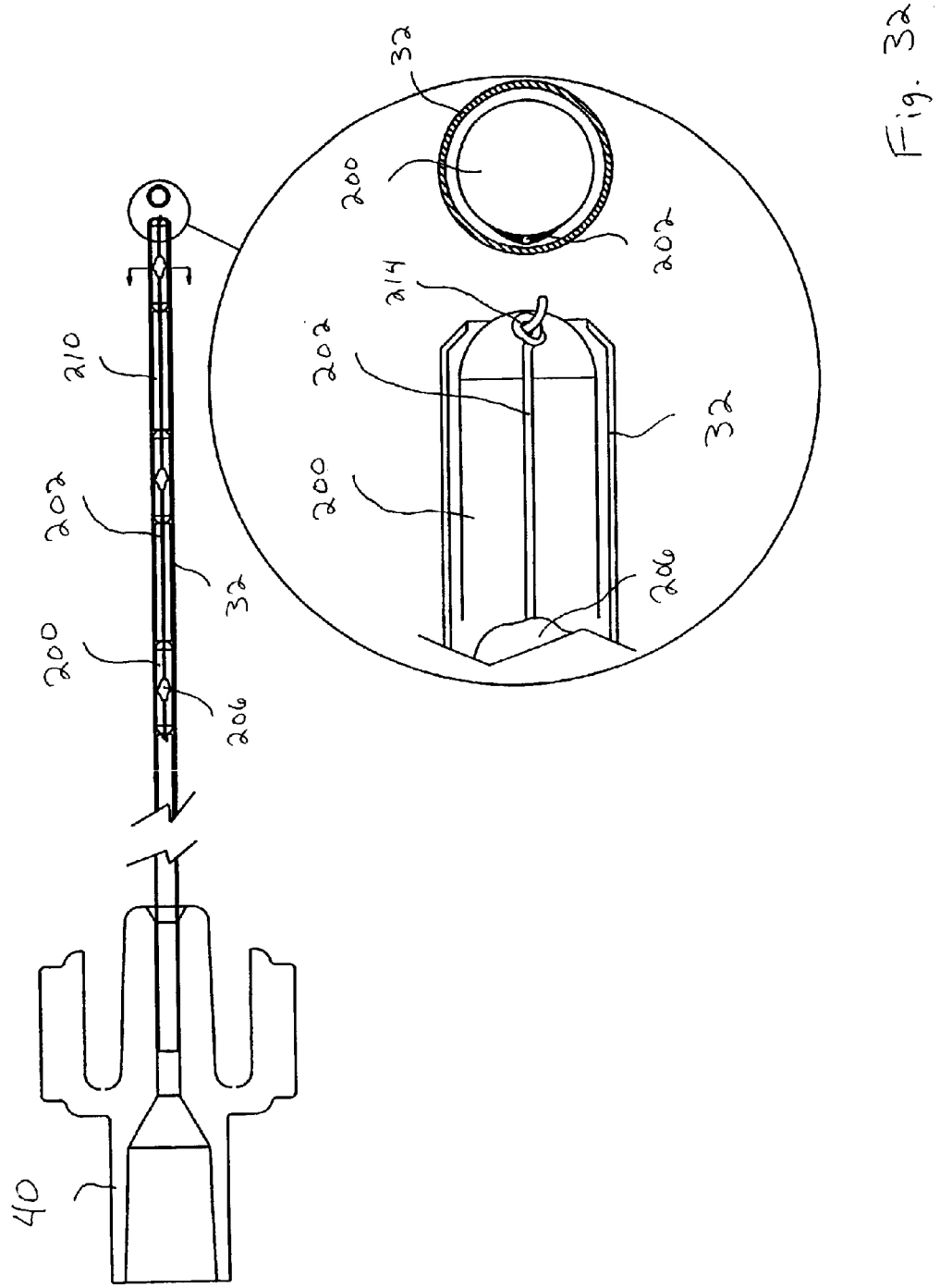
FIG. 32 is a side elevation view and cross-sectional end view of the brachytherapy seed deployment system of FIG. 15 loaded into a sleeve, including a detail view of a distal end of the sleeve, and a detail view of the end view.
Figure 33:
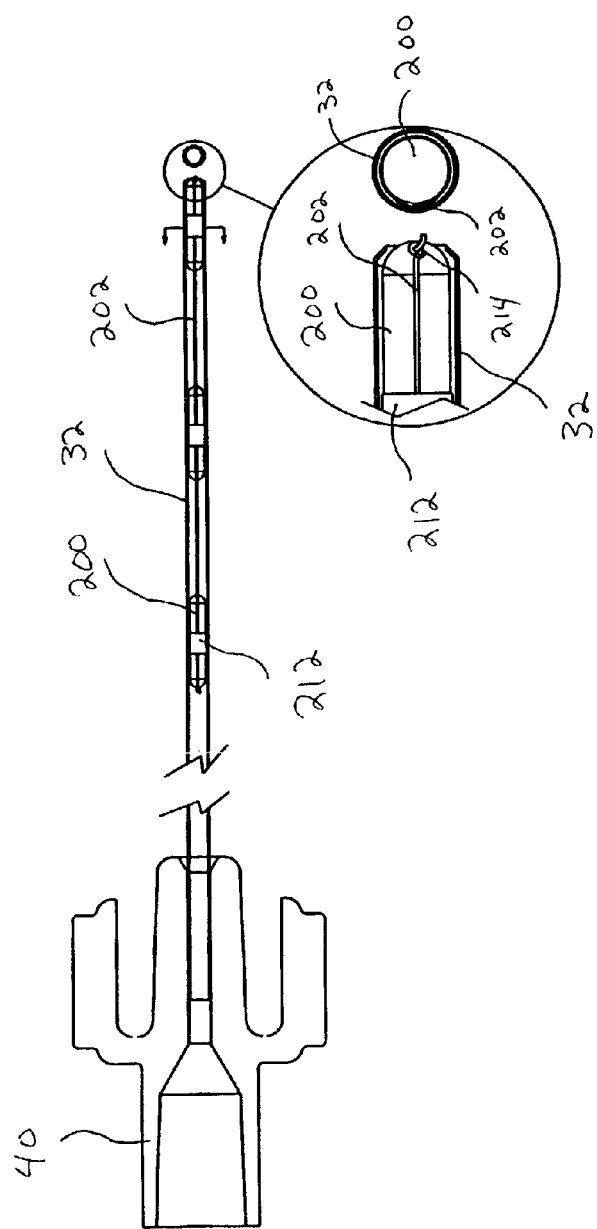
FIG. 33 is a side elevation view and cross-sectional end view of the brachytherapy seed deployment system of FIG. 16 loaded into a sleeve, including a detail view of a distal end of the sleeve, and a detail view of the end view.
Figure 34:
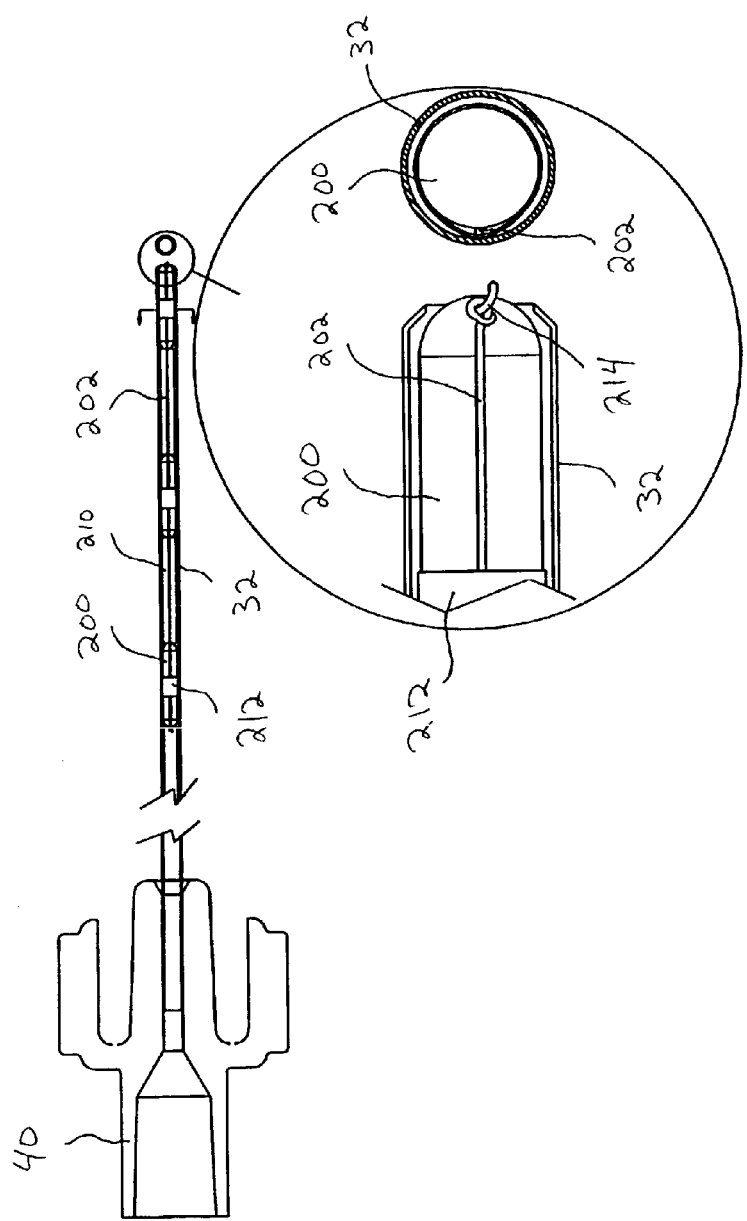
FIG. 34 is a side elevation view and cross-sectional end view of the brachytherapy seed deployment system of FIG. 17 loaded into a sleeve, including a detail view of a distal end of the sleeve, and a detail view of the end view.
Figure 35:
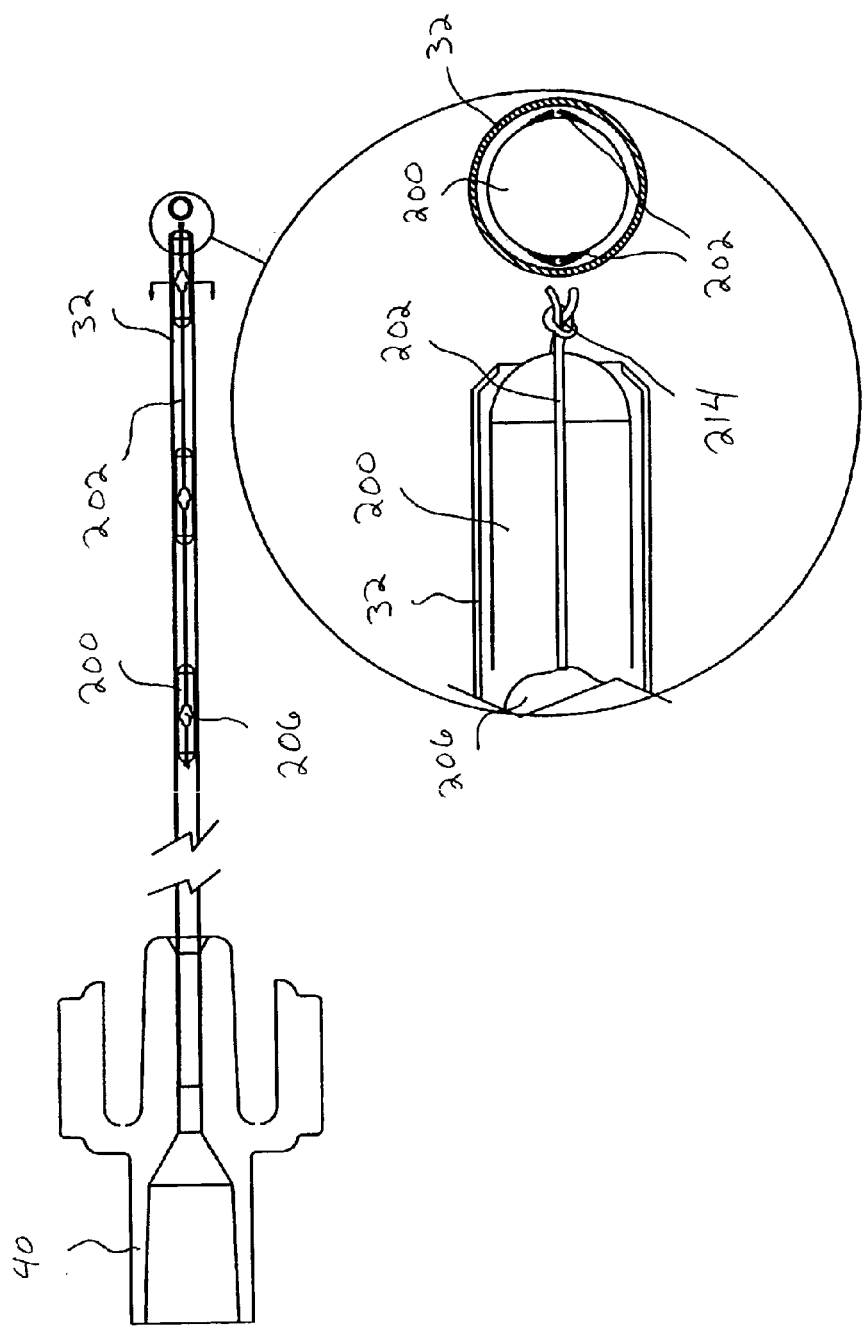
FIG. 35 is a side elevation view and cross-sectional end view of the brachytherapy seed deployment system of FIG. 18 loaded into a sleeve, including a detail view of a distal end of the sleeve, and a detail view of the end view.
Figure 36:
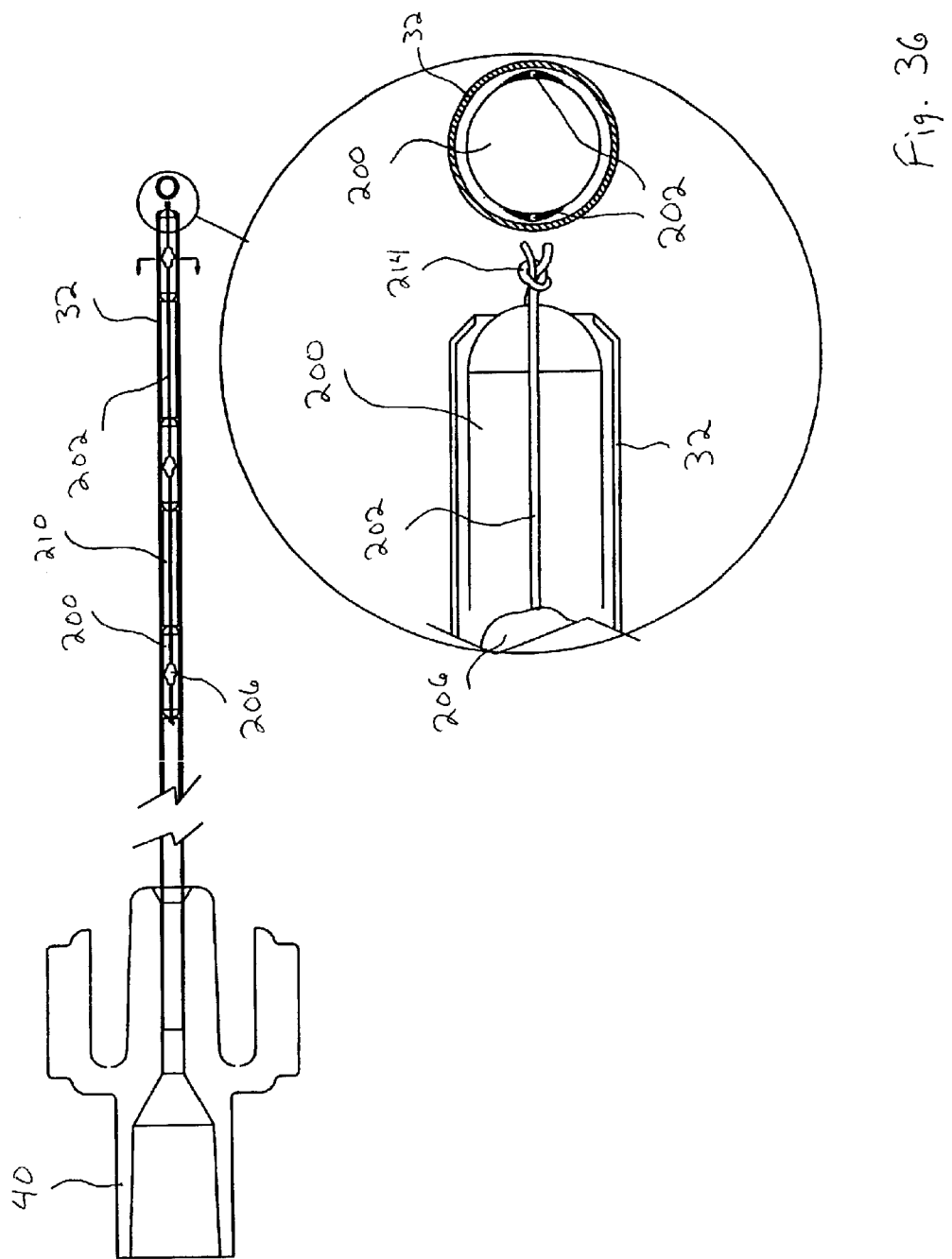
FIG. 36 is a side elevation view and cross-sectional end view of the brachytherapy seed deployment system of FIG. 19 loaded into a sleeve, including a detail view of a distal end of the sleeve, and a detail view of the end view.
Figure 37:
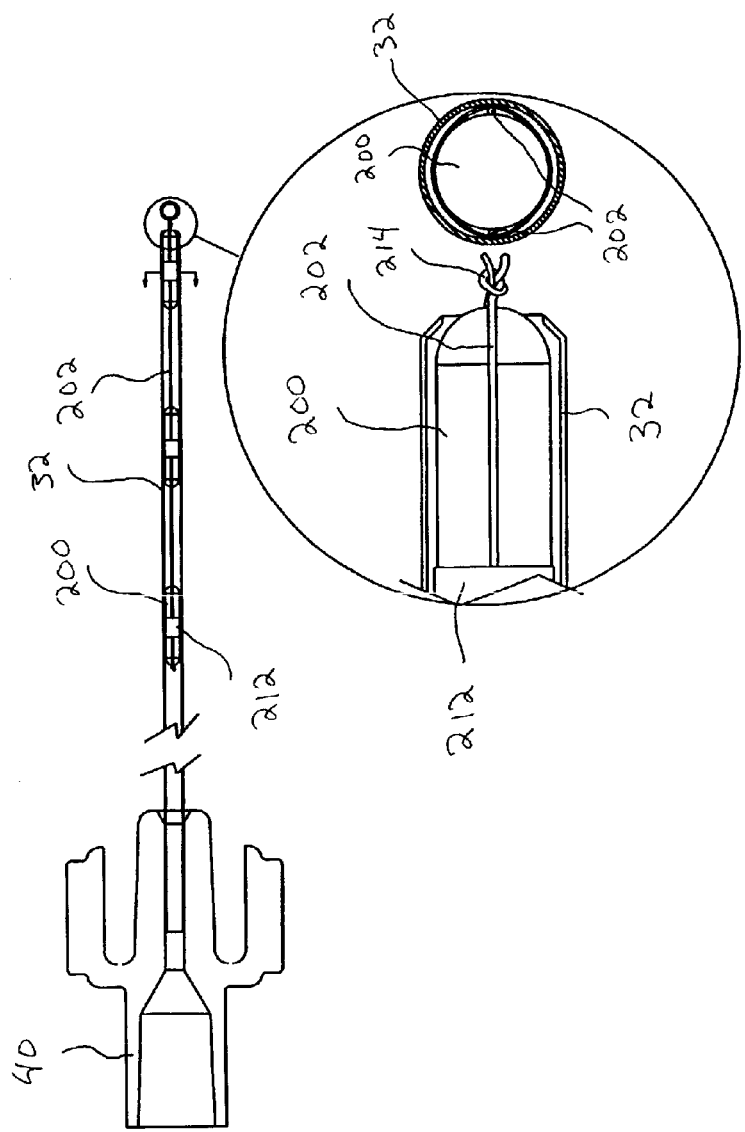
FIG. 37 is a side elevation view and cross-sectional end view of the brachytherapy seed deployment system of FIG. 20 loaded into a sleeve, including a detail view of a distal end of the sleeve, and a detail view of the end view.
Figure 38:
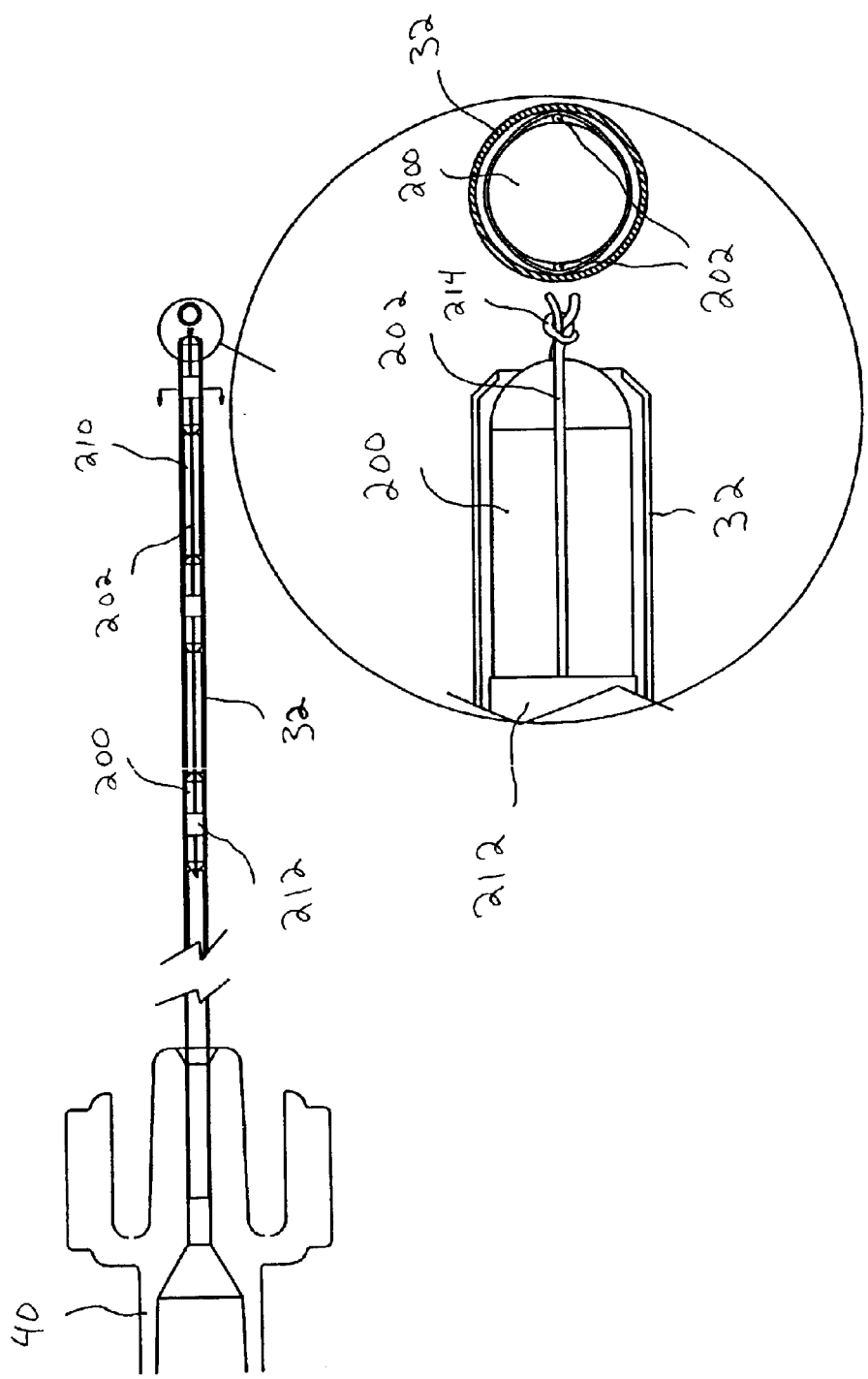
FIG. 38 is a side elevation view and cross-sectional end view of the brachytherapy seed deployment system of FIG. 21 loaded into a sleeve, including a detail view of a distal end of the sleeve, and a detail view of the end view.

Once the seeds 200 and filaments 202 (and collars 212 and spacers 210, if provided) are assembled, the assembly is preferably loaded into a sleeve 32 for implantation. FIG. 30 illustrates a preferred method of loading the sleeve 32. A proximal end of the hub 40 on the sleeve 32 includes an opening 230 having a diameter significantly larger than a diameter of the seed/filament assembly. Therefore, to more easily guide the assembly through the hub 40 and into the tubular portion of the sleeve 32, a conical adapter 232 may be used. The adapter 232 includes a central lumen 234 having a diameter slightly larger than that of the seed/filament assembly. A proximal face 236 of the adapter 232 abuts an edge of the fixture 226 such that the lumen 234 is substantially coaxial with the fixture slot 228. The distal end 238 of the adapter 232 is then inserted into the hub 40 such that a distal face of the adapter substantially abuts a proximal end of the tubular portion of the sleeve 32. Using the obturator 42, the assembler then pushes the seed/filament assembly through the adapter 232, through the hub 40 and into the sleeve 32.

Figure 44:
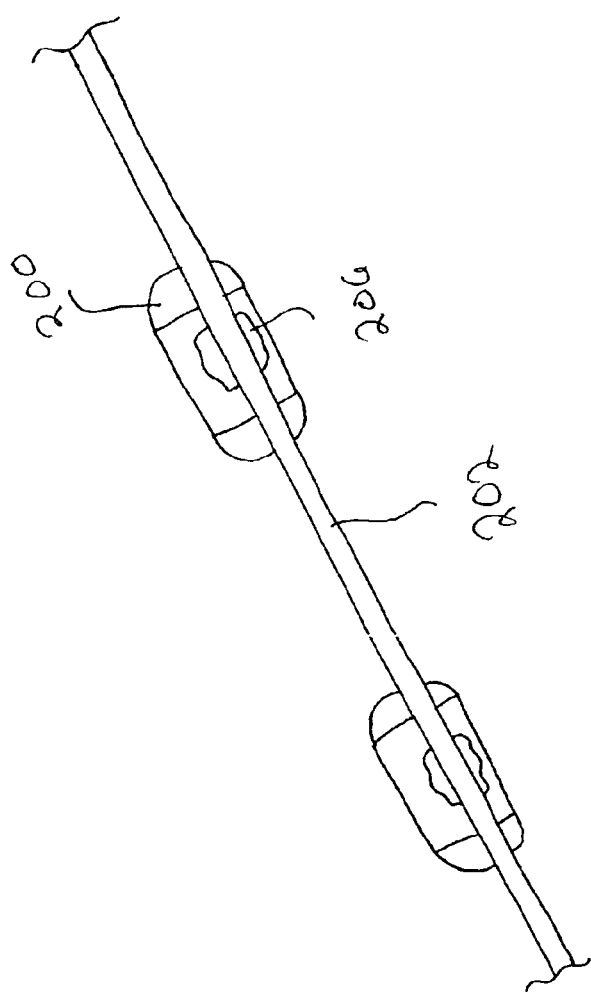
FIG. 44 is a schematic view of another preferred device and method of implanting the present brachytherapy seed deployment system.

FIG. 44 illustrates another preferred embodiment of the present brachytherapy seed deployment system. In this embodiment, the filament 202 comprises a material that is rigid outside the body, and flexible inside the body. For example, the material may be rigid at temperatures below normal human body temperature (98.6° F.), and flexible at normal human body temperature. Alternatively, the material may comprise a matrix that is rigid when exposed to air, but flexible inside the body. Thus, during implantation the rigidity of the filament 202 maintains proper spacing between adjacent seeds 200. Shortly after implantation, however, the filament 202 becomes flexible.

FIG. 45 illustrates another preferred embodiment of the present brachytherapy seed deployment system. In this embodiment, the filament 202 is replaced by a polymer laminate 240. The seeds 200 are laminated between two sheets of a biocompatible polymeric material. Preferred materials include cyanoacrylates and hotmelts. Spacers 210 may be provided between adjacent seeds 200, and anchoring structures such as those described above may be secured to a distal end 242 of the laminate 240. The entire laminate structure is inserted into the prostate capsule 204 in a similar manner as that described above. In one embodiment, if the laminate 240 is bioabsorbable, a filament 202 or filaments 202 may be secured to the seeds 200 as described above prior to the seeds 200 being laminated between the sheets. Thus, once the laminate 240 dissolves, the filament 200 maintains the proper seed spacing. If the laminate 240 permits the radiation to properly treat the cancerous tumor without dissolving, a filament 202 may not be necessary.

Advantageously, in one embodiment the collars 212 hold the seeds 200 to the filament 202 or filaments 202 snugly enough that the seeds 200 will not travel along the filament 202 or filaments 202 after implantation, but loosely enough that an end user of the present brachytherapy seed deployment system may change the spatial configuration of the seeds 200 before implantation. For example, if a physician has available one or more pre-assembled systems including seeds joined by filaments, he or she may disassemble the systems and rearrange the spacing between the seeds in order to tailor the standard seed arrangement to fit a course of treatment.

To rearrange the seeds, the user removes the sleeve 32 from the needle 22. He or she then removes the seeds 200 (and spacers 210 if provided) from the sleeve 32 by pushing them out with the obturator 42. He or she positions the seeds 200 and spacers 210 in the slot 228 on the fixture 226, and removes any spacers 210. Using sterile tweezers, he or she manipulates the spacing between the seeds 200 by sliding the seed/collar assembly along the filament 202 to the desired new location. He or she may then add spacers 210 if desired, and reinsert the assembly into the sleeve 32 as described above.

Although exemplary embodiments of the invention have been shown and described, many changes, modifications and substitutions may be made by one having ordinary skill in the art without necessarily departing from the spirit and scope of this invention.

What is claimed is:

1. A brachytherapy seed deployment system comprising: at least two seeds and a filament secured to the at least two seeds in a manner such that the exterior of the filament is secured to the exterior of the seeds and at least one anchor is located along the filament.

2. The brachytherapy seed deployment system of claim 1, wherein the filament is not bioabsorbable.

3. The brachytherapy seed deployment system of claim 1, wherein the filament is bioabsorbable and a useful life of the seeds is shorter than an amount of time required for the filament to be absorbed.

4. The brachytherapy seed deployment system of claim 1, wherein each seed is independently secured to the filament with an adhesive.

5. The brachytherapy seed deployment system of claim 1, wherein each seed is independently secured to the filament with a cylindrical collar.

6. The brachytherapy seed deployment system of claim 5, wherein the collar comprises a polymeric material that shrinks upon application of heat.

7. The brachytherapy seed deployment system of claim 1, further comprising a second filament.

8. The brachytherapy seed deployment system of claim 1, further comprising at least one spacer located between adjacent seeds.

9. The brachytherapy seed deployment system of claim 1, wherein the anchor comprises a knot in the filament.

10. The brachytherapy seed deployment system of claim 1, wherein the anchor comprises a hook secured to the filament.

11. The brachytherapy seed deployment system of claim 1, wherein the anchor comprises a T bar secured to the filament.

12. The brachytherapy seed deployment system of claim 1, wherein an anchor is secured to a distal seed.

13. The brachytherapy seed deployment system of claim 12, wherein the anchor comprises at least one barb.

14. The brachytherapy seed deployment system of claim 1, wherein the filament comprises a material that is rigid outside the human body and flexible inside the human body.

15. The brachytherapy seed deployment system of claim 14, wherein the filament comprises a material that is rigid at temperatures below normal human body temperature and flexible at normal human body temperature.

16. The brachytherapy seed deployment system of claim 14, wherein the filament comprises a material including a matrix that is rigid outside the body and flexible within the body.

17. A brachytherapy seed deployment system comprising: at least two seeds; a filament; and at least one anchor located along the filament, wherein the filament is secured to the at least two seeds; a sleeve including a central lumen for containing the seeds and filament; and a needle including a central lumen for containing the sleeve.

18. The brachytherapy seed deployment system of claim 17, further comprising an obturator insertable through a proximal end of the sleeve for ejecting the seeds and filament from the sleeve.

19. The brachytherapy seed deployment system of claim 17, wherein the filament comprises non-bioabsorbable materials.

20. The brachytherapy seed deployment system of claim 17, wherein the needle and/or the sleeve further comprises a hub.

21. A method of assembling a brachytherapy seed deployment system, the method comprising the steps of: providing a fixture including a longitudinal slot; placing a filament within the slot; pulling the filament taut; sliding at least one cylindrical collar onto the filament; inserting a seed into the at least one collar; locating the seed and collar at a desired point along a length of the filament; and securing the seed and collar to the filament.

22. The method of assembling a brachytherapy seed deployment system of claim 21, further comprising the step of locating an anchor along the filament.

23. The method of assembling a brachytherapy seed deployment system of claim 21, further comprising the step of providing a second filament.

24. The method of assembling a brachytherapy seed deployment system of claim 23, wherein the first and second filaments are located on opposite sides of the seed.

25. The method of assembling a brachytherapy seed deployment system of claim 21, wherein the seed and collar are secured to the filament by heat shrinking.

26. The method of assembling a brachytherapy seed deployment system of claim 21, further comprising the step of inserting at least one spacer between adjacent seeds.

27. The method of assembling a brachytherapy seed deployment system of claim 21, further comprising the step of knotting and cutting an end of the filament.

28. The method of assembling a brachytherapy seed deployment system of claim 21, further comprising the step of inserting the seed, collar and filament into a sleeve.

29. A method of implanting brachytherapy seeds, the method comprising the steps of: providing a needle, the needle containing a sleeve, the sleeve containing at least two seeds tethered to one another by a filament; penetrating a cancerous region with the needle; and ejecting the seeds from the sleeve and implanting the seeds in the cancerous region.

30. The method of implanting brachytherapy seeds of claim 29, wherein the seeds are ejected from the sleeve by an obturator inserted through a proximal end of the sleeve.

31. The method of implanting brachytherapy seeds of claim 29, wherein the filament includes an anchor.

32. The method of implanting brachytherapy seeds of claim 31, wherein the anchor engages body tissue.

33. The method of implanting brachytherapy seeds of claim 32, wherein as the needle and sleeve are withdrawn from the cancerous region, the anchored filament creates tension in the filament, maintaining a desired spacing of the seeds.

34. The method of implanting brachytherapy seeds of claim 31, wherein the anchor comprises a knot in the filament.

35. The method of implanting brachytherapy seeds of claim 31, wherein the anchor comprises a hook.

36. The method of implanting brachytherapy seeds of claim 31, wherein the anchor comprises a T bar.

37. The method of implanting brachytherapy seeds of claim 31, wherein a distal seed includes a notch, and a rigid wire engages the notch to hold the distal seed in place in the cancerous region as the sleeve and needle are withdrawn.

38. A brachytherapy seed deployment system comprising: at least two seeds; a laminate encapsulating the at least two seeds; and a filament having at least one anchor located thereon, wherein the filament is secured to the at least two seeds.

39. The brachytherapy seed deployment system of claim 38, wherein the laminate comprises at least two sheets of a biocompatible polymeric material.

40. The brachytherapy seed deployment system of claim 38, further comprising at least one spacer between adjacent seeds.

41. The brachytherapy seed deployment system of claim 38, wherein the filament and seeds are located between two sheets of a biocompatible polymeric material.

42. A method of securing at least two brachytherapy seeds to a filament, the method comprising the steps of: providing a filament having one or more collars located thereon; and securing a first seed and a second seed to the filament with the collars in a manner such that the exterior of the filament is secured to the collars such that the two seeds are tethered to one another by the filament.

43. The method of securing at least two brachytherapy seeds to a filament of claim 42, wherein the seeds are secured via an adhesive.

44. The method of securing at least two brachytherapy seeds to a filament of claim 42, wherein the seeds are secured to the filament via a heat-shrunk collar.

45. The method of securing at least two brachytherapy seeds to a filament of claim 42, further comprising the step of placing a spacer between the seeds.

46. The method of securing at least two brachytherapy seeds to a filament of claim 45, wherein the spacer is secured to the filament.

47. A brachytherapy seed deployment system comprising:
at least two collars, a filament and at least two seeds; wherein the at least two seeds are retained in the collars, and the collars are secured to the filament.

48. The brachytherapy seed deployment system of claim 47, wherein the filament is not bioabsorbable.

49. The brachytherapy seed deployment system of claim 47, wherein the collar comprises a polymeric material that shrinks upon application of heat.

50. The brachytherapy seed deployment system of claim 47, further comprising at least one spacer located between adjacent seeds.

51. A brachytherapy seed deployment system comprising:
at least two seeds; at least one spacer; and a filament secured to the at least two seeds in a manner such that the exterior of the filament is secured to the seeds, and the spacer is located between adjacent seeds.

52. The brachytherapy seed deployment system of claim 51, wherein the filament is not bioabsorbable.

53. The brachytherapy seed deployment system of claim 51, wherein each seed is independently secured to the filament with at least one adhesive.

54. The brachytherapy seed deployment system of claim 53, wherein at least one anchor is located along the filament.

* * * * *